United States Patent
Provenza et al.

(10) Patent No.: US 11,612,748 B2
(45) Date of Patent: Mar. 28, 2023

(54) SYSTEMS, METHODS AND MEDIA FOR DETECTING AND FACILITATING AN EFFORTFUL MENTAL TASK BY PROVIDING REAL-TIME DEEP BRAIN STIMULATION

(71) Applicants: The General Hospital Corporation, Boston, MA (US); Brown University, Providence, RI (US)

(72) Inventors: Nicole Provenza, Providence, RI (US); David Borton, Pawtucket, RI (US); Alik Widge, Somerville, MA (US); Darin Dougherty, Charlestown, MA (US); Emad Eskandar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 558 days.

(21) Appl. No.: 16/607,989

(22) PCT Filed: Apr. 25, 2018

(86) PCT No.: PCT/US2018/029268
§ 371 (c)(1),
(2) Date: Oct. 24, 2019

(87) PCT Pub. No.: WO2019/027517
PCT Pub. Date: Feb. 7, 2019

(65) Prior Publication Data
US 2021/0106830 A1  Apr. 15, 2021

Related U.S. Application Data

(60) Provisional application No. 62/489,703, filed on Apr. 25, 2017.

(51) Int. Cl.
*A61N 1/36* (2006.01)
*A61B 5/291* (2021.01)
(Continued)

(52) U.S. Cl.
CPC .......... *A61N 1/36092* (2013.01); *A61B 5/291* (2021.01); *A61B 5/37* (2021.01);
(Continued)

(58) Field of Classification Search
CPC ............ A61N 1/36092; A61N 1/36139; A61N 1/0534; A61B 5/291; A61B 5/37; A61B 5/6847; A61B 5/7267
See application file for complete search history.

(56) References Cited

U.S. PATENT DOCUMENTS 8,706,205 B2  4/2014  Shahaf
8,774,923 B2  7/2014  Rom
(Continued)

FOREIGN PATENT DOCUMENTS

WO   2013039577 A2   3/2013

OTHER PUBLICATIONS

Malone, D. A. et al. Deep Brain Stimulation of the Ventral Capsule/Nentral Striatum for Treatment-Resistant Depression. Biol. Psychiatry 65, 267-275 (2009).
(Continued)

*Primary Examiner* — Joseph M Dietrich
(74) *Attorney, Agent, or Firm* — Quarles & Brady LLP

(57) ABSTRACT

In accordance with some embodiments of the disclosed subject matter, mechanisms (which can, for example, include systems, methods, and media) for detecting an effortful mental state providing real-time deep brain stimulation to enhance performance of effortful mental tasks are provided. In some embodiments, system for detecting and facilitating effortful mental states is provided, the system
(Continued)

comprising: monitoring sensors to capture neural activity from a subject's brain; an implanted stimulator to provide electrical stimulation to the subject's brain; a hardware processor programmed to: correlate activity in a first and second region of the subject brain during task performance; correlate activity in the first and second regions during task non performance; train a support vector machine (SVM) using the correlations as first and second class examples; and provide stimulation to augment brain function when the SVM indicates, based on activity in the first and second regions, the subject is in the mental state.

24 Claims, 32 Drawing Sheets

(51) Int. Cl.
  *A61B 5/37*  (2021.01)
  *A61B 5/00*  (2006.01)
  *A61N 1/05*  (2006.01)

(52) U.S. Cl.
  CPC .......... *A61B 5/6847* (2013.01); *A61B 5/7267* (2013.01); *A61N 1/0534* (2013.01); *A61N 1/36139* (2013.01)

(56) References Cited

U.S. PATENT DOCUMENTS

| | | | |
|---|---|---|---|
| 11,241,188 B2* | 2/2022 | Widge | A61B 5/377 |
| 2010/0302270 A1 | 12/2010 | Echauz | |
| 2015/0066104 A1 | 3/2015 | Wingeier | |
| 2015/0351655 A1 | 12/2015 | Coleman | |
| 2016/0144186 A1 | 5/2016 | Kaemmerer | |
| 2017/0042474 A1 | 2/2017 | Widge | |

OTHER PUBLICATIONS

Mayberg, H. S. Targeted electrode-based modulation of neural circuits for depression. J. Clin. Invest. 119, 717-725 (2009).

McCane, L. M., et al. "Brain-computer interface (BCI) evaluation in people with amyotrophic lateral sclerosis." Amyotrophic lateral sclerosis and frontotemporal degeneration 15.3-4 (2014): 207-215.

McTeague, L. M., et al. 2017. "Identification of Common Neural Circuit Disruptions in Cognitive Control across Psychiatric Disorders." American Journal of Psychiatry 174 (7): 676-85. doi:10.1176/appi.ajp.2017.16040400.

Melcher, T. et al. 2008. "Functional Brain Abnormalities in Psychiatric Disorders: Neural Mechanisms to Detect and Resolve Cognitive Conflict and Interference." Brain Research Reviews 59 (1). Elsevier B.V.: 96-124. doi:10.1016/j.brainresrev.2008.06.003.

Michelson, N. J., et al. "Multi-scale, multi-modal analysis uncovers complex relationship at the brain tissue-implant neural interface: new emphasis on the biological interface." Journal of neural engineering 15.3 (2018): 033001.

Nigbur, R. et al. "Theta power as a marker for cognitive interference." Clinical Neurophysiology 122.11 (2011): 2185-2194.

Niki, H. et al. Prefrontal and cingulate unit activity during timing behavior in the monkey. Brain Res. 171, 213-224 (1979).

Nishijo, H. et al. Single neuron responses in the monkey anterior cingulate cortex during visual discrimination. Neurosci. Lett. 227, 79-82 (1997).

Oostenveld, R. et al. 2011. "FieldTrip: Open Source Software for Advanced Analysis of MEG, EEG, and Invasive Electrophysiological Data." Computational Intelligence and Neuroscience 2011. doi:10.1155/2011/156869.

Pelli, D. G. The VideoToolbox software for visual psychophysics: transforming numbers into movies. Spatial Vision 10, 437-442 (1997).

Procyk, E., et al. Anterior cingulate activity during routine and non-routine sequential behaviors in macaques. Nat. Neurosci. 3, 502-508 (2000).

Provenza, N., et al. "The case for responsive neuromodulation to treat severe intractable mental disorders." Frontiers in neuroscience 13 (2019): 152.

Provenza, NR et al. "Functional Interference Distinguishes Task States Across Cortical and Subcortical networks" Poster presented Nov. 14, 2016. Neuroscience 2016, San Diego.

Raichle, M. E., et al. "A default mode of brain function." Proceedings of the National Academy of Sciences 98.2 (2001): 676-682.

Ramirez-Zamora, A., et al. "Evolving applications, technological challenges and future opportunities in neuromodulation: Proceedings of the Fifth Annual Deep Brain Stimulation Think Tank." Frontiers in neuroscience 11 (2018): 734.

Rao, V. R., et al. "Direct electrical stimulation of lateral orbitofrontal cortex acutely improves mood in individuals with symptoms of depression." Current Biology 28.24 (2018): 3893-3902.

Robbins, T. W., et al. 2012. "Neurocognitive Endophenotypes of Impulsivity and Compulsivity: Towards Dimensional Psychiatry." Trends in Cognitive Sciences 16 (1): 81-91. doi:10.1016/j.tics.2011. 11.009.

Sani, O. G., et al. "Mood variations decoded from multi-site intracranial human brain activity." Nature biotechnology 36.10 (2018): 954.

Sellers, E. W., et al. "A brain-computer interface for long-term independent home use." Amyotrophic lateral sclerosis 11.5 (2010): 449-455.

Simpson, J. R., et al. Emotion-induced changes in human medial prefrontal cortex: I. During cognitive task performance. Proc. Natl. Acad Sci. US. A. 98, 683-687 (2001).

Smith, E. H., et al. "Frequency-dependent representation of reinforcement-related information in the human medial and lateral prefrontal cortex." Journal of Neuroscience 35.48 (2015): 15827-15836.

Stanslaski, S., et al. "Design and validation of a fully implantable, chronic, closed-loop neuromodulation device with concurrent sensing and stimulation." IEEE Transactions on Neural Systems and Rehabilitation Engineering 20.4 (2012): 410-421.

Stephen et al., "Assessing dynamics, spatial scale, and uncertainty in task-related brain network analyses," Front. Comput. Neurosci. 8, 31 (2014).

Swann, N. C., et al. "Adaptive deep brain stimulation for Parkinson's disease using motor cortex sensing." Journal of neural engineering 15.4 (2018): 046006.

Swann, N. C., et al. "Chronic multisite brain recordings from a totally implantable bidirectional neural interface: experience in 5 patients with Parkinson's disease." Journal of neurosurgery 128.2 (2017): 605-616.

Trivedi, M. H., et al. 2014. "Cognitive Dysfunction in Unipolar Depression: Implications for Treatment." Journal of Affective Disorders 152-154 (1). Elsevier: 19-27. doi:10.1016/j.jad.2013.09.012.

Tyagi, H., et al. "A randomized trial directly comparing ventral capsule and anteromedial subthalamic nucleus stimulation in obsessive-compulsive disorder: clinical and imaging evidence for dissociable effects." Biological psychiatry 85.9 (2019): 726-734.

Vansteensel, M. J., et al. "Fully implanted brain—computer interface in a locked-in patient with ALS." New England Journal of Medicine 375.21 (2016): 2060-2066.

Whalen, P. J. et al. The emotional counting stroop paradigm: A functional magnetic resonance imaging probe of the anterior cingulate affective division. Biol. Psychiatry 44, 1219-1228 (1998).

Widge, A. S., et al. "Closing the loop on deep brain stimulation for treatment-resistant depression." Focus 16.3 (2018): 305-313.

Widge, A. S., et al. "Deep brain stimulation for treatment-refractory mood and obsessive-compulsive disorders." Current Behavioral Neuroscience Reports 2.4 (2015): 187-197.

Widge, A. S., et al. "Deep brain stimulation of the internal capsule enhances human cognitive control and prefrontal cortex function." Nature communications 10.1 (2019): 1-11.

(56) References Cited

OTHER PUBLICATIONS

Widge, A. S., et al. 2016. "Treating Refractory Mental Illness with Closed-Loop Brain Stimulation: Progress towards a Patient-Specific Transdiagnostic Approach." Experimental Neurology, doi:10.1016/j.expneurol.2016.07.021.
Williams, Z. M., et al. 2006. "Selective Enhancement of Associative Learning by Microstimulation of the Anterior Caudate." Nature Neuroscience 9 (4): 562-68. doi:10.1038/nn1662.
Yousefi, A., et al. "COMPASS: an open-source, general-purpose software toolkit for computational psychiatry." Frontiers in neuroscience 12 (2018): 957.
Yousefi, A., et al. "Decoding hidden cognitive states from behavior and physiology using a bayesian approach." Neural computation 31.9 (2019): 1751-1788.
Amemori, Ki et al. 2012. "Localized Microstimulation of Primate Pregenual Cingulate Cortex Induces Negative Decision-Making." Nature Neuroscience 15 (5): 776-85. doi:10.1038/nn.3088.
Badre, D. et al. "Left ventrolateral prefrontal cortex and the cognitive control of memory." Neuropsychologia 45.13 (2007): 2883-2901.
Bastos, A. M. et al. A Tutorial Review of Functional Connectivity Analysis Methods and Their Interpretational Pitfalls. Front. Syst. Neurosci. 9, 175 (2015).
Basu, I., et al. "Consistent linear and non-linear responses to invasive electrical brain stimulation across individuals and primate species with implanted electrodes." Brain stimulation (2019).
Brainard, D. The Psychophysics Toolbox. Spat. Vis. 10, 433-436 (1997).
Brandman, D. M., et al. "human intracortical recording and neural decoding for brain-computer interfaces." IEEE Transactions on Neural Systems and Rehabilitation Engineering 25.10 (2017): 1687-1696.
Brandman, D. M., et al. "Rapid calibration of an intracortical brain—computer interface for people with tetraplegia." Journal of neural engineering 15.2 (2018): 026007.
Brodersen, K. H., et al. "The balanced accuracy and its posterior distribution." 2010 20th International Conference on Pattern Recognition. IEEE, 2010.
Bush, G, et al. 2003. "The Multi-Source Interference Task: Validation Study with fMRI in Individual Subjects." Molecular Psychiatry 8 (1): 60-70. doi:10.1038/sj.mp.4001217.
Bush, G, et al. 2006. "The Multi-Source Interference Task: An fMRI Task That Reliably Activates the Cingulo-Frontal-Parietal Cognitive/attention Network." Nature Protocols 1 (1): 308-13. doi:10.1038/nprot.2006.48.
Cavanagh, JF, et al. 2011. "Influence Over Decision Threshold." Nature Neuroscience 14 (11): 1462-67. doi:10.1038/nn.2925. Subthalamic.
Cavanagh, JF., et al. "Frontal theta as a mechanism for cognitive control." Trends in cognitive sciences 18.8 (2014): 414-421.
Chang, C-C, et al. 2011. "Libsvm." ACM Transactions on Intelligent Systems and Technology 2 (3): 1-27. doi:10.1 145/1961189. 1961199.
Cocchi, L. et al. Functional alterations of large-scale brain networks related to cognitive control in obsessive-compulsive disorder. Hum. Brain Mapp. 33, 1089-1106 (2012).
Cohen, M. X., et al. "Midfrontal conflict-related theta-band power reflects neural oscillations that predict behavior." Journal of Neurophysiology 110.12 (2013): 2752-2763.
Cohen, M. X., et al. "Single-trial regression elucidates the role of prefrontal theta oscillations in response conflict." Frontiers in psychology 2 (2011): 30.
Dangi, S, et al. "Design and analysis of closed-loop decoder adaptation algorithms for brain-machine interfaces." Neural computation 25.7 (2013): 1693-1731.
Davey, C. G., et al. Task-related deactivation and functional connectivity of the subgenual cingulate cortex in major depressive disorder. Front. Psychiatry 3, 1-8 (2012).

Desikan, R. S. et al. An automated labeling system for subdividing the human cerebral cortex on MRI scans into gyral based regions of interest. Neuroimage 31, 968-980 (2006).
Dougherty, D. D. et al. A Randomized Sham-Controlled Trial of Deep Brain Stimulation of the Ventral CapsuleNentral Striatum for Chronic Treatment-Resistant Depression. Biol. Psychiatry 78, 240-248 (2015).
Dvorak, D, et al. "Cognitive behavior classification from scalp EEG signals." IEEE transactions on neural systems and rehabilitation engineering 26.4 (2018): 729-739.
Dykstra, A. R. et al. Individualized localization and cortical surface-based registration of intracranial electrodes. Neuroimage 59, 3563-3570 (2012).
Elliott, R. et al. "Dissociable functions in the medial and lateral orbitofrontal cortex: evidence from human neuroimaging studies." Cerebral cortex 10.3 (2000): 308-317.
Etkin, A. et al. 2011. "Emotional Processing in Anterior Cingulate and Medial Prefrontal Cortex." Trends in Cognitive Sciences 15 (2). Elsevier Ltd: 85-93. doi:10.1016/j.tics.2010.11.004.
Etkin, A. et al. 2015. "A Cognitive-Emotional Biomarker for Predicting Remission with Antidepressant Medications: A Report from the iSPOT-D Trial." Neuropsychopharmacology 40 (6). Nature Publishing Group: 1332-42. doi:10.1038/npp.2014.333.
Etkin, A. et al. Common abnormalities and disorder-specific compensation during implicit regulation of emotional processing in generalized anxiety and major depressive disorders. Am. J Psychiatry 168, 968-978 (2011).
Etkin, A., et al. Failure of anterior cingulate activation and connectivity with the amygdala during implicit regulation of emotional processing in generalized anxiety disorder. Am. J Psychiatry 167, 545-554 (2010).
Etkin, A., et al. Resolving Emotional Conflict: A Role for the Rostral Anterior Cingulate Cortex in Modulating Activity in the Amygdala. Neuron 51, 871-882 (2006).
Ezzyat, Y et al. 2017. "Direct Brain Stimulation Modulates Encoding States and Memory Performance in Humans." Current Biology 27 (9). Elsevier Ltd.: 1251-58. doi:10.1016/j.cub.2017.03.028.
Ezzyat, Y et al. 2018. "Closed-Loop Stimulation of Temporal Cortex Rescues Functional Networks and Improves Memory." Nature Communications. doi:10.1038/s41467-017-02753-0.
Fair, D. A. et al. A method for using blocked and event-related fMRI data to study 'resting state' functional connectivity. Neuroimage 35, 396-405 (2007).
Fineberg, Na, et al. 2010. "Probing Compulsive and Impulsive Behaviors, from Animal Models to Endophenotypes: A Narrative Review." Neuropsychopharmacology 35 (3). Nature Publishing Group: 591-604. doi:10.1038/npp.2009.185.
Fischl, B. FreeSurfer. Neuroimage 62, 774-781 (2012).
Galar, M., et al. A review on ensembles for the class imbalance problem: Bagging-, boosting-, and hybrid-based approaches. IEEE Trans. Syst. Man Cybern. Part C Appl. Rev. 42, 463-484 (2012).
Gillan, C. M., et al. "Characterizing a psychiatric symptom dimension related to deficits in goal-directed control." Elife 5 (2016): e11305.
Greenberg, B. D. et al. Deep brain stimulation of the ventral internal capsule/ventral striatum for obsessive-compulsive disorder: worldwide experience. Mol. Psychiatry 15, 64-79 (2010).
Greicius, M. D., et al. "Functional connectivity in the resting brain: a network analysis of the default mode hypothesis." Proceedings of the National Academy of Sciences 100.1 (2003): 253-258.
Grisanzio, K. A., et al. 2017. "Transdiagnostic Symptom Clusters and Associations With Brain, Behavior, and Daily Function in Mood, Anxiety, and Trauma Disorders." JAMA Psychiatry 94305: 1-9. doi:10.1001/iamapsychiatry.2017.3951.
Herron, J. A., et al. "Cortical brain—computer interface for closed-loop deep brain stimulation." IEEE Transactions on Neural Systems and Rehabilitation Engineering 25.11 (2017): 2180-2187.
Hochberg, L. R., et al. "Neuronal ensemble control of prosthetic devices by a human with tetraplegia." Nature 442.7099 (2006): 164.
Hochberg, L. R., et al. "Reach and grasp by people with tetraplegia using a neurally controlled robotic arm." Nature 485.7398 (2012): 372.

(56) References Cited

OTHER PUBLICATIONS

Holtzheimer, P. E., et al. 2017. "Subcallosal Cingulate Deep Brain Stimulation for Treatment-Resistant Depression: A Multisite, Randomised, Sham-Controlled Trial." The Lancet Psychiatry 4(11). Elsevier Ltd: 839-49. doi: 10.1016/S2215-0366(17)30371-1.

Insel, T. R. 2009. "Disruptive Insights in Psychiatry: Transforming a Clinical Discipline." Journal of Clinical Investigation 119 (4): 700-705. doi:10.1172/JCI38832.

International Searching Authority, International Search Report and Written Opinion for application PCT/US2018/029268, dated Jan. 29, 2019.

Jarosiewicz, B., et al. "Virtual typing by people with tetraplegia using a self-calibrating intracortical brain-computer interface." Science translational medicine 7.313 (2015): 313ra179-313ra179.

Katnani, H. A., et al. 2016. "Temporally Coordinated Deep Brain Stimulation in the Dorsal and Ventral Striatum Synergistically Enhances Associative Learning." Scientific Reports 6 (1). Nature Publishing Group: 18806. doi:10.1038/srep18806.

Kirkby, L. A., et al. "An amygdala-hippocampus subnetwork that encodes variation in human mood." Cell 175.6 (2018): 1688-1700.

Kleiner, M. et al. What's new in Psychtoolbox-3. Perception 36, 1 (2007).

Koyama, T. et al. 2001. "Anterior Cingulate Activity during Pain-Avoidance and Reward Tasks in Monkeys." Neuroscience Research 39 (4): 421-30. doi:10.1016/S0168-0102(01)00197-3.

Lo, M-C, et al. "Closed-loop neuromodulation systems: next-generation treatments for psychiatric illness." International Review of Psychiatry 29.2 (2017): 191-204.

\* cited by examiner

1. Initialization: $Acc = []$; $Var = [1, \ldots, N]$;
2. Repeat for $i$ ranging from 1 to N
   a. Remove the $i$th element in $Var$
   b. Train the SVM classifier with all training data and variables $Var$
   c. Test the SVM classifier with all testing data and variables $Var$
      $$Acc(i) = Accuracy$$
   d. Replace the $i$th element in $Features$
3. Find the variable, $Var_{min}$, that minimizes $Accuracy$, and remove it from the variables set
   $$Ranked(t) = Var_{min}$$
   $$Var = [1, \ldots, remove - 1, remove + 1, \ldots, M]$$
4. Repeat steps 1-3 until $Var$ is empty, and all variables are ranked

FIG. 8

| # | Patient Label | MSIT sessions | | ECR sessions | | # of NSPs | # of Electrodes (8-16 contacts ea.) | |
|---|---|---|---|---|---|---|---|---|
| | | 1 | 2 | 1 | 2 | | Left | Right |
| 1 | 79 | x | | | | 1 | 6 | 6 |
| 2 | 85 | | | x | | 1 | 5 | 7 |
| 3 | 86 | x | | x | | 1 | 9 | 5 |
| 4 | 88 | | | x | | 1 | 6 | 6 |
| 5 | 89 | x | | x | | 1 | 5 | 6 |
| 6 | 90 | x | | x | | 1 | 7 | 7 |
| 7 | 95 | x | | | | 2 | 7 | 7 |
| 8 | 96 | x | | x | | 2 | 8 | 5 |
| 9 | 99 | x | x | x | x | 2 | 8 | 6 |
| 10 | 101 | | | x | | 2 | 9 | 4 |
| 11 | 102 | x | | x | | 2 | 9 | 7 |
| 12 | 104 | x | x | x | | 2 | 9 | 5 |
| 13 | 106 | x | | x | | 2 | 9 | 7 |
| 14 | 107 | x | x | x | x | 2 | 9 | 8 |

FIG. 30

|  | MG Label | 79 | 86 | 89 | 90 | 95 | 96 | 99 | 102 | 104 | 106 | 107 |
|---|---|---|---|---|---|---|---|---|---|---|---|---|
| Left | Accumb. |  |  |  |  |  | 2 |  |  | 1 |  | 1 |
|  | Amyg. | 2 | 4 | 4 | 4 | 5 | 2 | 5 | 5 |  | 2 | 4 |
|  | Caudate |  |  |  |  |  | 7 | 3 | 2 | 7 |  | 7 |
|  | Hipp | 1 | 5 | 2 | 5 | 7 | 4 | 10 |  |  | 6 | 11 |
|  | dACC | 4 | 1 | 1 | 5 | 3 |  | 5 |  | 4 | 2 | 6 |
|  | dlPFC | 12 | 8 | 10 | 9 | 15 | 15 | 31 | 16 | 43 | 33 | 35 |
|  | dmPFC |  | 7 | 1 |  | 3 | 3 | 2 | 19 | 1 | 4 | 6 |
|  | Insula |  |  |  |  | 1 |  |  | 2 | 3 |  |  |
|  | lOFC | 3 | 4 |  | 2 | 7 | 8 | 7 | 8 | 8 | 4 | 8 |
|  | mOFC | 2 | 2 | 2 | 1 | 2 | 1 | 3 | 1 | 1 | 3 | 1 |
|  | paraHipp |  |  |  |  |  |  |  | 3 |  |  |  |
|  | post. CC |  |  | 1 |  |  |  |  |  |  |  |  |
|  | raCC | 3 |  |  | 2 |  | 3 |  | 1 |  |  | 3 |
|  | Temporal | 4 | 6 | 6 | 7 | 10 | 19 | 22 | 17 | 13 | 19 | 22 |
|  | vlPFC | 1 | 1 |  | 6 | 9 | 12 | 4 | 12 | 1 | 4 | 4 |
| Right | Accumb. |  |  |  |  |  | 3 |  |  |  |  | 2 |
|  | Amyg. |  | 4 | 1 |  | 5 | 5 |  |  | 2 | 5 | 5 |
|  | Caudate |  |  | 1 |  | 8 | 6 |  |  |  |  | 6 |
|  | Hipp |  | 2 | 5 | 6 | 3 | 7 | 3 | 1 | 6 | 11 | 7 |
|  | dACC |  |  | 2 |  | 1 | 1 | 6 |  | 2 | 2 | 7 |
|  | dlPFC | 6 | 6 | 14 | 10 | 23 | 12 | 7 | 1 | 10 | 24 | 20 |
|  | dmPFC | 3 | 7 | 3 | 6 | 12 | 3 | 1 |  | 1 | 8 |  |
|  | Insula |  |  |  |  |  |  |  | 2 |  |  |  |
|  | lOFC | 3 | 5 | 3 | 4 | 8 | 8 | 2 | 13 | 3 | 10 | 7 |
|  | mOFC |  |  |  |  | 3 | 1 |  | 2 | 1 | 2 | 2 |
|  | paraHipp |  |  |  |  |  |  |  | 3 |  |  |  |
|  | post. CC | 1 |  |  |  |  |  |  |  |  |  |  |
|  | raCC | 3 |  |  | 2 | 1 |  |  | 1 | 1 |  | 3 |
|  | Temporal | 6 | 4 | 5 | 10 | 12 | 16 | 16 | 23 | 10 | 18 | 8 |
|  | vlPFC | 7 | 3 | 3 | 4 | 12 | 3 | 12 | 15 | 2 | 5 | 14 |
|  | Total | 61 | 69 | 64 | 83 | 150 | 141 | 139 | 147 | 120 | 162 | 189 |

FIG. 34

|  | MG | 85 | 86 | 88 | 89 | 90 | 96 | 99 | 101 | 102 | 104 | 106 | 107 |
|---|---|---|---|---|---|---|---|---|---|---|---|---|---|
| Left | Accumb. |  |  |  |  |  |  |  |  |  |  |  | 1 |
|  | Amyg. | 3 | 4 | 4 | 4 | 4 | 2 | 5 | 3 | 5 |  | 2 | 4 |
|  | Caudate |  |  |  |  |  | 7 | 3 | 10 | 2 | 7 |  | 5 |
|  | Hipp | 2 | 5 | 3 | 3 | 5 | 4 | 10 | 4 |  |  | 6 | 11 |
|  | dACC | 3 | 2 | 1 | 1 | 5 |  | 5 |  |  | 4 | 3 | 6 |
|  | dlPFC | 9 | 12 | 11 | 10 | 9 | 15 | 31 | 17 | 16 | 43 | 34 | 35 |
|  | dmPFC | 2 | 6 | 3 | 1 |  | 3 | 2 | 10 | 19 | 1 | 4 | 6 |
|  | Insula |  |  |  |  |  |  |  |  | 2 | 3 |  |  |
|  | lOFC | 1 | 4 | 4 |  | 2 | 8 | 7 | 10 | 8 | 8 | 4 | 8 |
|  | mOFC |  | 2 | 1 | 1 | 1 | 1 | 3 | 4 | 1 | 1 | 3 | 1 |
|  | paraHipp |  |  |  |  |  |  |  |  | 3 |  |  |  |
|  | post. CC |  |  | 2 | 1 |  |  |  |  |  |  |  |  |
|  | raCC | 1 |  | 1 |  | 2 | 3 |  |  |  |  |  | 3 |
|  | Temporal | 5 | 7 | 5 | 6 | 8 | 17 | 22 | 17 | 13 | 13 | 21 | 22 |
|  | vlPFC | 2 | 1 |  |  | 6 | 12 | 4 | 6 | 11 | 1 | 4 | 4 |
| Right | Accumb. |  |  |  |  |  |  |  |  |  |  |  | 2 |
|  | Amyg. | 2 | 2 | 3 | 1 |  | 5 |  |  |  | 2 | 5 | 5 |
|  | Caudate | 1 |  |  | 1 |  | 6 |  |  |  |  |  | 6 |
|  | Hipp | 3 | 3 | 2 | 5 | 6 | 7 | 3 |  | 1 | 6 | 11 | 7 |
|  | dACC | 2 |  |  | 2 |  | 1 | 6 | 1 |  | 2 | 2 | 7 |
|  | dlPFC | 6 | 6 | 9 | 14 | 10 | 12 | 7 | 2 | 1 | 10 | 22 | 20 |
|  | dmPFC | 3 | 7 | 5 | 3 | 6 | 4 | 1 | 10 |  | 1 | 8 |  |
|  | Insula |  |  |  |  |  |  |  |  | 2 |  |  |  |
|  | lOFC | 2 | 4 | 6 | 3 | 4 | 8 | 2 | 15 | 13 | 3 | 10 | 7 |
|  | mOFC | 1 |  | 1 |  |  | 1 |  |  | 4 | 2 | 1 | 1 | 2 |
|  | paraHipp |  |  |  |  |  |  |  |  | 3 |  |  |  |
|  | post. CC | 2 |  | 3 |  |  |  |  |  |  |  |  |  |
|  | raCC | 2 |  |  |  | 2 |  |  |  | 1 | 1 | 1 | 3 |
|  | Temporal | 8 | 4 | 7 | 5 | 10 | 14 | 16 |  | 21 | 10 | 17 | 8 |
|  | vlPFC | 5 | 2 |  | 3 | 4 | 3 | 12 | 8 | 15 | 2 | 5 | 13 |
|  | Total | 65 | 71 | 71 | 64 | 84 | 133 | 139 | 122 | 139 | 119 | 162 | 186 |

FIG. 35

SYSTEMS, METHODS AND MEDIA FOR DETECTING AND FACILITATING AN EFFORTFUL MENTAL TASK BY PROVIDING REAL-TIME DEEP BRAIN STIMULATION

CROSS-REFERENCE TO RELATED APPLICATIONS

This application is a U.S. National Stage of PCT Application No PCT/US2018/029268 filed on Apr. 25, 2018 which is based on, claims the benefit of, and claims priority to U.S. Provisional Application No. 62/489,703, filed Apr. 25, 2017, Each preceding application is hereby incorporated by reference herein in its entirety for all purposes.

STATEMENT REGARDING FEDERALLY SPONSORED RESEARCH

This invention was made with government support under W911NF-14-2-0045 granted by the Defense Advanced Research Projects Agency. The government has certain rights in the invention.

BACKGROUND

Although mental illness is the leading cause of disability worldwide, there has been little change to the overall mortality rate for mental disorders including Major Depressive Disorder (MDD) and Obsessive Compulsive Disorder (OCD). Recently, electrical brain stimulation has been proposed as an approach to treat illnesses such as MDD and OCD because it can directly modulate electrical connections underlying these illnesses. For example, deep brain stimulation (DBS), an invasive surgical therapy, showed promising results in early trials with severely treatment-refractory OCD and MDD patients. However, randomized clinical trials of DBS for MDD and OCD had mixed results, which may be due in part to the studies use of a single stimulation regime to patients with heterogeneous sets of symptoms and inability to directly determine whether the DBS affected a change to the electrical connections underlying the disease states.

While, brain stimulation during well-defined behavioral and mental states, such as during laboratory psychophysical tasks, has repeatedly improved mental functioning, identification of non-invasive electrophysiologic markers of depression have not yielded robust, replicable biomarkers, possibly because constructs such as "mood" are ill-defined.

The disappointments of past clinical trials may be due to a variety of factors. For example, the open loop nature of traditional DBS fails to address the dynamic nature of neuropsychiatric illness. As another example, stimulation was typically delivered via monopolar field delivery, which did not allow for accurate targeting of specific areas of the brain after implantation.

Symptoms of neuropsychiatric illness often flare and resolve over a wide range of temporal scales depending on the illness, ranging from minutes to days. Traditional open loop DBS delivers constant stimulation without regard to patient symptoms, and adjustments in stimulation parameters are only possible during infrequent clinical visits.

While a 'closed-loop' DBS system would theoretically deliver stimulation to modulate patient brain activity in real-time only when needed, and allow for remote adjustments of parameters, such as system has not been practical for many illnesses due to the difficulty of determining when stimulation would be effective due to the lack of reliable biomarkers of specific phenotypes exhibited by patients suffering with neuropsychiatric illness.

What little is known about potential biomarkers of neuropsychiatric illness has been derived from fMRI paradigms designed to expose specific differences in behavior and regional connectivity between healthy participants and neuropsychiatric patients. However, monitoring fMRI activity is not conducive to delivering closed-loop therapy for many reasons; most obviously, it is not portable and has poor temporal resolution.

For more than a decade research has focused on developing 'closed-loop' or 'adaptive' DBS systems to improve upon traditional open-loop DBS therapy. A closed-loop system could reduce latencies for therapy adjustments, and allow for therapies to be tailored based on patient needs. Recent demonstrations of closed loop DBS for Parkinson's disease and epilepsy are promising for the future of closed-loop DBS. However, these demonstrations were not fully implantable. Instead, they relied on data streaming to an external computer that detected state and streamed commands back to the stimulator accordingly.

Accordingly, new systems, methods, and media for detecting and facilitating an effortful mental task by providing real-time deep brain stimulation are desirable.

SUMMARY

In accordance with some embodiments of the disclosure subject matter, systems, methods, and media for detecting and facilitating an effortful mental task by providing real-time deep brain stimulation are provided.

In accordance with some embodiments of the disclosed subject matter, a system for detecting an effortful mental state and providing stimulation to facilitate performance of an associated effortful mental task is provided, the system comprising: A system for detecting an effortful mental state and providing stimulation to facilitate performance of an associated effortful mental task, the system comprising: a plurality of monitoring sensors, each of the plurality of monitoring sensors configured to capture signals indicative of neural activity from one or more regions of a subject's brain using one or more contacts; an implanted stimulator configured to provide stimulation to a region of the subject's brain adjacent to the implanted stimulator; and one or more hardware processors programmed to: receive a first set of neural data corresponding to neural signals recorded while the subject performed the effortful mental task, the first set of neural data including: a first subset of neural data from a first set of contacts associated with a first region of the subject's brain; and a second subset of neural data from a second set of contacts associated with a second region of the subject's brain; receive a second set of neural data corresponding to neural signals recorded while the subject did not perform the effortful mental task, the second set of neural data including: a third subset of neural data from the first set of contacts associated with the first region of the subject's brain; and a fourth subset of neural data from the second set of contacts associated with the second region of the subject's brain; calculate, based on the first subset of neural data and the second subset of neural data, a first value indicative of a correlation between activity in the first region of the subject's brain and activity in the second region of the subject brain; calculate, based on the third subset of neural data and the fourth subset of neural data, a second value indicative of a correlation between activity in the first region of the subject's brain and activity in the second region of the subject brain; provide a first plurality of values, including the first value, derived from the first neural data to a classification model as examples of a first class; provide a second plurality of values, including the second value, derived from the second neural data to the classification model as examples of a second class; train the classification model using the first plurality of values and the second plurality of values; receive a third set of neural data corresponding to neural signals recorded while the subject's mental state is unknown, the third set of neural data including: a fifth subset of neural data from the first set of contacts associated with the first region of the subject's brain; and a sixth subset of neural data from the second set of contacts associated with the second region of the subject's brain; calculate, based on the fifth subset of neural data and the sixth subset of neural data, a third value indicative of a correlation between activity in the first region of the subject's brain and activity in the second region of the subject brain; provide a third plurality of values, including the third value, derived from the third neural data to the trained classification model as input to be classified; receive, from the trained classification model, an output indicative of whether the third neural data is a member of the first class or the second class; determine, based on the output, that the third neural data is a member of the first class indicating that the subject is experiencing the effortful mental state; and in response to determining that the subject is experiencing the effortful mental state, cause the implanted stimulator to provide stimulation to the region of the subject's brain adjacent to the implanted stimulator to augment the subject's brain function.

In some embodiments, the one or more hardware processors are further programmed to: calculate the first value based on a canonical correlation analysis using the first subset of neural data as a first input and the second set of neural data as a second input.

In some embodiments, the one or more hardware processors are further programmed to: calculate the first value based on a fixed canonical correlation analysis using the first subset of neural data as a first input and the second set of neural data as a second input.

In some embodiments, a first monitoring sensor of the plurality of monitoring sensors comprises a depth electrode implanted into the first region of the subject's brain, the depth electrode comprising a plurality of contacts.

In some embodiments, a first monitoring sensor of the plurality of monitoring sensors comprises an intracranial electrode positioned to generate electrocorticography signals based on signals from first region of the subject's brain.

In some embodiments, a first monitoring sensor of the plurality of monitoring sensors comprises a scalp electrode positioned to generate electroencephalography signals based on signals from first region of the subject's brain.

In some embodiments, the classification model is a support vector machine-based classification model.

In some embodiments, the first subset of neural data and the second subset of neural data comprises neural data from a window of time.

In some embodiments, the window is one to ten seconds.

In some embodiments, the window is four to five seconds.

In some embodiments, the first subset of neural data and the second subset of neural data comprises neural data from a window of time.

In some embodiments, the effortful mental state is a state of heightened cognitive interference.

In some embodiments, the effortful mental state is a state of heightened emotional conflict.

In some embodiments, comprising an implanted pulse generator comprising a hardware processor of the one or more hardware processors.

In some embodiments, the first subset of neural data from the first set of contacts is organized as a matrix $$X = \begin{bmatrix} X_{1,1} & \ldots & X_{1,t} \\ \vdots & \ddots & \vdots \\ X_{n,1} & \ldots & X_{n,t} \end{bmatrix},$$

where n is a number of channels represented by the first set of contacts and t is the number of samples in a window of time during which the first subset of neural data was recorded, and the second subset of neural data from the second set of contacts is organized as a matrix $$Y = \begin{bmatrix} Y_{1,1} & \ldots & Y_{1,t} \\ \vdots & \ddots & \vdots \\ Y_{n,1} & \ldots & Y_{n,t} \end{bmatrix},$$

where n is the number of channels represented by the second set of contacts and t is the number of samples in a window of time during which the second subset of neural data was recorded.

In some embodiments, the first set of contacts consists of n contacts, and the second set of contacts consists of n contacts that are a subset of m contacts associated with the second region of the subject's brain, where m is greater than n.

In some embodiments, the first set of neural data includes n subsets of neural data, each corresponding to a different region of the subjects brain including the first subset of neural data and the second subset of neural data, and the one or more hardware processors are further programmed to: calculate a value indicative of a correlation between each combination of two subsets of the n subsets such that at least n!/(n−2)!2! values are calculated, wherein each value is a probability of the two subsets of neural data being correlated.

In some embodiments, n is greater than two.

In some embodiments, wherein n is two to ten.

In some embodiments, the system further comprises a second implanted stimulator configured to provide stimulation to a region of the subject's brain adjacent to the implanted stimulator.

In some embodiments, the plurality of monitoring sensors comprise at least one of a near-infrared optical sensor, an optical detector configured to detect fluorescence, a magnetometers, an ultrasonic detector, and a nano-mechanical receiver, and wherein the implanted stimulator is configured to stimulate the region of the subject's brain adjacent to the implanted stimulator is configured to stimulate the subject's brain using at least one of electrical stimulation, magnetic stimulation, optical stimulation, and sonic stimulation.

In accordance with some embodiments of the disclosed subject matter, a system for detecting an effortful mental state and providing stimulation to augment brain function during the effortful mental state is provided, the system comprising: a plurality of monitoring electrodes each configured to record activity from one or more regions of a subject's brain; an implanted electrode configured to provide deep brain stimulation to the subject's brain; and one or more hardware processors programmed to: receive first neural data corresponding to activity in a first region of the subject's brain during performance of a task that causes the effortful mental state; receive second neural data corresponding to activity in a second region of the subject's brain during performance of the task that causes the effortful mental state; receive third neural data corresponding to activity in the first region of the subject's brain during a non-task period; receive fourth neural data corresponding to activity in the second region of the subject's brain during the non-task period; train a classification model using correlations between the first neural data and the second neural data as task data, and correlations between the third neural data and the fourth neural data as non-task data; receive neural data corresponding to activity in the first region of the subject's brain and the second region of the subject's brain during a period subsequent to training the classification model; provide, as inputs to the classification model, correlations between activity in the first region and the second region during the period subsequent to training the classification model; receive, from the classification model, an output indicating the likelihood that the subject is performing a task that causes the effortful mental state; and causing, using the implanted electrode, deep brain stimulation to be provided based on the output.

In accordance with some embodiments of the disclosed subject matter, a method for detecting an effortful mental state and providing stimulation to facilitate performance of an associated effortful mental task is provided, the method comprising: receiving, from a plurality of electrodes each comprising at least one contact, a first set of neural data corresponding to neural signals recorded while the subject performed the effortful mental task, the first set of neural data including: a first subset of neural data from a first set of contacts associated with a first region of the subject's brain; and a second subset of neural data from a second set of contacts associated with a second region of the subject's brain; receiving, from the plurality of electrodes, a second set of neural data corresponding to neural signals recorded while the subject did not perform the effortful mental task, the second set of neural data including: a third subset of neural data from the first set of contacts associated with the first region of the subject's brain; and a fourth subset of neural data from the second set of contacts associated with the second region of the subject's brain; calculating, based on the first subset of neural data and the second subset of neural data, a first value indicative of a correlation between activity in the first region of the subject's brain and activity in the second region of the subject brain; calculating, based on the third subset of neural data and the fourth subset of neural data, a second value indicative of a correlation between activity in the first region of the subject's brain and activity in the second region of the subject brain; providing a first plurality of values, including the first value, derived from the first neural data to a classification model as examples of a first class; providing a second plurality of values, including the second value, derived from the second neural data to the classification model as examples of a second class; training the classification model using the first plurality of values and the second plurality of values; receiving, from the plurality of electrodes, a third set of neural data corresponding to neural signals recorded while the subject's mental state is unknown, the third set of neural data including: a fifth subset of neural data from the first set of contacts associated with the first region of the subject's brain; and a sixth subset of neural data from the second set of contacts associated with the second region of the subject's brain; calculating, based on the fifth subset of neural data and the sixth subset of neural data, a third value indicative of a correlation between activity in the first region of the subject's brain and activity in the second region of the subject brain; providing the third plurality of values, including the third value, derived from the third neural data to the trained classification model as input to be classified; receiving, from the trained classification model, an output indicative of whether the third neural data is a member of the first class or the second class; determining, based on the output, that the third neural data is a member of the first class indicating that the subject is experiencing the effortful mental state; and in response to determining that the subject is experiencing the effortful mental state, causing an implanted electrode to provide electrical stimulation to a region of the subject's brain adjacent to the implanted electrode to augment the subject's brain function.

In accordance with some embodiments of the disclosed subject matter, a non-transitory computer readable medium containing computer executable instructions that, when executed by a processor, cause the processor to perform a method for detecting an effortful mental state and providing stimulation to facilitate performance of an associated effortful mental task is provided, the method comprising: receiving, from a plurality of electrodes each comprising at least one contact, a first set of neural data corresponding to neural signals recorded while the subject performed the effortful mental task, the first set of neural data including: a first subset of neural data from a first set of contacts associated with a first region of the subject's brain; and a second subset of neural data from a second set of contacts associated with a second region of the subject's brain; receiving, from the plurality of electrodes, a second set of neural data corresponding to neural signals recorded while the subject did not perform the effortful mental task, the second set of neural data including: a third subset of neural data from the first set of contacts associated with the first region of the subject's brain; and a fourth subset of neural data from the second set of contacts associated with the second region of the subject's brain; calculating, based on the first subset of neural data and the second subset of neural data, a first value indicative of a correlation between activity in the first region of the subject's brain and activity in the second region of the subject brain; calculating, based on the third subset of neural data and the fourth subset of neural data, a second value indicative of a correlation between activity in the first region of the subject's brain and activity in the second region of the subject brain; providing a first plurality of values, including the first value, derived from the first neural data to a classification model as examples of a first class; providing a second plurality of values, including the second value, derived from the second neural data to the classification model as examples of a second class; training the classification model using the first plurality of values and the second plurality of values; receiving, from the plurality of electrodes, a third set of neural data corresponding to neural signals recorded while the subject's mental state is unknown, the third set of neural data including: a fifth subset of neural data from the first set of contacts associated with the first region of the subject's brain; and a sixth subset of neural data from the second set of contacts associated with the second region of the subject's brain; calculating, based on the fifth subset of neural data and the sixth subset of neural data, a third value indicative of a correlation between activity in the first region of the subject's brain and activity in the second region of the subject brain; providing the third plurality of values, including the third value, derived from the third neural data to the trained classification model as input to be classified; receiving, from the trained classification model, an output indicative of whether the third neural data is a member of the first class or the second class; determining, based on the output, that the third neural data is a member of the first class indicating that the subject is experiencing the effortful mental state; and in response to determining that the subject is experiencing the effortful mental state, causing an implanted electrode to provide electrical stimulation to a region of the subject's brain adjacent to the implanted electrode to augment the subject's brain function.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 8 shows an example of a process for selecting features to use when training a classification model in accordance with some embodiments of the disclosed subject matter.

FIG. 30 shows, for each subject, the number of sessions of each test during which data was collected, the number of Neural Signal Processors (NSPs) recording systems used to collect the data, and the number of electrodes used to collect data from each hemisphere of the brain.

FIG. 34 shows an example of a bipolar electrode localization table for various subjects that performed the MSIT task.

FIG. 35 shows an example of a bipolar electrode localization table for various subjects that performed the ECR task.

DETAILED DESCRIPTION

Figure 1:
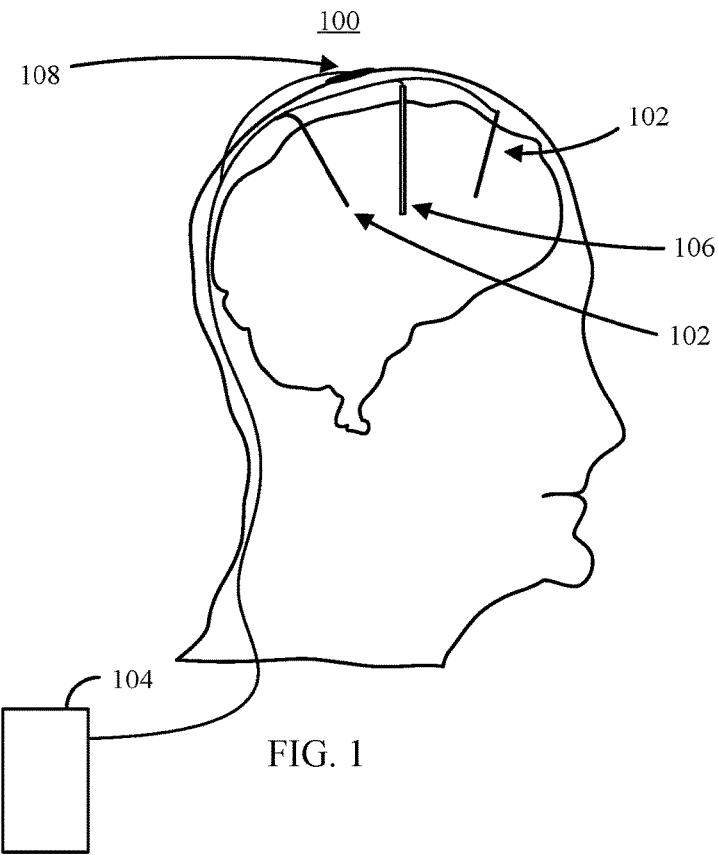
FIG. 1 shows an example of a system including monitoring electrodes, a reference electrode, and a pulse generator for detecting an effortful mental state indicative of performance of an effortful mental task, and a deep brain stimulation lead for facilitating the effortful mental task by providing real-time deep brain stimulation to enhance performance in accordance with some embodiments of the disclosed subject matter.

In accordance with various embodiments, mechanisms (which can, for example, include systems, methods, and media) detecting an effortful mental state and providing real-time deep brain stimulation to enhance performance of effortful mental tasks are provided.

The brain is a distributed network that operates at small and large spatial and temporal scales to meet the needs of the task at hand. Certain mental tasks (e.g., tasks related to making a decision or processing emotions, as opposed to neural activity related to motor intention or effortful physical movement) generate conflict by requiring attention to relevant stimuli among distractions. Engagement in conflict-based tasks elicits network activity that can be used to differentiate these tasks from other behavior. Brain states associated with conflict in experimental behavioral contexts may be an important marker of dysfunction related to neuropsychiatric illness, yet there are no documented decoders that predict engagement in conflict-based tasks through invasive, large scale local field potential recordings. Additionally, there is evidence that precisely timed DBS can restore normal behavioral task dynamics in neuropsychiatric patients.

Regions of the brain perform distinct, separable functions, and the flow of information among the network is coordinated by modulating the strength, pattern, and frequency of neural activity. Specific patterns of synchrony between individual neurons, populations of neurons, or entire brain regions are associated with complex behaviors, such as attention and conflict resolution. In other words, brain regions are functionally connected. Observing and quantifying functional connectivity between regions of interest during different tasks is an example of a strategy for gaining insight on the link between neural activity and behavior. Observing functional connectivity during task-based imaging studies has greatly contributed to relating brain states to abnormal behavior observed during neuropsychiatric illness. In particular, abnormalities in the anterior cingulate cortex (ACC) have been observed in the pathophysiology of neuropsychiatric illness, including attention deficit disorder (ADD), anxiety disorders, OCD, and PTSD. Based on many single unit recording studies in nonhuman primate literature, it is known that the dorsal anterior cingulate cortex (dACC) is not a homogenous region and instead is composed of distinct cognitive, emotional, and motor subdivisions. Hinging on implications of ACC activity for neuropsychiatric illness, tasks have been developed to reliably activate each distinct subdivision to better relate neural activity to behavior.

A particularly useful state for intervention is effortful decision-making, as it is highly relevant to mental illness, accessible via electrophysiology, and responsive to intervention. Decisional conflict is typically generated during mental tasks that require the brain to attend to relevant stimuli among distractions and decide on the best option amid uncertainty. During this process, patterns of activity between individual neurons, populations of neurons, and entire brain regions coordinate to enable complex behaviors (e.g. cognition, attention, conflict resolution) required to make decisions and meet the needs of the task. Dysfunctional responses to decisional conflict are common across mental disorders. They may manifest as perseverative incorrect responses, slowed reaction times, and/or impulsive errors. In some cases, patients appear behaviorally normal, but show marked abnormal neural responses suggesting that their decision-making circuits are unusually taxed by conflict. Stimulation applied during decisional conflict can bias decisions and behaviors to ameliorate dysfunctional responses.

There are specific tasks for measuring conflict in laboratory settings. For example, the Multi-Source Interference Task (MSIT) and the Emotional Conflict Resolution (ECR) task have been designed to reliably and robustly activate networks associated with cognitive and emotional conflict, respectively. The ECR task exposes functional connectivity differences between neuropsychiatric participants and healthy controls that may have implications for mood and anxiety disorders. Generalized Anxiety Disorder (GAD) patients have been found to be unable to regulate emotional conflict during the ECR task as compared to healthy controls. Likewise, the MSIT task exposes functional connectivity differences between MDD participants and OCD participants relative to healthy controls. The changes in brain networks that occur during engagement in specific effortful mental efforts suggest that it may be possible to identify when a participant is trying to complete a mental task but failing. If this mental state is detected, an intervention, such as DBS, can be applied to augment the brain's function during that specific effort.

Functional connectivity differences between neuropsychiatric patients and healthy controls have been identified during the MSIT task, although no significant differences in task performance have been found. For example, patients with MDD exhibit decreased connectivity between the subgenual ACC and the vlPFC, and between the subgenual ACC and ventral striatum relative to healthy controls. ADHD patients treated with stimulant medications have been found to exhibit increased dACC activation during the task relative to no stimulant medication. OCD patients have been found to exhibit greater supplementary motor area (SMA) activation and greater rostral anterior cingulate cortex (rACC) deactivation during interference trials, along with hyperactivation of the dACC and insular cortices.

Separate from the ECR task, findings from many studies support the notion that rostral cingulate inhibition of the amygdala is important for resolving emotional conflict. PTSD patients show a hypoactive rostral cingulate during the recollection of trauma and the severity of symptoms correlates with the degree of rostral cingulate hypoactivation. The hypo activity of the rostral cingulate cortex is also related to refractory depression51 and predicts a poor response to antidepressant medications.

Quantifying functional connectivity poses challenges for researchers, who are tasked with choosing a meaningful metric and interpreting results. Many metrics have been developed, each with its own advantages and limitations. Canonical correlation analysis (CCA) can be a robust tool for detecting connectivity between predefined regions of interest. During CCA, individual sensors can be grouped into pre-defined anatomical regions of interest. Variability within individual regions can be assessed through singular value decompositions on all the sensors grouped to each region. Then, the resulting singular vectors can be transformed in a way that maximally correlates activity between each region pair. This can both reduce the dimensionality of the network from individual sensors to regions of interest, and successfully estimates spatial correlation between regions of interest.

Latency between state onset and delivery of therapy is an important consideration for closed-loop performance, and may depend on the application in which it is being considered. For example, brain states associated with cursor control are transient and require immediate action on timescales less than one second. However, brain states associated with neuropsychiatric illness might wax and wane over minutes (e.g., in the cases of anxiety, PTSD) to days (e.g., in the cases of bipolar disorder, depression).

Engaging in effortful mental action, such as trying to decide between conflicting choices or attempting to suppress an unwanted emotion, activates specific brain networks. This activity can be used to differentiate one behavior from another. Detecting these specific brain states may make it possible to identify when a patient is trying to do a critical mental task, but failing, and an intervention, such as DBS can be applied to augment the brain's function during that specific effort.

In accordance with some embodiments of the disclosed subject matter, the mechanisms described herein can train a classification model, such as a Support Vector Machine, using labeled neural data recorded from various regions of interest in a subject's brain while the subject is performing a specific type of task, and when the subject is not performing the specific type of task. In accordance with some embodiments, correlations between the signals in pairs of regions of interest can be used as features that are provided to the classification model, which can be extracted from the data using CCA-based techniques.

In accordance with some embodiments, the mechanisms described herein can provide features based on correlations between regions of interest to the trained classification model during a period of time when it is unknown whether the subject is performing the specific type of task. In accordance with some embodiments, the mechanisms described herein can provide stimulation to assist a subject in successfully performing the specific type of task when the classification model indicates that the subject is performing the specific type of task.

FIG. 1 shows an example 100 of a system including monitoring electrodes 102, a reference electrode 108, and a pulse generator 104 for detecting an effortful mental state indicative of performance of an effortful mental task, and a deep brain stimulation lead 106 for facilitating the effortful mental task by providing real-time deep brain stimulation to enhance performance in accordance with some embodiments of the disclosed subject matter. As shown in FIG. 1, system 100 can include monitoring electrodes 102 that are implanted in various regions of interest within the brain and configured to capture local field potentials (LFP).

In some embodiments, monitoring electrodes 102 can be implemented using depth electrodes configured to sense activity in different portions of the brain along the length of the electrode (e.g., depth electrodes available from Ad-Tech Medical Instrument Corp. of Oak Creek, Wis.). Additionally or alternatively, in some embodiments, commercially available DBS probes (e.g., DBS probes available from Medtronic, Inc. of Minneapolis, Minn.) can be used to monitor neural activity and/or provide electrical stimulation. In some embodiments, one or more monitoring electrodes 102 can be positioned to monitor one or more regions of interest in the subject's brain. Additionally or alternatively, monitoring electrodes 102 may already be positioned to monitor one or more regions of the subject's brain (e.g., monitoring electrodes may have been previously implanted to identify seizure foci. In some embodiments, whether monitoring electrodes 102 are positioned in anticipation of utilizing the mechanisms described herein or were previously positioned for another purpose, regions of the brain from which each monitoring electrode 102 is likely to receive signals can be determined using an electrode localization algorithm (ELA) in conjunction with MRI and/or CT scans. For example, images from the MRI scan can be used to determine locations of the anatomical regions with the brain, while images from the CT scan can be used to determine locations of the implanted electrodes within the brain. In such an example, the ELA can be used to provide a probability that each monitoring electrode 102 will receive signals from particular anatomical regions of the brain based on the physical relationship between voxels corresponding to each anatomical region in the structural MRI and the location of the electrode. As described in more detail below in connection with FIG. 14, to calculate a probability, the number of voxels corresponding to each anatomical region within a threshold distance of each electrode voxel can be counted, and a matrix including a probability that a given electrode will obtain a signal from a given anatomical region can be generated based on the counts.

In some embodiments, reference electrode 108 can be placed on the surface of the subject's scalp to generate a reference signal that can be used to monitoring electrodes 102. In some embodiments, the reference electrode can be placed on any number of anatomical features of the subject. In some embodiments, reference electrode 108 can be biased using any of various suitable DC or AC voltages.

In some embodiments, pulse generator 104 can be electrically connected to implanted DBS lead(s) 106, monitoring electrodes 102, and/or reference electrode(s) 108. In some embodiments, connections from DBS lead(s) 106 and/or monitoring electrodes 102 to pulse generator 104 can be established via wires implanted under the subject's skin via a percutaneous procedure. In some embodiments, pulse generator 104 can implanted into the subject. Alternatively, in some embodiments, pulse generator 104 can be external to the subject. In some embodiments, DBS lead(s) 106 and/or monitoring electrodes 102 can be implanted to monitor and/or provide electrical stimulation to one more brain region(s), such as, the dorsolateral prefrontal cortex, the dorsomedial prefrontal cortex, the orbitofrontal cortex, the ventrolateral prefrontal cortex, the cingulate cortex, the temporal lobe, the insula, the hippocampus, the caudate nucleus, the amygdala, the internal capsule, and/or the ventral striatum. In some embodiments, DBS lead(s) 106 can be omitted when monitoring electrodes 102 can be configured to provide electrical stimulation to a specific region(s) of the brain. For example, depth electrodes can be configured to both record neural signals, and provide stimulation. In some embodiments, DBS lead(s) 106 can be configured to record neural signals (e.g., as described above in connection with monitoring electrodes 102).

In some embodiments, monitoring electrodes 102 can be used to implement a unipolar recording scheme. In such a unipolar recording scheme, the data can be extracted by subtracting a signal received from a particular monitoring electrode 102 from the reference signal generated by the reference electrode.

In some embodiments, monitoring electrodes 102 can used to implement a bipolar recording scheme. In such a bipolar recording scheme, the data can be extracted by subtracting the signal from one unipolar electrode from the signal from a second unipolar electrode, and the signal from each unipolar electrode can represent the difference between the signal generated by an area of the brain around the electrode and the signal generated by the reference electrode.

Note that, although monitoring electrodes 102 are generally described herein as being implanted depth electrodes, this is merely an example, and monitoring electrodes 102 can be implemented using other types of electrodes. For example, in some embodiments of the disclosed subject matter, monitoring electrodes 102 can be implemented using noninvasive electrodes, such as surface electrodes (pads) that are placed on the scalp of a subject and mapped to specific anatomical structures of the brain. In a more particular example, monitoring electrodes 102 can be used to provide signals for an Electroencephalography (EEG) or any other electrophysiological monitoring system. In some embodiments, monitoring electrodes 102 and/or DBS lead(s) 106 can be implanted for a fixed period of time (e.g., a particular treatment period), a variable length of time, or an indefinite period of time (e.g., permanently).

Figure 2:
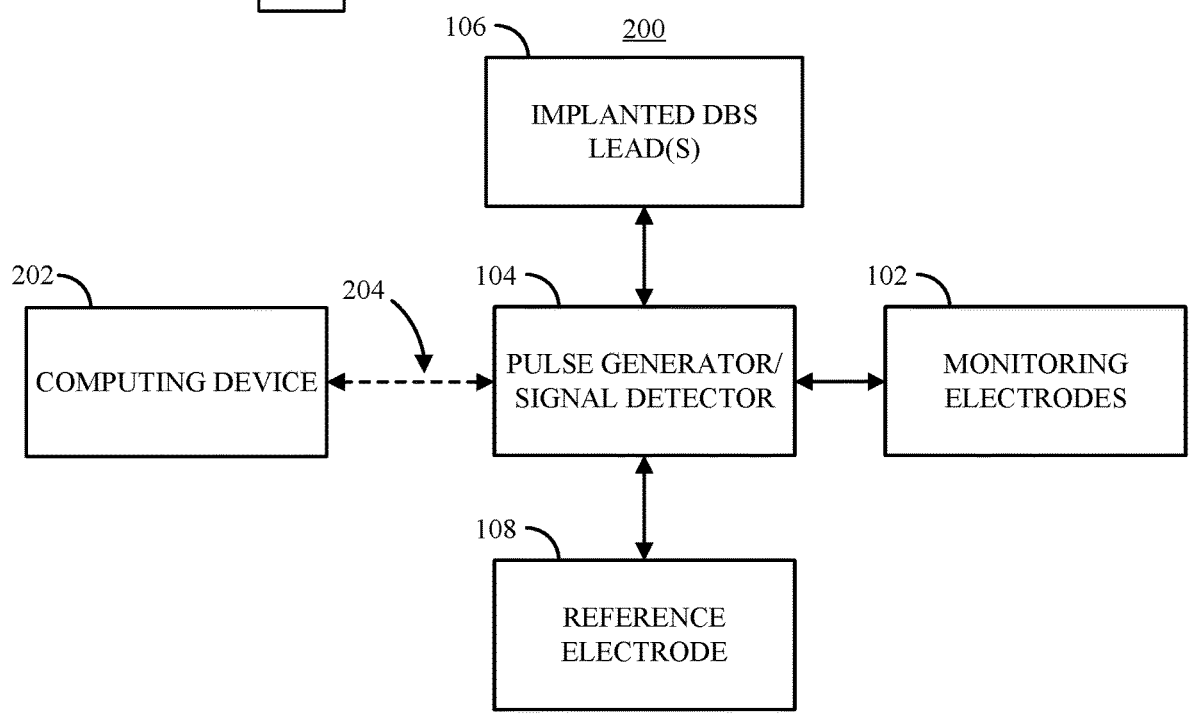
FIG. 2 shows an example of a system for detecting and facilitating an effortful mental task by providing real-time deep brain stimulation in accordance with some embodiments of the disclosed subject matter.

FIG. 2 shows an example 200 of a system for detecting and facilitating an effortful mental task by providing real-time deep brain stimulation in accordance with some embodiments of the disclosed subject matter. In some embodiments, a computing device 202 can be communicate with pulse generator 104 by a communication link 204 using any suitable technique or combination of techniques. As shown in FIG. 2, pulse generator 104 can be electrically coupled to monitoring electrodes 102, implanted leads(s) 106, and/or reference electrode 108. In some embodiments, pulse generator 104 can receive instructions (e.g., updated software and/or firmware, instructions to begin or suspend operation, etc.) from computing device via communication link 204, can provide data (e.g., neural signals received from monitoring electrodes 102) to computing device via communication link 204, etc.

Figure 3:
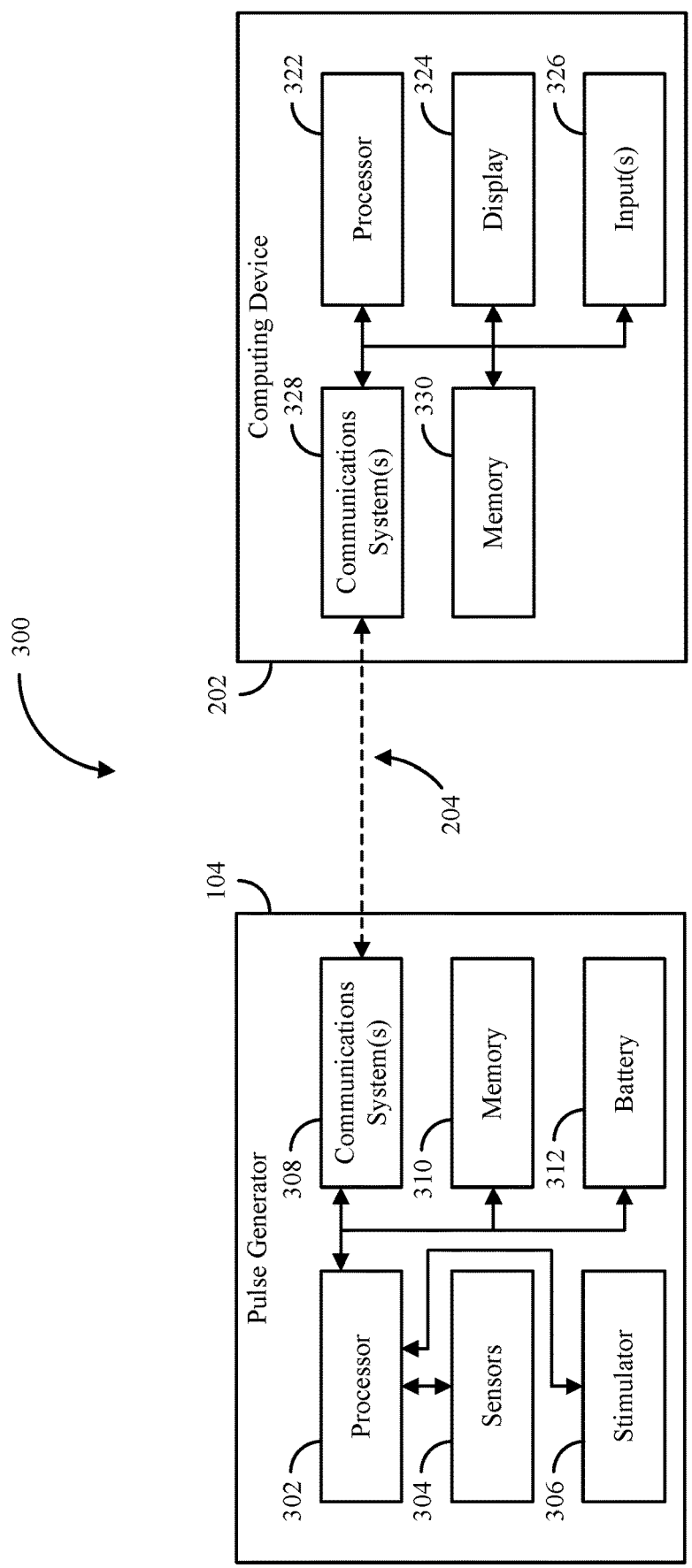
FIG. 3 shows an example of hardware that can be used to implement a pulse generator and computing device in accordance with some embodiments of the disclosed subject matter.

FIG. 3 shows an example 300 of hardware that can be used to implement pulse generator 104 and computing device 202 in accordance with some embodiments of the disclosed subject matter. As shown in FIG. 3, in some embodiments, pulse generator 104 can include a processor 302, sensor hardware 304 that is configured to be electrically connected to, and/or receive signals from, one or more sensors (e.g., monitoring electrodes 102), stimulation hardware 306 that is configured to be electrically connected to, and/or receive signals from, one or more neurostimulation leads (e.g., implanted DBS lead 106), one or more communication systems 308, memory 310, and/or a battery (and/or other power source) 312.

In some embodiments, processor 302 can be any suitable hardware processor or combination of processors, such as a central processing unit (CPU), a graphics processing unit (GPU), etc. In some embodiments, communications system(s) 308 can include any suitable hardware, firmware, and/or software for communicating information to computing device 202, over communication link 204, over any other suitable communication link or combination of communication links, and/or over any suitable communication network or combination of networks. For example, communications system(s) 308 can include one or more transceivers, one or more communication chips and/or chip sets, etc. In a more particular example, communications system(s) 308 can include hardware, firmware and/or software that can be used to communicate data over a coaxial cable, a fiber optic cable, an Ethernet connection, a USB connection, to establish a Wi-Fi connection, a Bluetooth connection, a cellular connection, etc.

In some embodiments, memory 310 can include any suitable storage device or devices that can be used to store instructions, values, etc., that can be used, for example, by processor 302 to control operation of stimulator 306, to communicate with computing device 202 via communications system(s) 308, etc. Memory 310 can include any suitable volatile memory, non-volatile memory, storage, or any suitable combination thereof. For example, memory 310 can include RAM, ROM, EEPROM, one or more flash drives, one or more hard disks, one or more solid state drives, one or more optical drives, etc. In some embodiments, memory 310 can have encoded thereon a computer program for controlling operation of processor 302 to record neural signals indicative of activity in various regions of the brain from monitoring electrodes 102, determining correlation parameters by executing a canonical correlation analysis (CCA) and/or Fixed Canonical Coherence analysis (FCCA) to evaluate the recorded neural data, training a classification model (e.g. a Support Vector Machine) to classify received neural data as corresponding to an effortful mental state using calculated correlation parameters and corresponding labels, providing signals to a trained classification model, receiving an output from a trained classification model indicative of a subject's mental state, causing stimulation to be provided when the classification model indicates that the subject is experiencing an effortful mental state, etc. framework to evaluate the data, and training a classifier (e.g. a Support Vector Machine) to classify received neural data as corresponding to an effortful mental state using calculated correlation parameters and corresponding labels. In some such embodiments, processor 302 can execute at least a portion of the computer program to receive signals via monitoring electrodes 102, to execute at least a portion of process 400 and/or process 500 as described below in connection with FIGS. 4 and 5.

In some embodiments, computing device 202 can include a processor 332, a display 324, one or more inputs 326, one or more communication system(s) 328, and/or memory 330. In some embodiments, processor 322 can be any suitable hardware processor or combination of processors, such as a CPU, a GPU, etc. In some embodiments, display 324 can include any suitable display devices, such as a computer monitor, a touchscreen, a television, etc. In some embodiments, inputs 326 can include any suitable input devices and/or sensors that can be used to receive user input, such as a keyboard, a mouse, a touchscreen, a microphone, etc.

In some embodiments, communications system(s) 328 can include any suitable hardware, firmware, and/or software for communicating with pulse generator 104, for communicating information over communication link 204, and/or for communicating over any other suitable communication networks. For example, communications system(s) 328 can include one or more transceivers, one or more communication chips and/or chip sets, etc. In a more particular example, communications systems 328 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 330 can include any suitable storage device or devices that can be used to store instructions, values, etc., that can be used, for example, by processor 322 to present content using display 324, to communicate with one or more pulse generators (e.g., pulse generator 104). Memory 330 can include any suitable volatile memory, non-volatile memory, storage, or any suitable combination thereof. For example, memory 330 can include RAM, ROM, EEPROM, one or more flash drives, one or more hard disks, one or more solid state drives, one or more optical drives, etc. In some embodiments, memory 330 can have encoded thereon a computer program for controlling operation of processor 322. In some such embodiments, processor 322 can execute at least a portion of the computer program to receive neural data indicative of activity in various regions of the brain from pulse generator 104, to label data (e.g., as being task or non-task data) using input(s) 326 and/or using any other suitable techniques, determining correlation parameters by executing a CCA and/or FCCA framework to evaluate the recorded neural data, training a classification model (e.g. a Support Vector Machine) to classify received neural data as corresponding to an effortful mental state using calculated correlation parameters and corresponding labels, providing signals to a trained classification model, receiving an output from a trained classification model indicative of a subject's mental state, causing stimulation to be provided when the classification model indicates that the subject is experiencing an effortful mental state, etc. Additionally or alternatively, in some embodiments, labeled signals can be used to train a convolutional neural network (CNN) to classify neural data as corresponding to an effortful mental state. In some embodiments, processor 322 can execute one or more portions of process 400 and/or process 500. In some embodiments, computing device 202 can be any suitable computing device or combination of computing devices, such as a personal computer, a laptop computer, a tablet computer, a smartphone, a wearable computer, a server, etc.

Although not shown, in some embodiments, communication link 204 can be multiple communication links that form a portion of any suitable communication network or combination of communication networks. For example, communication link 204 can be a combination of one or more links in a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc.

Figure 4:
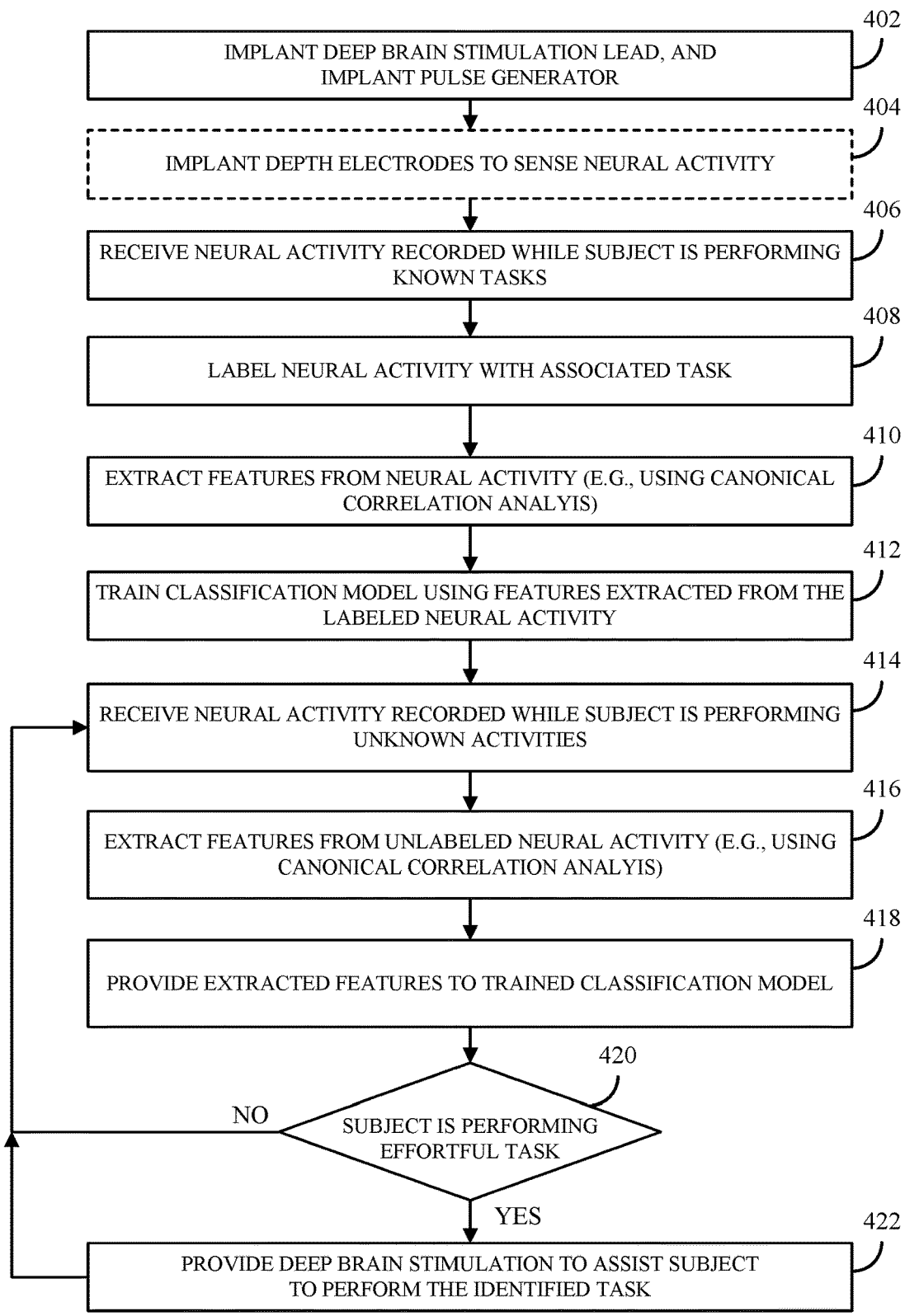
FIG. 4 shows an example of a process for detecting and facilitating an effortful mental task by providing real-time deep brain stimulation in accordance with some embodiments of the disclosed subject matter.

FIG. 4 shows an example 400 of a process for detecting and facilitating an effortful mental task by providing real-time deep brain stimulation in accordance with some embodiments of the disclosed subject matter. At 402, process 400 can include implanting a deep brain stimulation lead (e.g., deep brain stimulation lead 106 of FIG. 1), which can include forming an electrical connection between the deep brain stimulation lead and a pulse generator (e.g., pulse generator 104 described above in connection with FIGS. 1-3), which can be implanted within the subject or can be external to the subject.

At 404, process 400 can include implanting monitoring electrodes (e.g., monitoring electrodes 102 of FIG. 1) into specific anatomical regions of the subject's brain. In some embodiments, monitoring electrodes can be any suitable type of monitoring electrode, such as electrocorticography (ECoG) electrodes, which can be placed on the subject's brain tissue after a portion of the skull has been removed to expose the underlying brain tissue. In some embodiments, depth electrodes can be implanted by drilling a burr hole in the skull and inserting the electrodes through the burr hole. In some embodiments, monitoring electrodes (e.g., monitoring electrodes 102 of FIG. 1) can be implemented as subdural electrodes or stereotaxic depth electrodes.

Additionally or alternatively, in some embodiments, monitoring electrodes can be positioned on the surface of the scalp such that monitoring electrodes 102 receive signals from specific anatomical regions of the brain.

In some embodiments, monitoring electrodes 102 may have been previously implanted prior to initiation process 400. In some such embodiments, in addition to, or as an alternative to implanting electrodes at 404, an ELA can be used (e.g., in connection with an MRI and CT scan) to determine the areas of the brain from which the previously implanted electrodes are likely to receive signals. For example, a CT image can show the coordinates of the monitoring electrodes 102 with in the brain of the subject, and an MRI image can be used to label portions of the brain anatomy of the subject. The ELA can be used to calculate the probability that each electrode receives a signal from a particular anatomical region of the brain, as described in more detail below in connection with FIG. 14.

At 406, process 400 can receive signals indicative of neural activity recorded while the subject is performing a known task. In some embodiments, process 400 can receive the signals from any suitable source, such as monitoring electrodes (e.g., monitoring electrodes 102) implanted into a subjects brain. In some embodiments, the known task can be an MSIT task, which is intended to maximize cognitive interference. Additionally or alternatively, in some embodiments, the known task can be an ECR task, which is intended to cause emotional conflict. In some embodiments, the known task can be any suitable task that causes a subject to experience an effortful mental state. Examples of procedures for administering MSIT and ECR are described below in connection with FIG. 15.

At 408, process 400 can include labeling portions of the data with identifiers indicating whether that portion corresponds to when the subject was performing a known task (e.g., MSIT or ECT, sometimes referred to as "task") or when the subject was not performing a known task (sometimes referred to as "non-task"). In some embodiments, any suitable technique can be used to label the data with task and non-task identifiers. For example, a user may manually label data based on when the task was, and was not, being performed. In some embodiments, the data can be automatically labeled based on identifiers, such as time stamps, associated with administration of the task. For example, the time stamps can be based on an input provided by a user or the subject indicating when the subject is beginning, pausing, resuming, and/or ending the task. As another example, the time stamps can be based on a determination of a computing device being used to administer the task whether the subject is currently performing the task. In some embodiments, a signal can be communicated to the pulse generator (e.g. from computing device 202) indicating when the task is being performed or not being performed, and the pulse generator can label the received signals without user intervention. Additionally, in some embodiments, a buffer (e.g., a four second or five second buffer) can be added at the start and end of a "task" periods allowing for ramp-up and ramp-down periods. Additionally or alternatively, in some embodiments, "non-task'" labels can be assigned to time periods during which the subject is taking a break from the known task.

In some embodiments, process 400 can include subdividing the labeled task and non-task data into smaller portions (e.g., four second windows, five second windows, 10 second windows, etc.). In some embodiments, a portion of the data can be labeled as "task" during periods in which the subject has been instructed to engage in a task (e.g., during image presentation and fixation periods of the MSIT task and/or ECR task). In some embodiments, "non-task" labels can be assigned to portions of the data collected immediately before and after task engagement.

At 410, process 400 can include extracting features from neural activity data. In some embodiments, features can be extracted using CCA. Additionally or alternatively, features can be extracted using FCCA. CCA and/or FCCA can be used to estimate functional connectivity between brain regions over time. For example, as described below, CCA and/or FCCA can determine the amount of correlation based on matrices representing signals received from multiple electrodes in pairs of regions of interest. CCA does not rely on averaging signals from all electrodes in a particular region of interest, which may decrease the signal to noise ratio (e.g., due to destructive interference from two signals in the same region of interest that are out of phase). This can facilitate identification of neural markers of task engagement, can improve detectability of weak correlations between many nodes, and can facilitate comparisons between CCA features derived from other functional connectivity metrics, such as invasive neural data. Additionally, CCA can facilitate the application of a fixed projection space across all observations, which can be used to compare feature estimations over time. For example, corresponding features can be extracted from the regions of interest at different times, which can be used to select features that are most useful for classifying whether a subject is performing an effortful mental task. Note that feature extraction at 410 can be performed for each permutation of pairs of brain regions. For example, if there are M regions of interest, features can extracted pairwise for up to M!/(M−2)!2! pairs (e.g., if there are 10 regions of interest, features can be extracted from 45 different pairs of regions of interest). Additionally, as described below, features can be extracted for each pair of regions in different domains (e.g., in the time domain and the frequency domain), and/or in particular frequency bands within the frequency domain.

In some embodiments, CCA can be used to compute features that contain information about the functional connectivity of the brain network. Channels (e.g., an individual pair of contacts in the bipolar reference scheme can correspond to one channel) can be organized into corresponding regions of interest (e.g., using the ELA described below in connection with FIG. 14). For example, two regions X and Y can contain $n_x$ and $n_y$ channels, respectively, that vary with time, t. The signals from these channels can be organized as a matrices, with rows representing channels, and columns representing samples at particular points in time. For example, X and Y can be represented by:

$$X = \begin{bmatrix} X_{1,1} & \cdots & X_{1,t} \\ \vdots & \ddots & \vdots \\ X_{n,1} & \cdots & X_{n,t} \end{bmatrix} \quad (1)$$

$$Y = \begin{bmatrix} Y_{1,1} & \cdots & Y_{1,t} \\ \vdots & \ddots & \vdots \\ Y_{n,1} & \cdots & Y_{n,t} \end{bmatrix} \quad (2)$$

Two singular value decompositions can be performed on the groups of signals, X and Y, and the resulting change in bases can maximally correlate the signals within each set as shown in EQS. 3 and 4:

$$X = U_x \Sigma_x V_x^T \quad (3)$$

$$Y = U_y \Sigma_y V_y^T \quad (4)$$

A matrix multiplication can be performed to find the maximum correlation between each set of signals. The first singular value of the product matrix can be referred to as the canonical correlation coefficient, which represents spatial correlation between the two sets of signals, and can be represented as:

$$Q_{xy} = U_x V_x^T U_y V_y^T \quad (5)$$

For each pair of regions, canonical correlation can be used to calculate one feature, where the value of the feature can be a number between 0 (e.g., having no correlation) and 1 (e.g., having full correlation).

In general, as the window size used to sample the data decreases, task and non-task distributions are more difficult to accurately distinguish. However, larger window sizes generally include more data, and accordingly increase the computational intensity or performing a CCA calculation between each pair of regions. In addition to the increased computational intensity, larger window sizes can also introduce a lag between when the subject enters an effortful mental state and the time when the effortful mental state can be detected. For example, if the effortful mental state begins at the beginning of a window, the time between onset of the effortful mental state and detection is the entire length of the window. This can be mitigated by overlapping the windows, however this effectively increases the number of samples for which calculations need to be performed, which can further raise the computational intensity.

As described below in connection with FIG. 22, accuracy and efficiency was investigated for various window sizes ranging from 200 ms to 20 seconds with an overlap of 200 ms. While the window size is generally described herein as being four or five seconds, this is merely an example, and other window sizes can be selected with various amounts of overlap.

For example, a first region of interest X can include a first group of n signals that vary with time, and a second region of interest Y can include a first group of m signals (where n may or may not be equal to m) that vary with time. The number of signals used to analyze the correlation between regions of interest X and Y can be the smaller of the number of signals in region X and the number of signals in region Y. For example, the number of signals used in the analysis can be the smaller of n and m. That is, if one brain region has more channels than another brain region, the smaller number of channels are chosen. In some embodiments, the specific channels chosen for inclusion can be based on the probability that the channel receives signals from the region of interest (e.g., based on output from the ELA), where the channels with the highest probabilities can be kept until the number of channels is equal to the smaller number of channels, while the remaining channels (e.g., with the lowest probabilities) can be omitted. This can ensure that the same number of signals are considered for each pair of regions. For example, if a first region is associated with 4 channels, a second region is associated with 6 channels, and a third region is associated with 10 channels, when evaluating the first and third regions, 4 channels can be used (e.g., by omitting the 2 channels associated with the second region with the lowest probability of receiving signals from that region), but when evaluating the second and third regions, 6 channels can be used (e.g., by omitting the 4 channels associated with the third region with the lowest probability of receiving signals from that region). Canonical correlation estimates can be generated using time domain signals, whereas canonical coherence estimates can be generated using frequency domain inputs. Frequency domain inputs can be calculated by averaging the continuous power signal over frequency bands of interest (e.g., 4-8 Hz, 8-15 Hz, 15-30 Hz, 30-55 Hz, and 65-200 Hz) using Morlet wavelet analysis.

Two sets of data X and Y can be represented as:

$$X[=]p \times n \quad (6)$$

$$Y[=]p \times n. \quad (7)$$

Covariance matrices can be represented as:

$$Cov(X,X)=\Sigma_{XX}=XX^T \quad (8)$$

$$Cov(X,Y)=\Sigma_{XY}=XY^T \quad (9)$$

$$Cov(Y,Y)=\Sigma_{YY}=YY^T \quad (10)$$

In order to determine the canonical correlation between X and Y, a pair of coefficient vectors a and b are sought that maximize the correlation $\rho=Cov(aX, bY)$, with the ultimate goal being to find the optimum linear combination of the measurements within each set (X and Y), such that the resulting series are maximally correlated. A process of finding coefficient vectors a and b can begin by defining two variables G and H as linear combinations of X and Y, as follows:

$$G=a^T*X \quad (11)$$

$$H=b^T*Y \quad (12)$$

A correlation between X and Y can be represented in terms of the variance and covariance as follows:

$$\rho = \frac{a^T X^T Y b}{\sqrt{(a^T X^T X a)(b^T X^T Y b)}}. \quad (13)$$

X and Y can be reduced using singular value decomposition (SVD) as follows:

$$X=U_X\Sigma_X V_X \quad (14)$$

$$Y=U_Y\Sigma_Y V_Y \quad (15)$$

where U, Σ, and V are matrices that are determined using SVD techniques, with subscripts indicating the region (X or Y) to which the matrix corresponds. The simplified solution of the maximization problem can be found by computing:

$$Q_{XY}=Cov(X)*Cov(X,Y)*Cov(Y,Y), \quad (16)$$

which can be simplified using EQS. 14 and 15 to:

$$Q_{XY}=U_X V_X^T V_Y U_Y^T \quad (17)$$

$Q_{XY}$ can be reduced using singular value decomposition as:

$$Q_{XY}=U_Q \Sigma_Q V_Q \quad (18)$$

where the vectors a and b can be defined in terms of the covariance of X and Y, and the singular value decomposition of $Q_{XY}$. The principal vectors of a and b can be used to define a fixed basis or projections space and are defined as:

$$a=XX^T U_Q \quad (19)$$

$$b=YY^T V_Q \quad (20)$$

After finding vectors a and b, the fixed canonical correlation, ρ, and coherence values can be calculated via a simple multiplication step using EQ. 13.

At 412, process 400 can train a classification model using features extracted from the neural activity at 410, and labels corresponding to the features. As described above, for each pair of regions (and, in some cases, for signals in multiple individual frequency bands from each pair of regions), CCA techniques can be used to calculate a feature. Extending an earlier example, if there are 10 regions of interest, performing CCA using time domain signals can produce 45 features for each window of data that is analyzed, and performing CCA using frequency band signals in the band from 65-200 Hz can produce an additional 45 features for each window of data that is analyzed. In such an example, one minute of data using a 5 second window to sample the data (with no overlap) can generate 1,080 features, each corresponding to a correlation between a pair of regions during a particular time window in the time domain or frequency domain. In some embodiments, any suitable classification model can be trained to classify features extracted at 410 as corresponding to task or non-task activity. For example, process 400 can train a Support Vector Machine (SVM) to classify features extracted at 410 activity. As another example, process 400 can train a CNN to classify features extracted at 410 as corresponding to task or non-task activity. In some embodiments, process 400 can use groups of labeled features (e.g., each group of features can correspond to correlations of signals between two regions of interest in a particular four second window) extracted using canonical correlation analysis (sometimes referred to herein as canonical correlation features) and corresponding "task" and "non-task" class labels as training data, validation data, and/or test data. For example, in some embodiments, process 400 can train the classification model using a five-fold cross validation. In such an example, the labeled data can be separated into a test data set and a training data set, and the training data set can be subdivided into five folds (e.g., five equal sized subsets with individual groups of features assigned to a particular fold). In some embodiments, the sizes of the task and non-task classes can be balanced prior to dividing or subdividing the data into different data sets. For example, the class of smaller size can be randomly oversampled with replacement (e.g., process 400 can randomly select an example form the entire smaller size class each time) until the sizes of the classes are balanced.

In some embodiments, during training of the classification model, process 400 can use four of the five folds as training data, and can use the remaining fold as a validation data set to determine the accuracy of the model during training. For example, the classification model can be trained using the training data set including four folds, and after each training run, the validation data set can be input to the classification model and the accuracy of the classification model's classifications of the validation data set can be used to determine whether performance of the classification model is increasing or decreasing. In a more particular example, performance of the classification model can be evaluated at each iteration to determine various parameters, such as accuracy, true positive rate (sensitivity), true negative rate (specificity), false positive rate, and/or false negative rate. In some embodiments, process 400 can stop training the classifier when performance has improved by less than a threshold amount for a certain number of runs in a row. After stopping the training, process 400 can then use a different fold as the validation data set. Process 400 can continue training the classification model until each fold has been used as the validation data set. Cross validation can reduce the likelihood that improving model performance reflects overfitting. In some embodiments, after training of the classification model is complete, process 400 can use the test data set to evaluate performance of the classification model, which can be used as an indication of how well the classification can be expected to perform on unlabeled data. In some embodiments, the likelihood that the observed performance of the trained classification model is due to chance can be inferred by retraining a classification model after shuffling class labels (e.g., before class sizes are balanced), and evaluating the performance of the model trained using the shuffled data using the test set. In some such embodiments, labels can be randomly assigned in a way that preserves the original class sizes.

In some embodiments, process 400 can select a subset of features to use for training the classification model through a ranking process based on SVM criteria. For example a feature set, Var, of size N can be selected. In some such embodiments, during the feature selection process, process 400 can re-calculate performance of the classification model for a feature set of size N−1 after each feature is removed and subsequently replaced. The performance difference from removing each feature can be compared, and the feature that was removed to produce the feature set that produced the highest performance can be removed and ranked as the least important feature. The remaining features (i.e., the feature set that produced the highest performance) can be re-evaluated by removing each feature, and removing the feature that had the least impact on performance, which can be ranked as the second least important feature. This can be repeated until each feature has been ranked, with the last remaining feature being ranked as most important, the final feature that was removed as the second most important, and so on. In some embodiments, a set of features to use for training can be selected by selecting a feature set that yielded maximum classification accuracy, up to 5 features. In some embodiments, feature sets from all frequency bands can be included in frequency domain feature selection.

At 414, process 400 can receive signals indicative of neural activity recorded while the subject is performing unknown activities. As described above in connection with FIGS. 1-3, a pulse generator and/or computing device can receive signals from monitoring electrodes (e.g., monitoring electrodes 102) associated with different anatomical regions of a subject's brain. In some embodiments, process 400 can collect a particular amount of data before moving to 416. For example, process 400 can collect a sample of data that is similar in length to the window length used during training. In a more specific example, process 400 can collect four seconds of signals before moving to 416.

At 416, process 400 can extract features from the unlabeled neural activity using one or more of the techniques used to extract features during training (e.g., as described above in connection with 410).

At 418, process 400 can provide one or more of the extracted features as input to the trained classification model. In some embodiments, process 400 can provide only a subset of the extracted features to the classification model, such as features corresponding to the subset of features used to during training of the classification model. In some embodiments, the trained classification model can provide a probability that the neural activity from which the features were generated corresponds to performance of an effortful mental task. Additionally or alternatively, in some embodiments, the trained classification model can provide a probability that the neural activity corresponds to a particular mental state (e.g., a state of heightened cognitive interference, a state of heightened emotional conflict, etc.). In some embodiments, an output can be provided by a single classification model that has been trained to classify data with signals collected during MSIT labeled as corresponding to a state of heightened cognitive interference, signals collected during ECR labeled as corresponding to a state of heightened emotional conflict, and other signals labeled as not corresponding to either state (e.g., as "non-task" data). Alternatively, in some embodiments, multiple binary classification models can be trained (e.g., a classifier trained to distinguish MSIT and non-task signals, a classifier trained to distinguish ECR and non-task signals, and a classifier trained to distinguish MSIT and ECR signals. Based on the outputs of the various classification models, the predicted state can be based on voting (which may or may not be weighted based on the confidence of each predication). For example, if the MSIT/non-task classifier and the ECR/non-task classifier provides outputs indication that sample singles correspond to non-task data, that sample can be considered non-task data regardless of the output of the MSIT/ECR classifier.

At 420, process 400 can determine whether the subject is performing an effortful mental task based on the output(s) of the trained classification model. In some embodiments, if the probability that the subject is performing an effortful mental task is at least a threshold probability, process 400 can determine that the subject is performing an effortful mental task.

If process 400 determines that the subject is performing an effortful mental task ("YES" at 420), process 400 can move to 422, at which process 400 can cause deep brain stimulation to be provided to the subject to assist the subject in performance of the effortful task. In some embodiments, deep brain stimulation can be provided at any suitable intensity and for any suitable duration. After beginning to provide stimulation at 422, process 400 can return to 414 to determine whether the subject is, or is not, performing an effortful mental task.

Otherwise, if process 400 determines that the subject is not performing an effortful mental task ("NO" at 420), process 400 can return to 414 and continue to receive signals indicative of neural activity.

As described below in connection with FIG. 29, performance of classification models trained using data from a single session can suffer when it is tested using data recorded during a later session (e.g., days after the first session), but the performance of a classifier trained using data from both sessions suffers a much smaller amount when tested on both sessions. Accordingly, in some embodiments, data used to train the classification model can be collected over multiple sessions, and/or the classifier can be retrained (or further trained) using newly acquired information. Additionally or alternatively, in some embodiments, a subject can perform sessions of known task performance at home to collect additionally information (e.g., through a computing device used to present the MSIT or ECR task, and signals acquired via the monitoring electrodes). The newly acquired data can be used to train a new classification model, or update the training of the classification model. For example, data can be collected sent to a remote server, which can analyze the new data and/or train the classification model using the new data. If the new classification model produces more accurate results for the test dataset than the classification model being used to provide therapy to the subject, the new classification model can be pushed to the subject's computing device and/or pulse generator.

Figure 5:
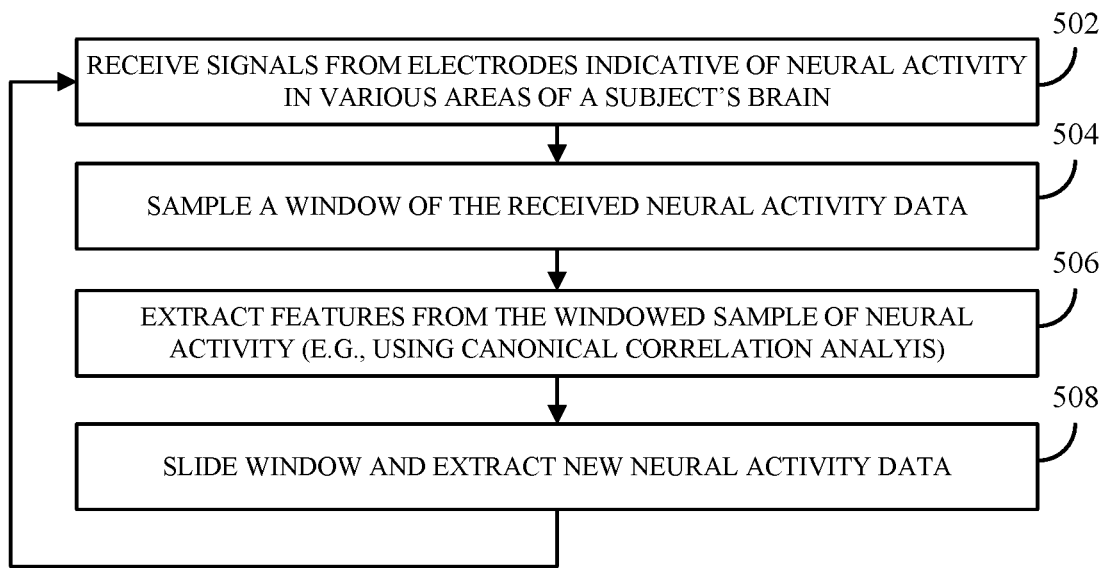
FIG. 5 shows an example of a process for extracting features from signals indicative of neural activity in various areas of a subject's brain in accordance with some embodiments of the disclosed subject matter.

FIG. 5 shows an example 500 of a process for extracting features from signals indicative of neural activity in various areas of a subject's brain in accordance with some embodiments of the disclosed subject matter.

As shown in FIG. 5, at 502, process 500 can receive signals from monitoring electrodes (e.g., monitoring electrodes 102) corresponding to neural activity in various regions of the subject's brain. As described above in connection with FIG. 1, the signals can be received by a pulse generator (e.g., pulse generator 104) or other suitable device.

At 504, process 500 can sample a window of the received neural activity. For example, as described above in connection with FIG. 4, process can sample a next four seconds of the signals received at 502.

At 506, process 500 can extract features from the neural activity sampled at 504. In some embodiments, process 500 can use any suitable technique or combination of techniques to extract features, such as CCA or FCCA, as described above in connection with 410 of FIG. 4.

At 508, process 500 can slide the window, and return to 502 to receive and sample new neural activity data. In some embodiments, process 500 can slide the window any suitable amount. For example, process 500 can slide the window by an amount of time equal to the size of the window. As another example, process 500 can slide the window by an amount of time that is less than the size of the window (e.g., 10 ms less, 20 ms less, 100 ms less, 500 ms less, 1 second less, etc.), which can result in some overlap of the sampled signals. In some embodiments, such overlap can reduce the response time (e.g., if the window is four seconds long with 500 ms of overlap, samples can be analyzed every 3.5 seconds, rather than every four seconds).

Figure 6:
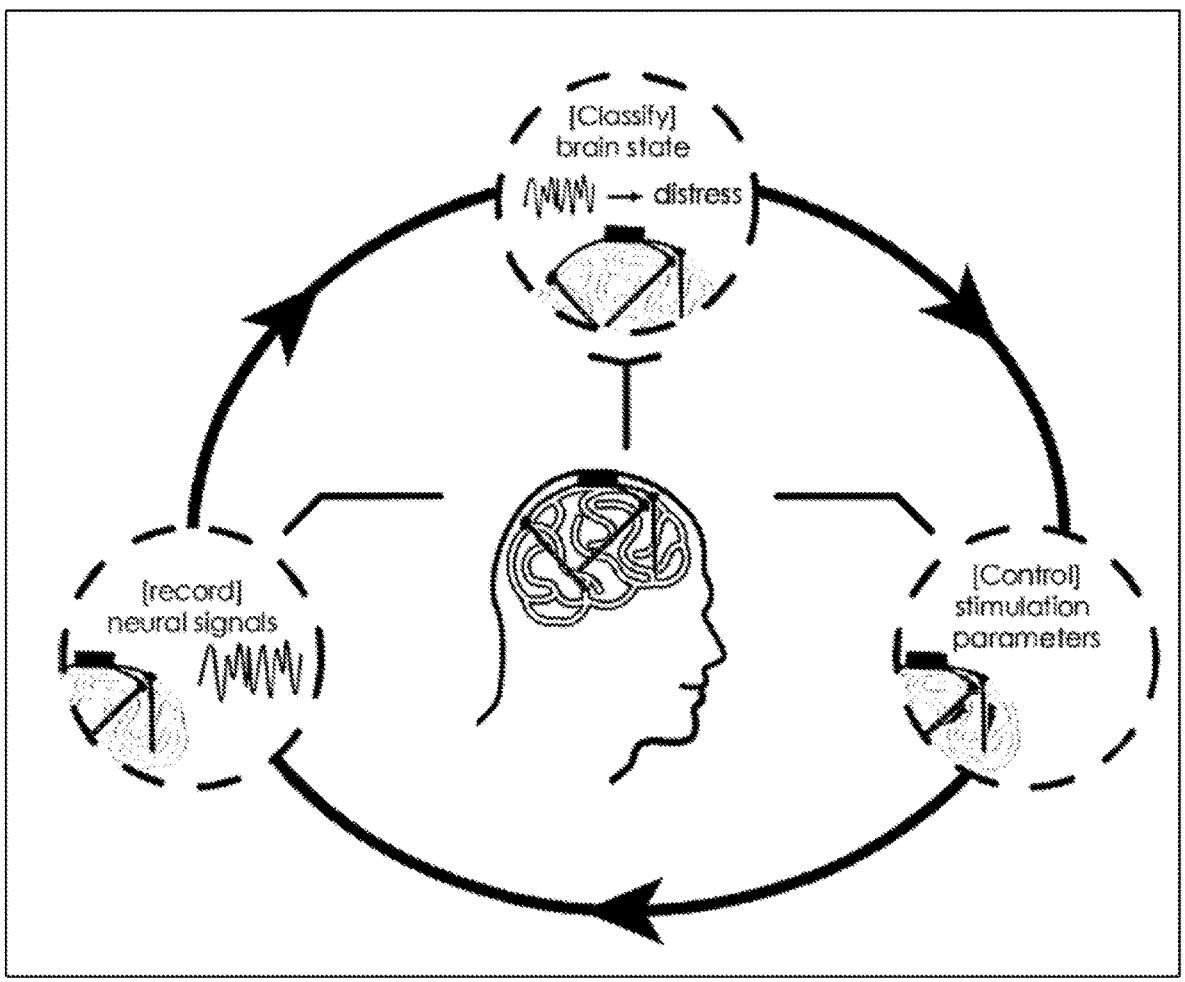
FIG. 6 shows an example of a closed-loop DBS technique that can be used to treat symptoms of a neuropsychological disorder in accordance with some embodiments of the disclosed subject matter.

FIG. 6 shows an example of a closed-loop DBS technique that can be used to treat symptoms of a neuropsychological disorder in accordance with some embodiments of the disclosed subject matter. Closed-loop DBS can be used to treat patients suffering from illnesses such as post-traumatic stress disorder (PTSD). PTSD is prevalent among soldiers and veterans after returning from combat. During closed-loop DBS for PTSD, implanted electrodes can continuously monitor brain activity (e.g., as described above in connection with 414 of FIG. 4). The neural activity can be sent to an implanted device to decode brain states via feature estimation and classification by a trained classifier (e.g., as described above in connection with 416 of FIG. 4). When a brain state related to psychological distress is detected, specific stimulation commands can be sent back to the electrodes or other specific stimulating electrodes, which can force the network out of the distressed state to relieve symptoms.

Figure 7:
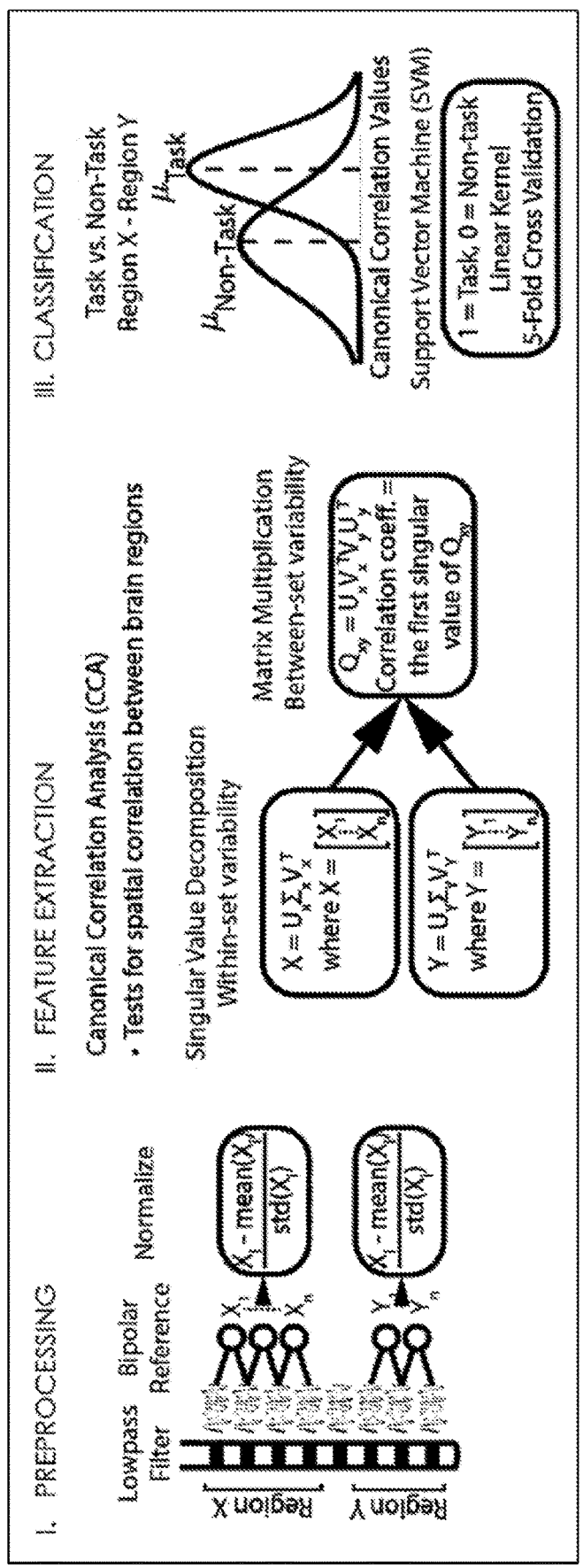
FIG. 7 shows a diagram illustrating an example of a process for facilitating an effortful mental task by providing real-time deep brain stimulation in accordance with some embodiments of the disclosed subject matter.

FIG. 7 shows a diagram illustrating an example of a process for facilitating an effortful mental task by providing real-time deep brain stimulation in accordance with some embodiments of the disclosed subject matter. More particularly, FIG. 7 shows a graphical representation of techniques that be used with some embodiments of the disclosed subject matter described herein for detecting and facilitating an effortful mental task by providing real-time deep brain stimulation.

FIG. 8 shows an example of a process for selecting features to use when training a classification model in accordance with some embodiments of the disclosed subject matter. In some embodiments, the process shown in FIG. 8 can be used in connection with 412 of FIG. 4.

Figure 9:
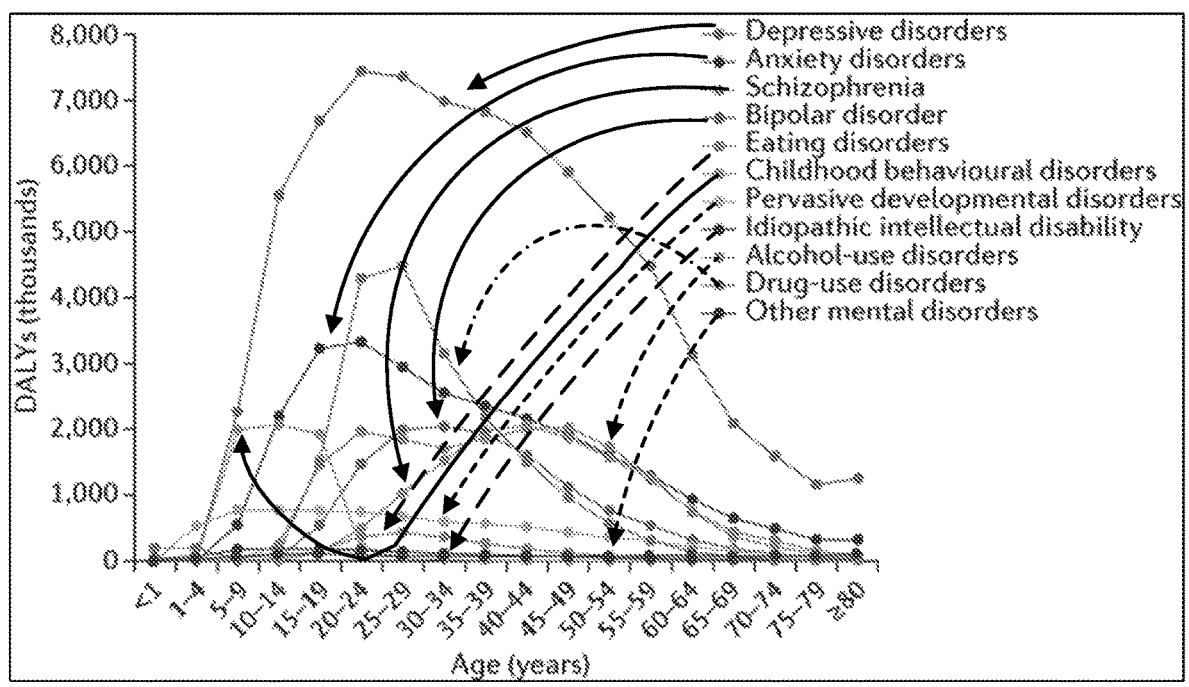
FIG. 9 shows an example of a graph illustrating the aggregate impact of various neurological, mental health, and substance-abuse disorders (in disability-adjusted life years) by age.

FIG. 9 shows an example of a graph illustrating the aggregate impact of various neurological, mental health, and substance-abuse disorders (in disability-adjusted life years) by age, which appears in Whiteford et al., "Global Burden of Disease Attributable to Mental and Substance Use Disorders: Findings from the Global Burden of Disease Study 2010," *The Lancet*, V. 382, Iss. 9904, November 2013, pp. 1575-86; doi:10.1016/0140-6736(13)61611-6. As shown in FIG. 9, disorders that can be treated using the mechanisms described herein (e.g., MDD, and anxiety disorders) have large aggregate effects. Accordingly, providing an intervention to reduce the impact of such disorders can dramatically improve the lives of many individuals.

Figure 10:
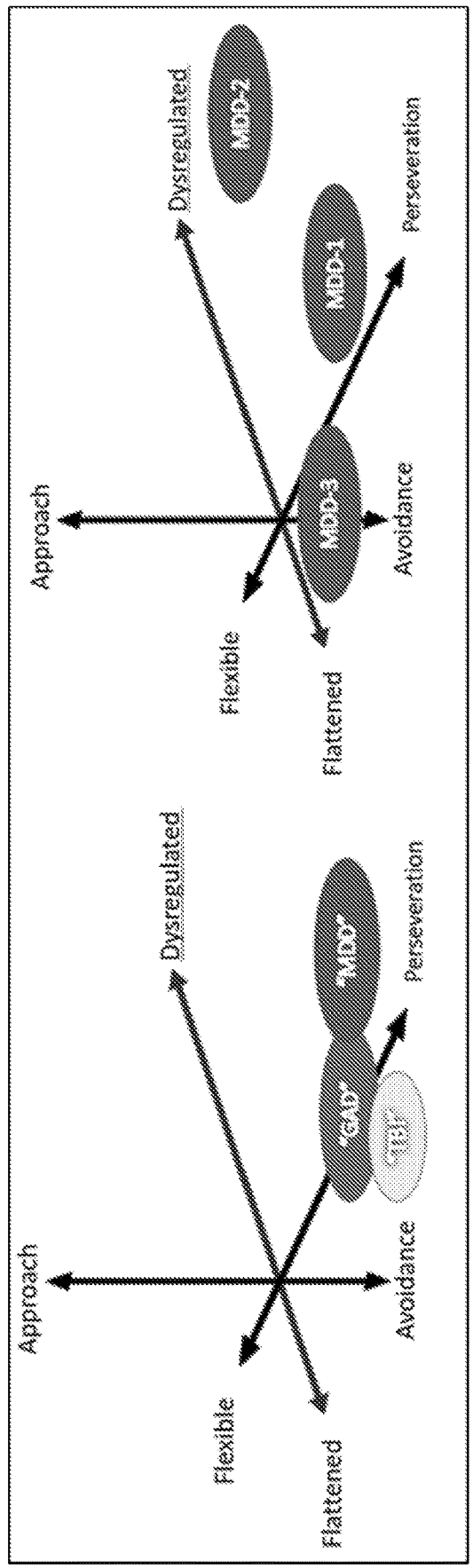
FIG. 10 shows plots illustrating that patients with different diagnoses including traumatic brain injury (TBI), generalized anxiety disorder (GAD), and major depressive disorder (MDD) can exhibit similar phenotype symptoms, and that patients that share the same diagnosis can exhibit dissimilar phenotype symptoms.

FIG. 10 shows plots illustrating that patients with different diagnoses including traumatic brain injury (TBI), generalized anxiety disorder (GAD), and major depressive disorder (MDD) can exhibit similar phenotype symptoms, and that patients that share the same diagnosis can exhibit dissimilar phenotype symptoms. In general, stable biomarkers for neuropsychiatric illness have not been found. Additionally, phenotypes overlap between multiple diagnoses, and are not homogenous for single diagnoses. As shown in FIG. 10, three patients with different diagnoses (i.e., TBI, GAD, and MDD) exhibit an overlapping phenotype, in that they all demonstrate cognitive rigidity and are unable to adapt in changing environments. On the right of FIG. 10, three patients with the same diagnosis (i.e., MDD) do not exhibit overlapping phenotypes. One patient exhibits emotional lability, while another patient is emotionally flat, and a third patient demonstrates cognitive rigidity.

Figure 11:
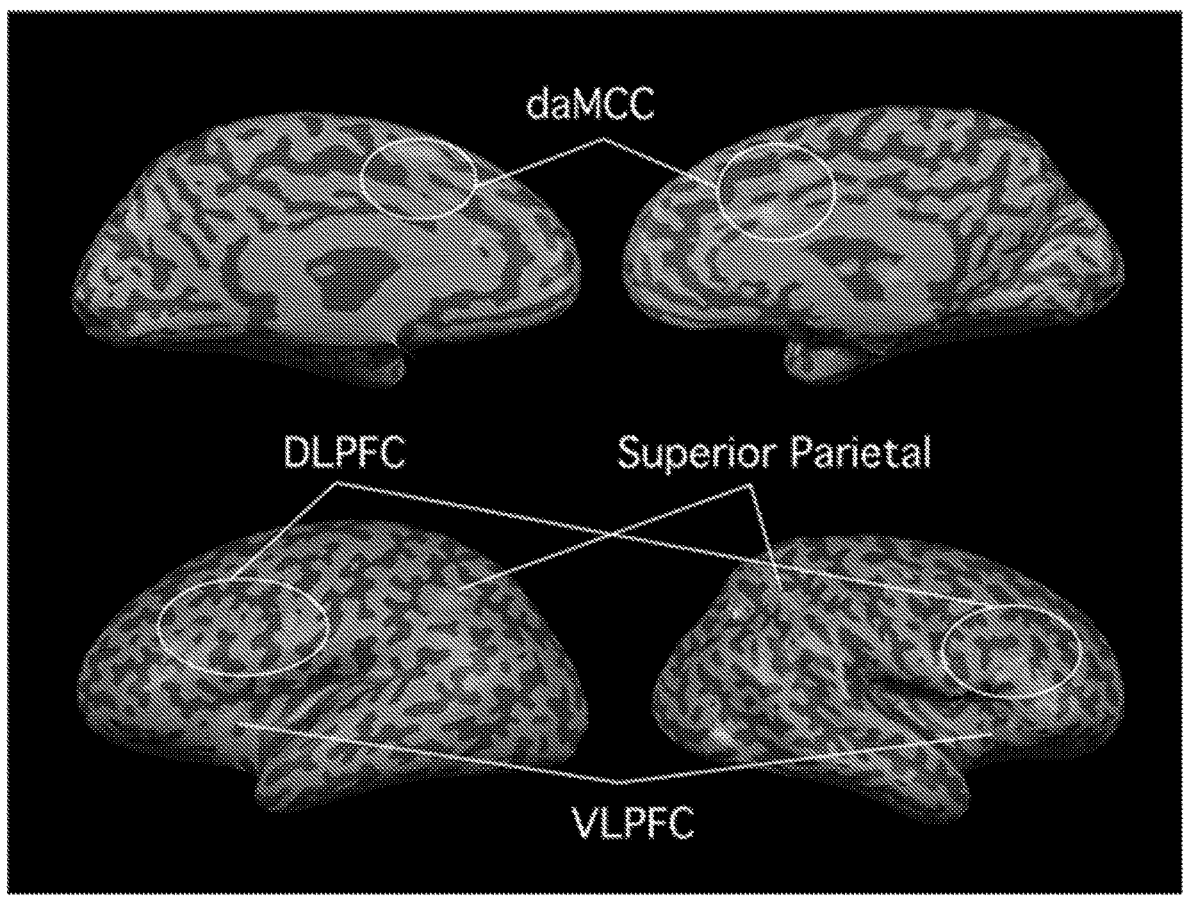
FIG. 11 shows an example of a functional Magnetic Resonance Imaging (fMRI) response of a subject while performing the MSIT task.

FIG. 11 shows an example of a functional Magnetic Resonance Imaging (fMRI) response of a subject while performing the MSIT task, which appears in Bush et al., "The Multi-Source Interference Task: An fMRI Task That Reliably Activates the Cingulo-Frontal-Parietal Cognitive/attention Network," *Nature Protocols*, V. 1, Iss. 1, June 2006, pp. 308-13; doi:10.1038/nprot.2006.48. The MSIT task has been shown to reliably and robustly activates the cingulo-frontal-parietal (CFP) cognitive/attention network during interference trials at the single subject level. The CFP includes the dACC, dorsolateral prefrontal cortex (dlPFC), and superior parietal cortex. Consistent with the results of other complex cognitive tasks, the perigenual anterior cingulate cortex (pACC) has been found to respond reciprocally to dACC activation. During studies of complex cognitive tasks increases in dACC activity are associated with decreases in pACC activity, and vice versa. During tasks involving emotion, increases in dACC activity are associated with increases pACC activity.

Figure 12:
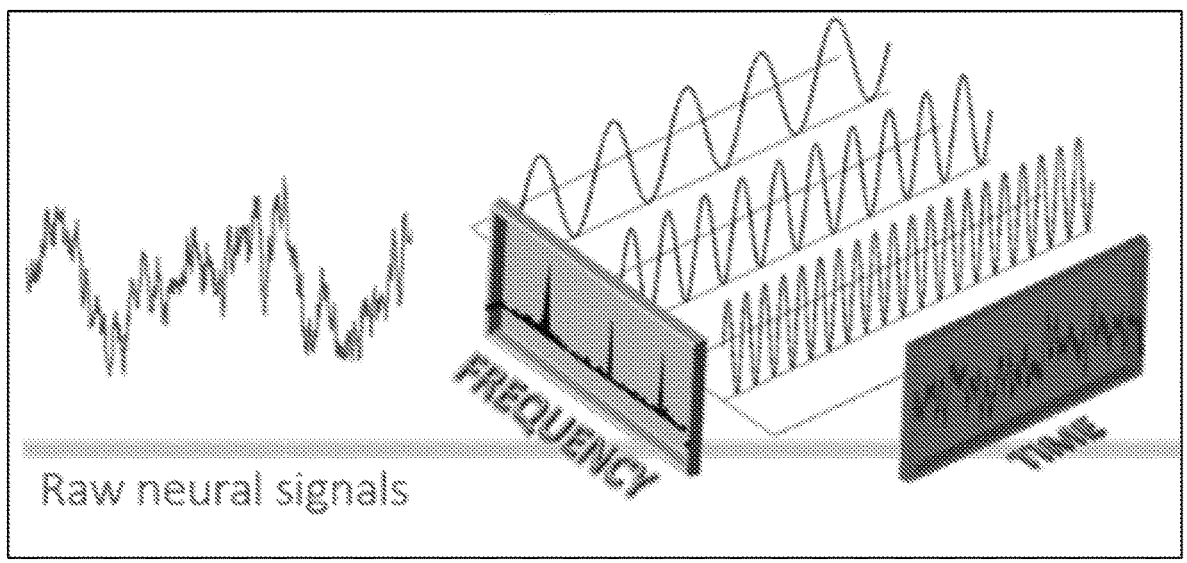
FIG. 12 shows an example of a raw neural signal and the raw signal decomposed into frequency components.

FIG. 12 shows an example of a raw neural signal and the raw signal decomposed into frequency components. As shown in FIG. 12, the raw signal on the left can be represented as the combination of signals in multiple frequency bands on the right.

Figure 13:
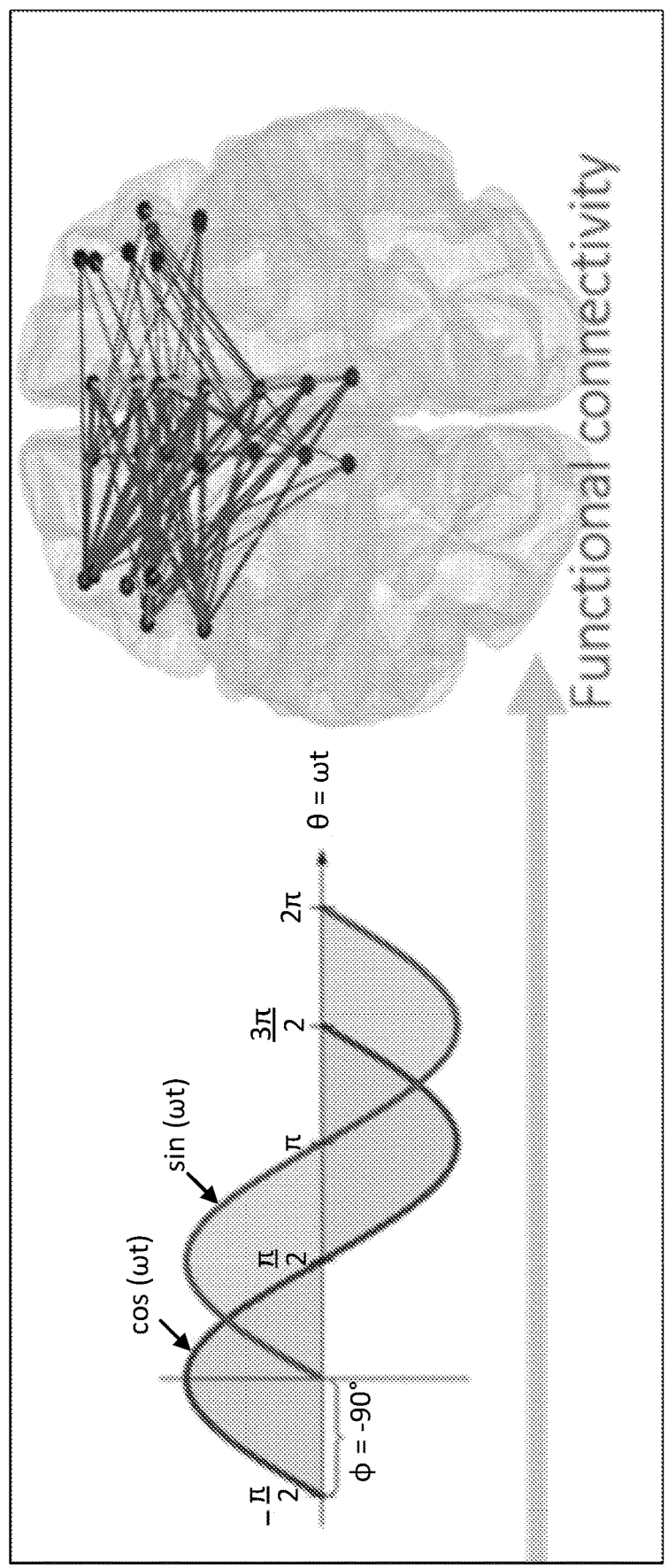
FIG. 13 shows an example of two signals of the same frequency, with a phase lag between the two signals, which can be used to deduce functional connectivity between the portions of the brain from which the signals originated.

FIG. 13 shows an example of two signals of the same frequency, with a phase lag between the two signals, which can be used to deduce functional connectivity between the portions of the brain from which the signals originated. As shown in FIG. 13, the phase difference on the left can be used to determine functional connections in the brain (e.g., as shown on the right) based on which regions of the brain are producing the two signals.

Functional connectivity can be estimated from signals generated using a variety of techniques that vary widely in temporal and spatial scales, including EEG and ECoG, in addition to LFP signals generated by implanted depth electrodes. In some embodiments, signals generated from high-density multi-sensor LFP sensors can be used to identify neural signatures of neuropsychiatric illness.

Figure 14:
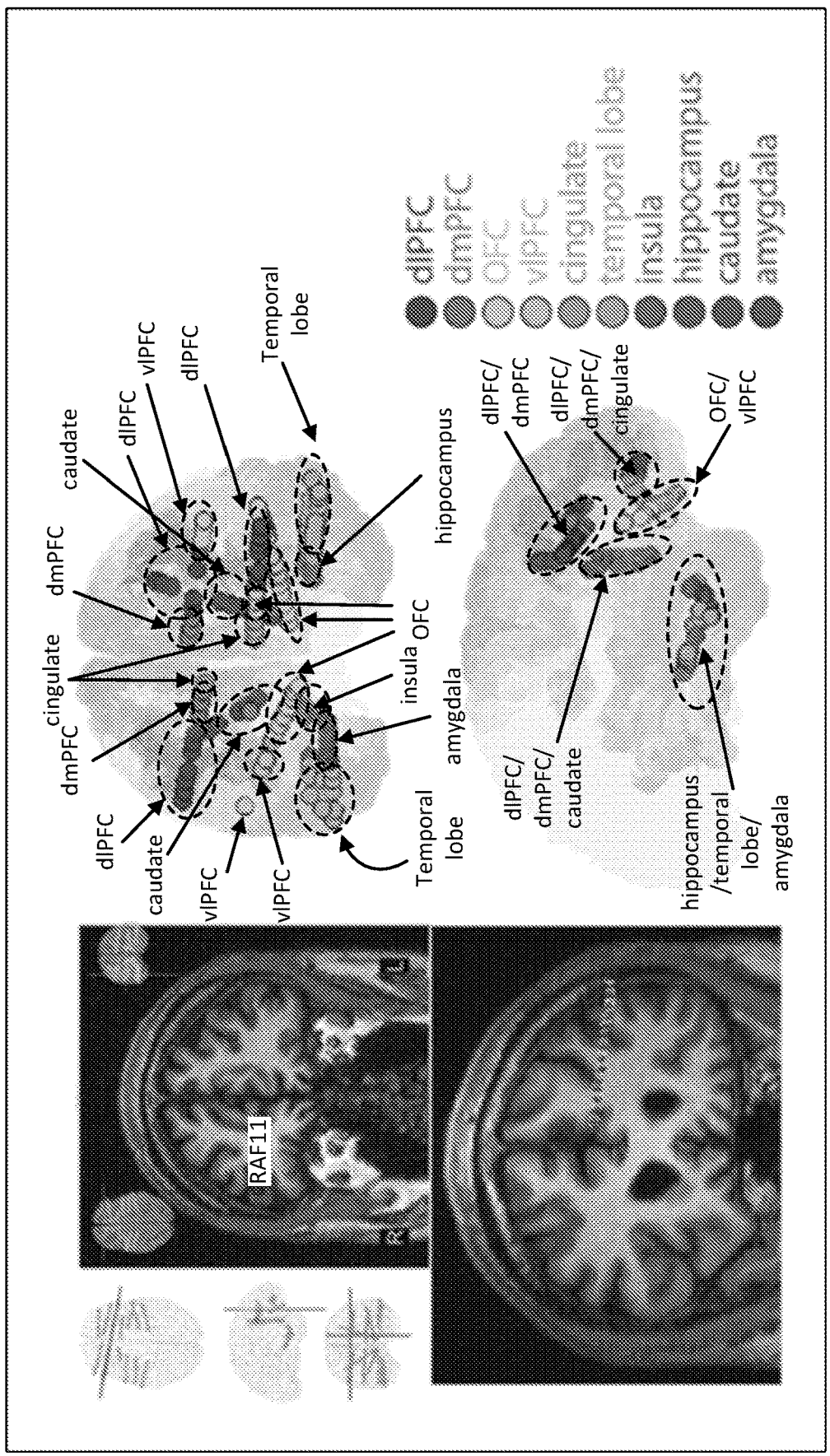
FIG. 14 shows an example of electrode positions within particular brain regions located using an Electrode Labeling Algorithm (ELA) in conjunction with a pre-operative Magnetic Resonance Imaging (MRI) scan and a post-operative Computed Tomography (CT) scan.

FIG. 14 shows an example of electrode positions within particular brain regions located using an ELA in conjunction with a pre-operative MRI scan and a post-operative CT scan. In some embodiments, electrodes can be localized by using a volumetric image co-registration procedure. For example, a Preoperative T1-weighted MRI can be aligned with a postoperative CT. Electrode coordinates can be manually determined from the CT and placed into the native space. The ELA can be used to map the electrodes to brain regions by estimating the probability that a particular brain region contributes to the dipoles that constitute the source of the signal. Electrodes implanted in the brain receive signals from multiple sources including white matter and gray matter. Currently, signals are believed to be generated by gray matter (whether cortical or subcortical), while white matter is believed to simply provide fibers for the signal to pass through. The ELA can identify the signal source by identifying the probability that a given electrode is labeled to a region of the brain (gray matter). A probability can assigned to each electrode based on the likelihood that it is positioned in a gray matter region of interest.

In some embodiments, the ELA can operate based on the assumption that the probability for each label to be a source for a given electrode can be estimated based on the Euclidean distance between the electrode and the brain label. The Euclidean distance can be defined based on electrode voxels and brain label voxels. Brain label voxels can be defined as all voxels where at least one of the label vertices is positioned inside the voxel volume mapped in the structural MRI. For electrode voxels where the distance from the center of the electrode is smaller than a given threshold, Dc, a 3D cloud can be circumscribed around the electrode. In some embodiments Dc can be any suitable value, such as 3 millimeters (mm). In some embodiments, each electrode can be modeled as a three-dimensional thin cylinder oriented in a specific direction. The ELA can calculate the probability that the electrode will receive signals from a particular brain region by finding the number of intersection voxels between the electrode voxel cloud and the label voxels, and can normalize based on the number of electrode voxels. The output of the ELA is an E×L matrix, X, where E is the number of electrodes and L is the number of labels. Xij is the probability that electrode i is getting a signal from the area of the brain corresponding to label. In the case where no label voxels intersect with the electrode voxels for a given electrode, Dc can be expanded by ΔDc and the length can be increased by Δl. For example, ΔDc can be 0.5 mm and Δl can be 1 mm. The expansion of ΔDc and Δl can continue until a detectable intersection between each label voxel and each electrode voxel is found. The corresponding probability for the given electrode can be decreased. In some embodiments, an electrode in white matter has a low probability for getting a signal from gray matter, while an electrode encased in grey matter will alternatively have a high probability.

Figure 15:
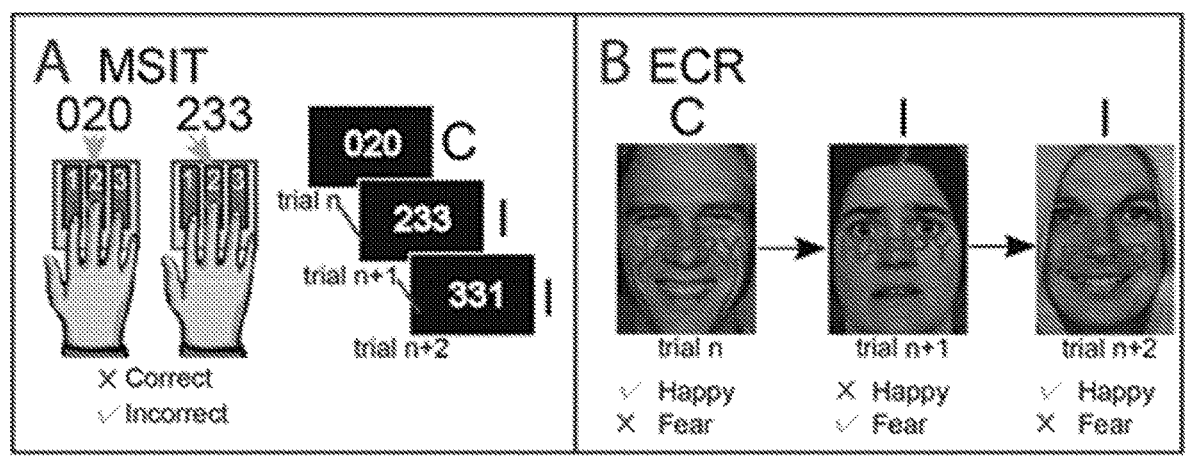
FIG. 15 shows an example of the MSIT and ECR procedure used to cause subjects to experience different conflict mental states.

FIG. 15 shows an example of the MSIT and ECR procedure used to cause subjects to experience different conflict mental states. In some embodiments, the MSIT is intended to maximize cognitive interference and dACC activation to study attention, response selection, and/or cognition. Elements of other tasks including the Stroop\Eriksen\ and Simone interference effects can also be used along with the MSIT task to activate the dACC during group analysis. The MSIT task involves giving subjects a keypad with buttons representing the numbers one, two, and three from left to right. Sets of three numbers are presented as stimuli, where one number is different than the other two. Participants are asked to report the value of the unique number (sometimes referred to as the distractor), regardless of its position and the value of the other two numbers. Each trial is considered as "congruent" or "incongruent" depending on the difficulty level. If the distractor was flanked by invalid targets (e.g., zeroes), the trial was congruent. If the distractor was flanked by valid targets, the difficulty level was determined by the value of the distractor. The value of the distractor either matched the button corresponding to its position (congruent) or did not match (incongruent) for each trial. Congruence changes from trial to trial are evenly balanced in number and frequency within each block. In some embodiments, the MSIT can include at least one, and up to five, 64-trial blocks. During each trial, a fixation cross is presented for two seconds followed by the image of three numbers between zero and three.

The ECR task is intended to provide insight on the neural mechanisms by which emotional conflict is monitored and resolved. The ECR task has been shown to generate robust neural activity related to the amount and resolution of emotional conflict on a trial-to-trial basis. Activity in the amygdala, dorsomedial prefrontal cortex (dmPFC), and the dlPFC reflect the amount of behavioral conflict, while activity in the rostral cingulate cortex is related to reduction in conflict. Activation of the rostral cingulate is accompanied by a simultaneous decrease in amygdala activation. This inhibitory relationship suggests that the rostral cingulate cortex may resolve conflict through top-down inhibition of the amygdala, whereas the dmPFC and the dlPFC monitor conflict. During an ECR task, subjects are presented with photos of faces with a fearful or happy expression and the photos are overlaid with the word 'HAPPY' or 'FEAR'. Subjects are asked to identify the emotion of the facial expression while ignoring the text. During congruent trials, the facial expression and word match. During incongruent trials, the facial expression and word do not match and reaction time typically increases.

The task can be chosen from a group including the Stroop task1, the emotional Stroop task, or combinations thereof. For example, the ECR task can include at least one, and up to six, 64-trial blocks. During each trial, a fixation cross can be presented for 2 seconds followed by an image of an emotive face showing a happy or fearful expression, with an overlaid word. The images can be presented in a pseudo-random order such that the identity, gender, and valence (fear or happy) appear to be shown randomly while the congruence changes are balanced within each block.

Figure 16:
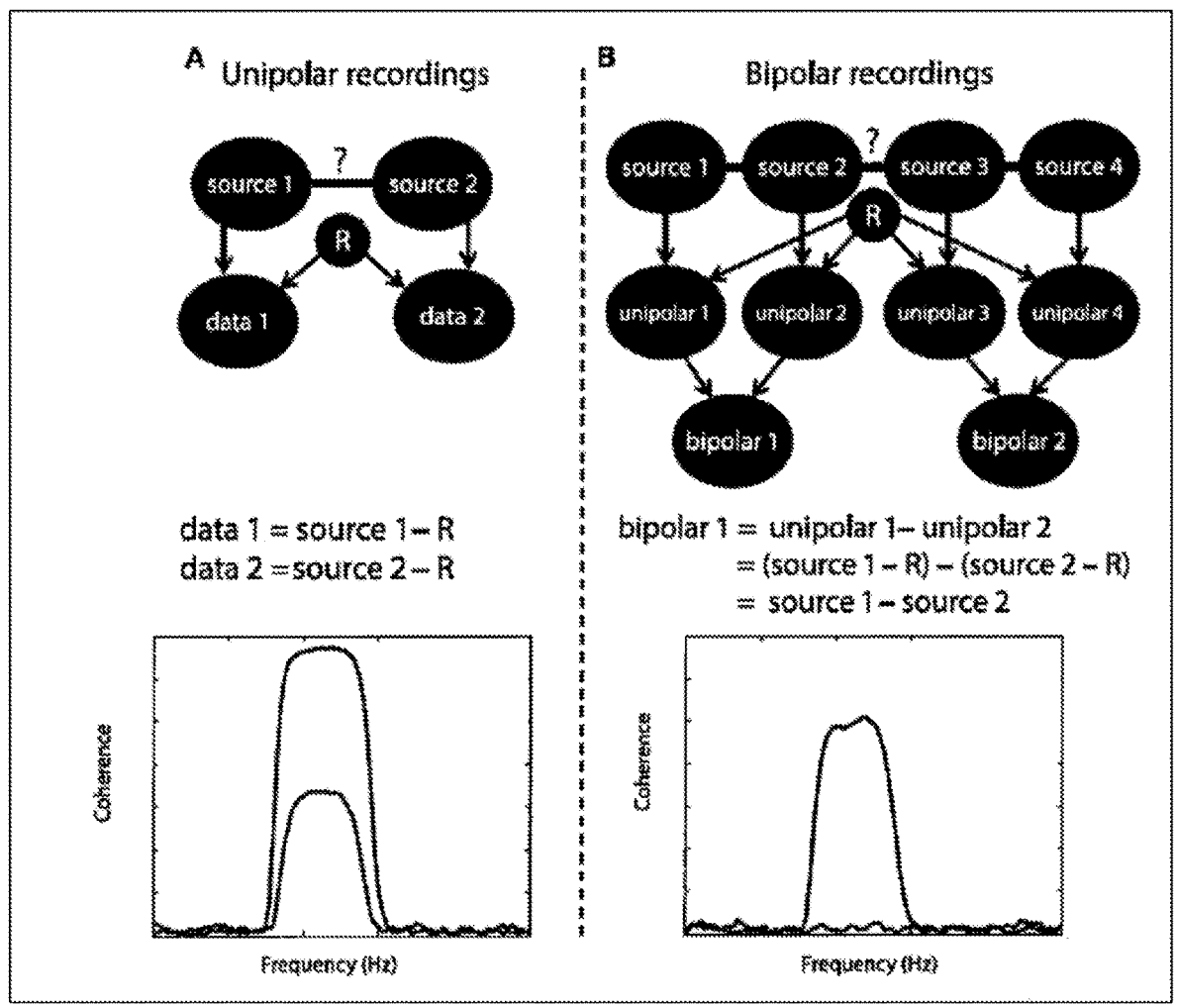
FIG. 16 shows examples of coherence signals generated using a unipolar technique and a bipolar technique.

FIG. 16 shows examples of coherence signals generated using a unipolar technique and a bipolar technique, which appears in Bastos et al., "A Tutorial Review of Functional Connectivity Analysis Methods and Their Interpretational Pitfalls," *Front. Syst. Neurosci.* 9, 175 (2015). As shown in FIG. 16, the measured signals contain both the signal of interest, signals of no interest, and noise. While nonzero connectivity estimates can be indicative of direct interaction between regions, this is not always the case. For example, local field potential recordings are often referenced with a single scalp electrode. Fluctuations in electric potential that occur at the reference location may be reflected in neighboring electrodes, which can cause spurious connectivity estimates. As shown in FIG. 16, a bipolar referencing strategy can mitigate spurious effects by subtracting one neighboring signal from another, which can eliminate the reference common to both signals. This scheme is based on the assumption that the reference is equally present in each channel, and that each channel reflects a different mixture of underlying neural signals.

Figure 17:
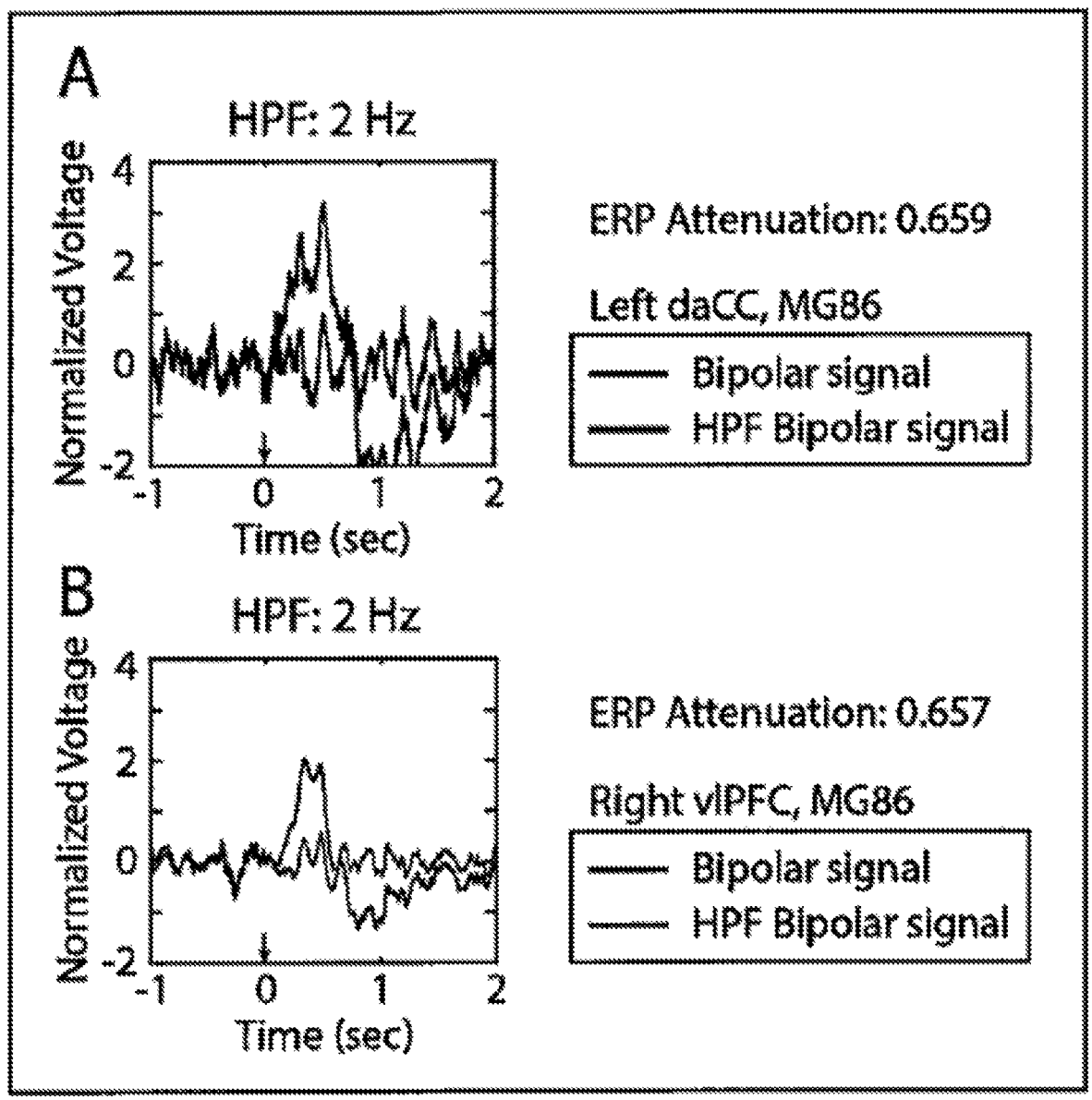
FIG. 17 shows examples of neural signals before and after applying a high pass filter, and parameters associated with the signals.

FIG. 17 shows examples of neural signals before and after applying a high pass filter, and parameters associated with the signals. In some embodiments, a high-pass filter (HPF) can be applied to eliminate frequency components of the signal below a cutoff frequency of 2 hertz (Hz). The high pass filtered signals shown in FIG. 17 were produced by averaging neural signals across all trials relative to the image onset or to the time the patient reacted to the picture during the ECR task. The resulting evoked-response potentials (ERPs) are averaged across all bipolar electrodes in each region. The attenuation of the average ERP per region after filtering can be visually inspected to determine adequate ERP removal. The neural signal across all trials were averaged relative to the image onset or to the time the patient reacted to the picture. The resulting ERPs were averaged across all bipolar electrodes in each region. The attenuation of the average ERP per region after filtering can be visually inspected to determine adequate ERP removal.

Figure 18:
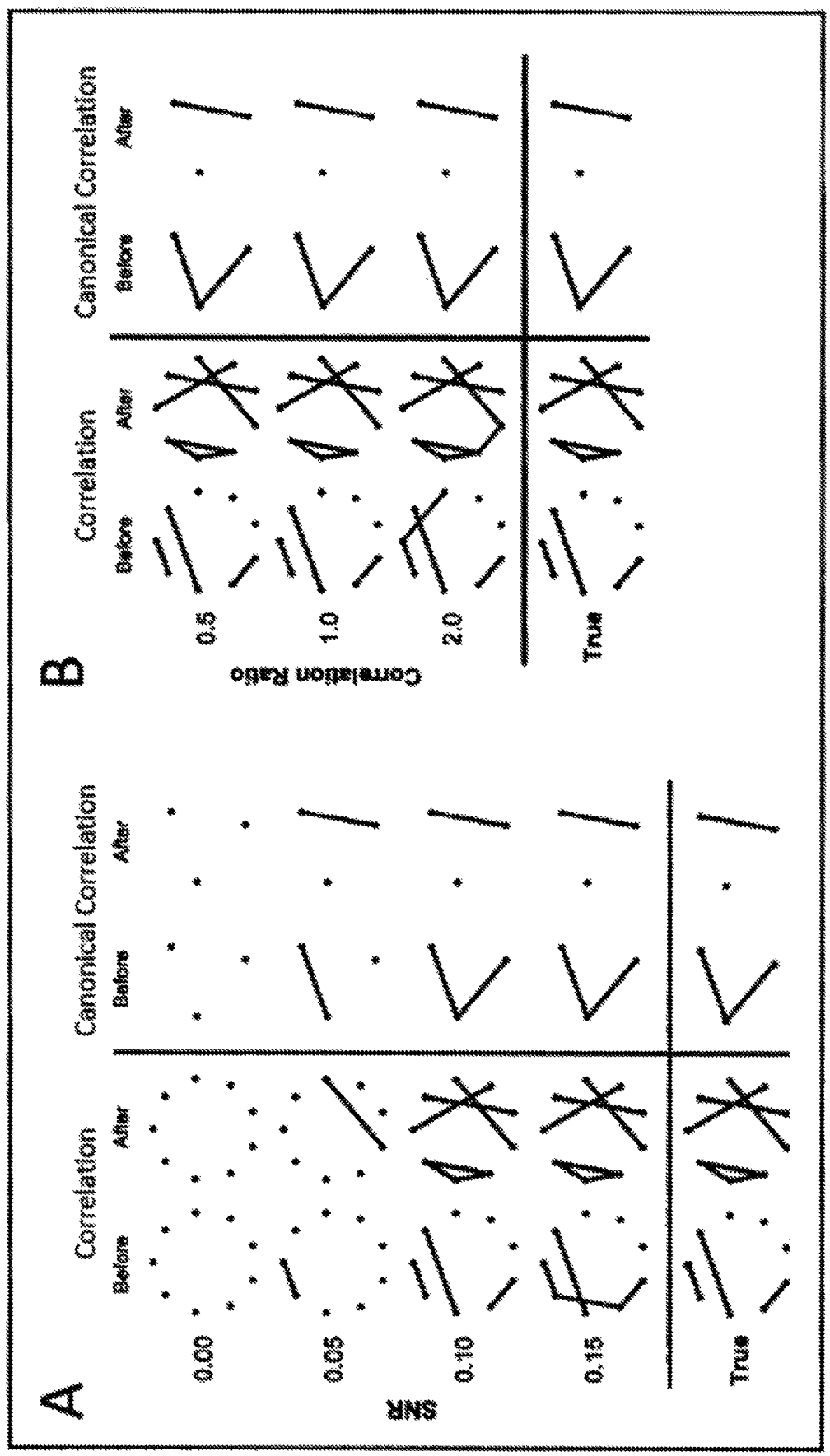
FIG. 18 shows examples of comparisons of correlations and canonical correlations between different regions at various Signal to Noise ratios.

FIG. 18 shows examples of comparisons of correlations and canonical correlations between different regions at various Signal to Noise ratios, which is adapted from Stephen et al., "Assessing dynamics, spatial scale, and uncertainty in task-related brain network analyses," *Front. Comput. Neurosci.* 8, 31 (2014). As shown in FIG. 18, CCA accurately predicts regional connectivity in the presence of high SNR and background correlations. Accordingly, region-level analysis intrinsic to CCA can be advantageous for identifying biomarkers of neuropsychiatric illness. The fMRI results are outlined in terms of ROI analysis and it is possible to draw parallels between CCA results and fMRI studies. CCA can facilitate regional analysis without resorting to signal averaging within regions of interest, which can be important for neural time series data. If two signals within a region are not phase aligned, signal averaging can cause a reduction in signal-to-noise ratio (SNR) by canceling out the signals of interest. Canonical correlation can also improve detectability of weak correlations present between many individual nodes, which can facilitate detection of correlations between regions that would not be detectable at the level of individual nodes.

Figure 19:
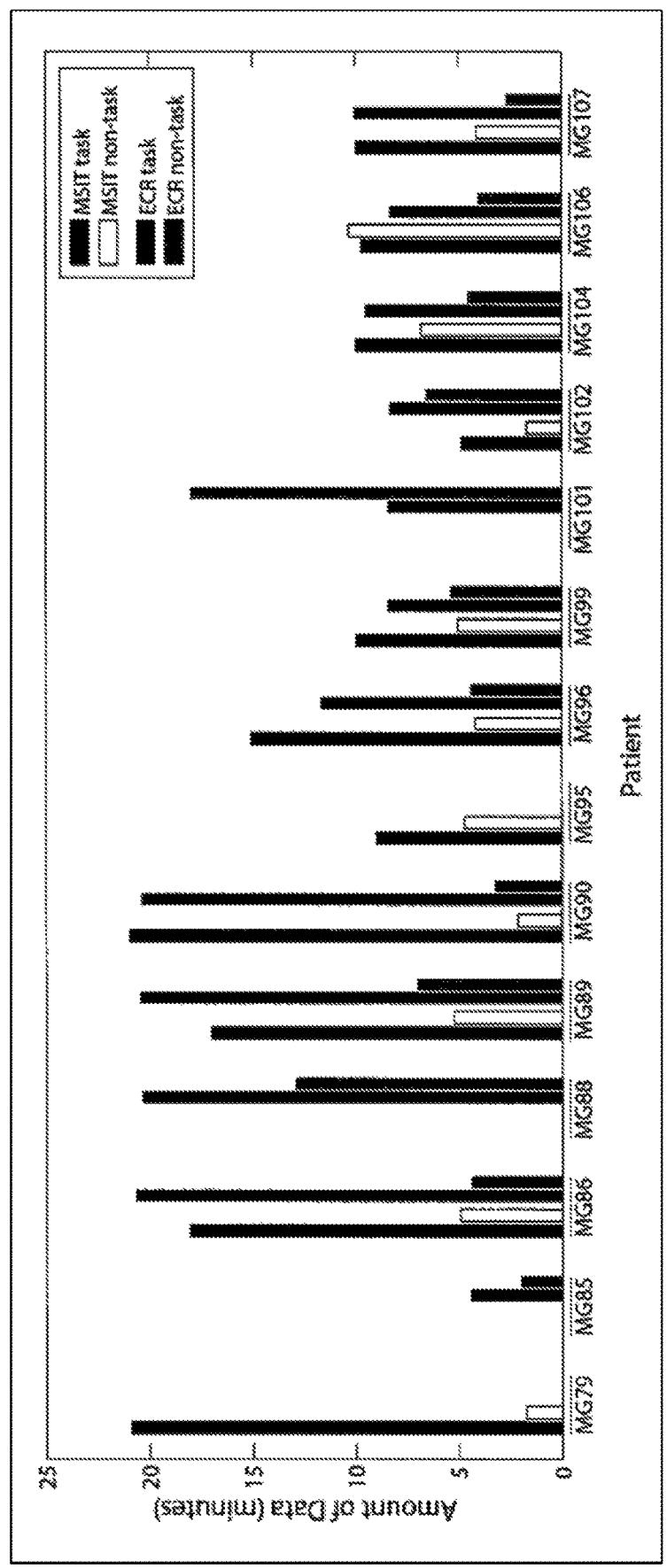
FIG. 19 shows an example of the amount of data (in minutes) collected from various subjects while the subject was performing a task and not performing a task.

FIG. 19 shows an example of the amount of data (in minutes) collected from various subjects while the subject was performing a task and not performing a task. As shown in FIG. 19, for 21 of 23 recording sessions, task data far exceeded non-task data. To balance unequal "task" and "non-task" class sizes, a data-level approach agnostic of the classification algorithm can be used to balance the class sizes by augmenting the smaller class through random oversampling with replacement to make up the difference between class sizes. The supplemental feature set generated through the random oversampling can then be concatenated to the original feature set.

Figure 20:
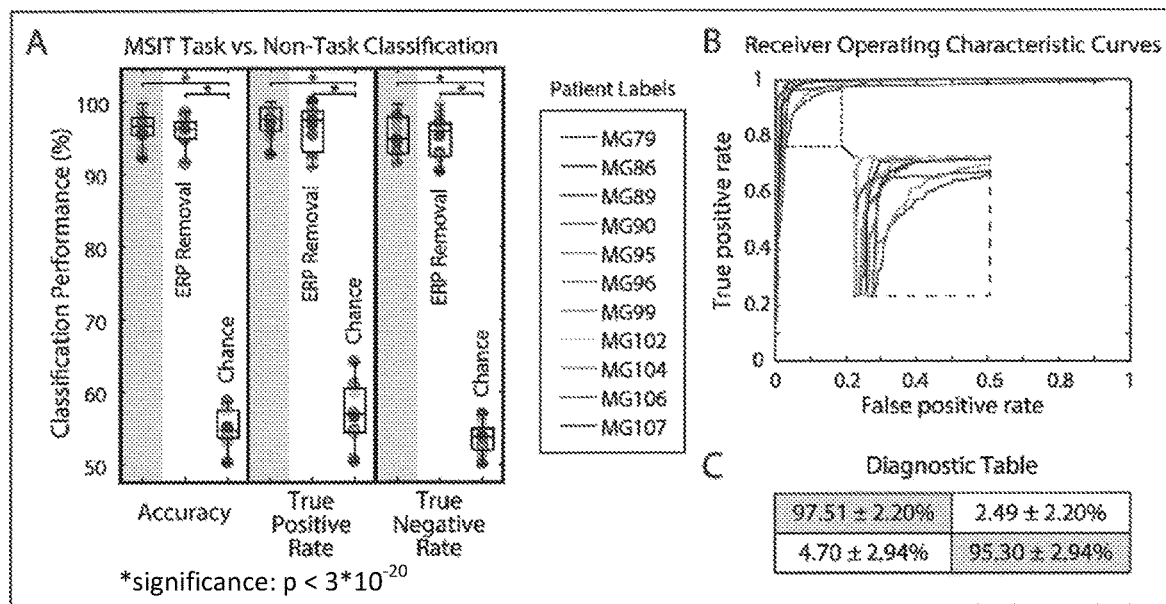
FIG. 20 shows an example of performance of a classification model trained in accordance with some embodiments of the disclosed subject matter on MSIT task and non-task data collected from various subjects.

FIG. 20 shows an example of performance of a classification model trained in accordance with some embodiments of the disclosed subject matter on MSIT task and non-task data collected from various subjects. As shown in FIG. 20, spatial correlation via canonical correlation features successfully distinguished periods of task engagement from free behavior for both the MSIT and ECR tasks. Mean sensitivity and specificity for MSIT task vs. non-task classification was 97.51±2.20%, and 95.30±2.94% (n=11), respectively.

Figure 21:
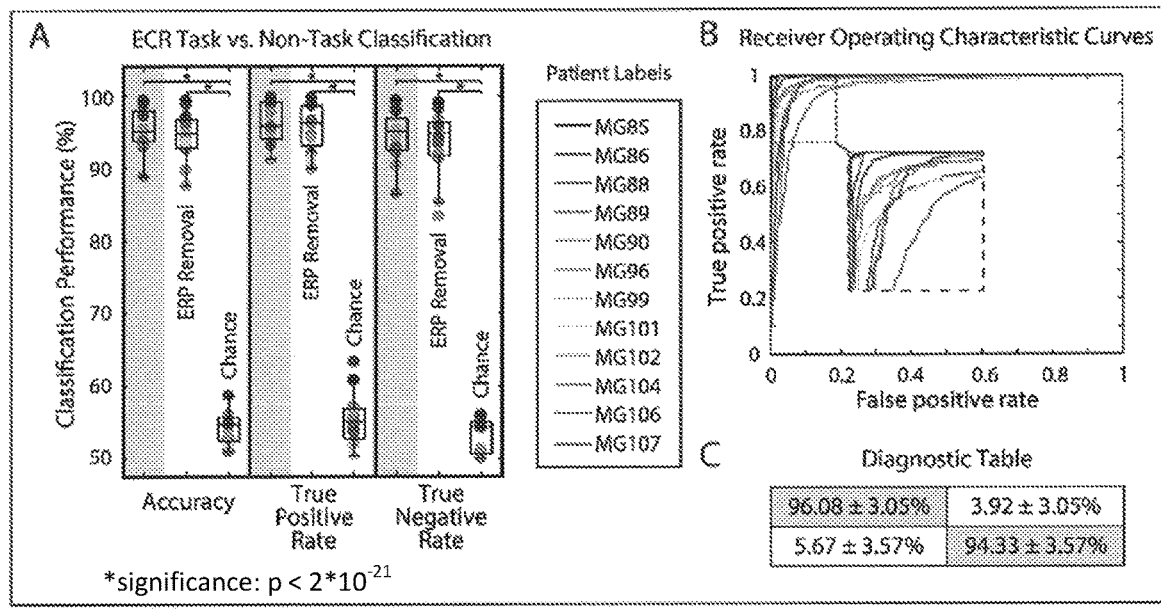
FIG. 21 shows an example of performance of a classification model trained in accordance with some embodiments of the disclosed subject matter on ECR task and non-task data collected from various subjects.

FIG. 21 shows an example of performance of a classification model trained in accordance with some embodiments of the disclosed subject matter on ECR task and non-task data collected from various subjects. As shown in FIG. 21, there was no significant difference between MSIT vs. non-task and ECR vs. non-task classification performance. Mean sensitivity and specificity for ECR task vs. non-task classification was 96.08±3.05% and 94.33±3.57% (n=12), respectively.

Figure 22:
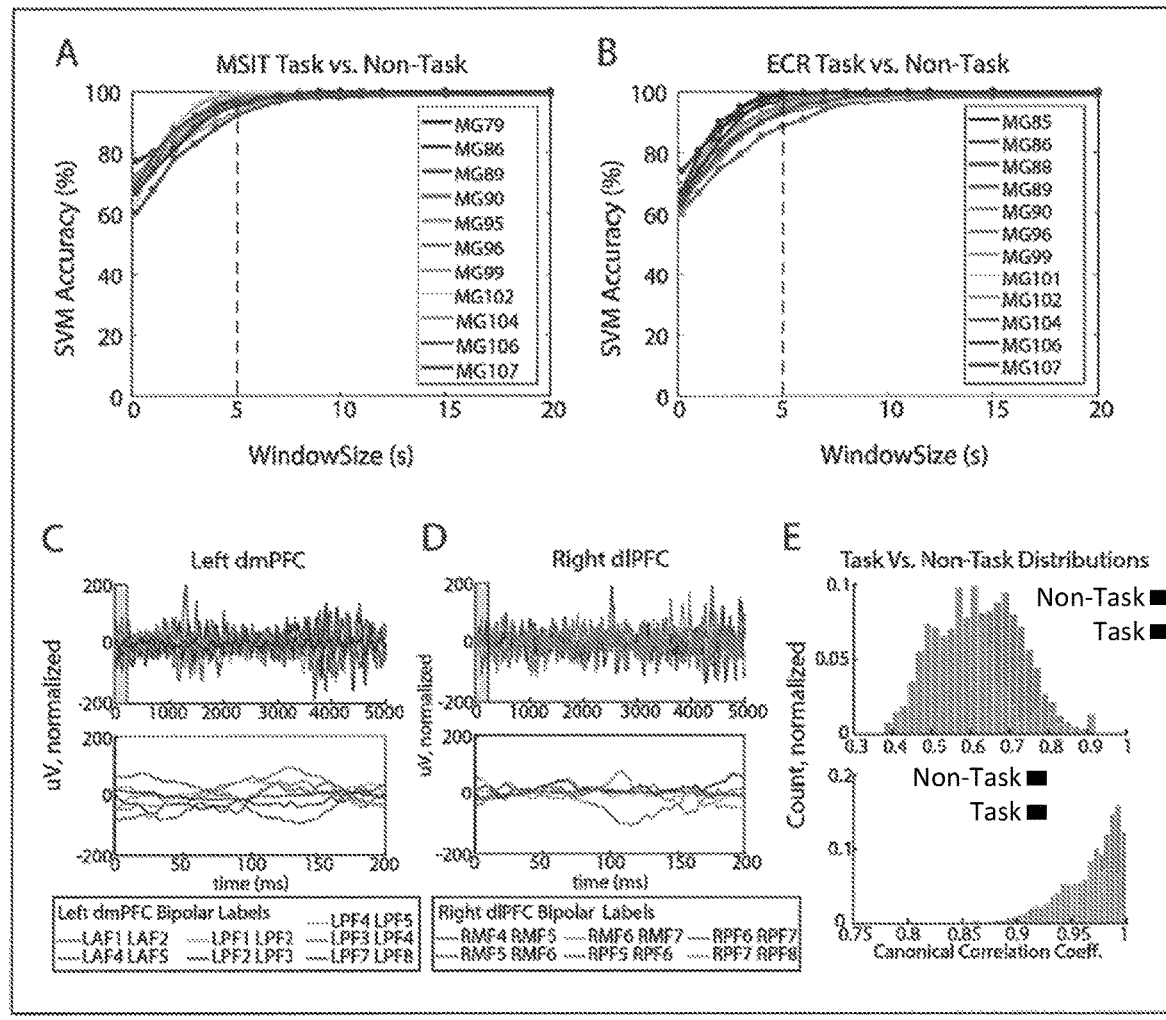
FIG. 22 shows examples of performance of classification models trained in accordance with some embodiments of the disclosed subject matter using various window sizes to sample data.

FIG. 22 shows examples of performance of classification models trained in accordance with some embodiments of the disclosed subject matter using various window sizes to sample data. As shown in FIG. 22, at a window size of around five seconds, accuracy of the trained classification model was at or above 90% for each subject. Canonical correlation carries an innate bias, in that coefficients increase as sample lengths decrease. At small window sizes, coefficients approach their maximum value of one which makes task and non-task distributions less distinguishable at smaller window sizes. For example, as shown at the bottom right, over a 200 ms window, canonical correlation coefficients are skewed towards the right for both non-task and task distributions. By comparison, at the center right, over a five-second window, canonical correlation coefficients are less skewed and distributions become more distinguishable. Classification accuracies were calculated across window sizes ranging from 200 ms to 20 seconds in order to provide information that can be used to select a window size that balances tradeoffs between computational limitations and classification performance. As shown in FIG. 22, using a four to five-second window provides most of the increases in classification accuracy that can be gained by increasing the size of the window due to the exponential increase in classification accuracy occurring before five seconds.

Figure 23:
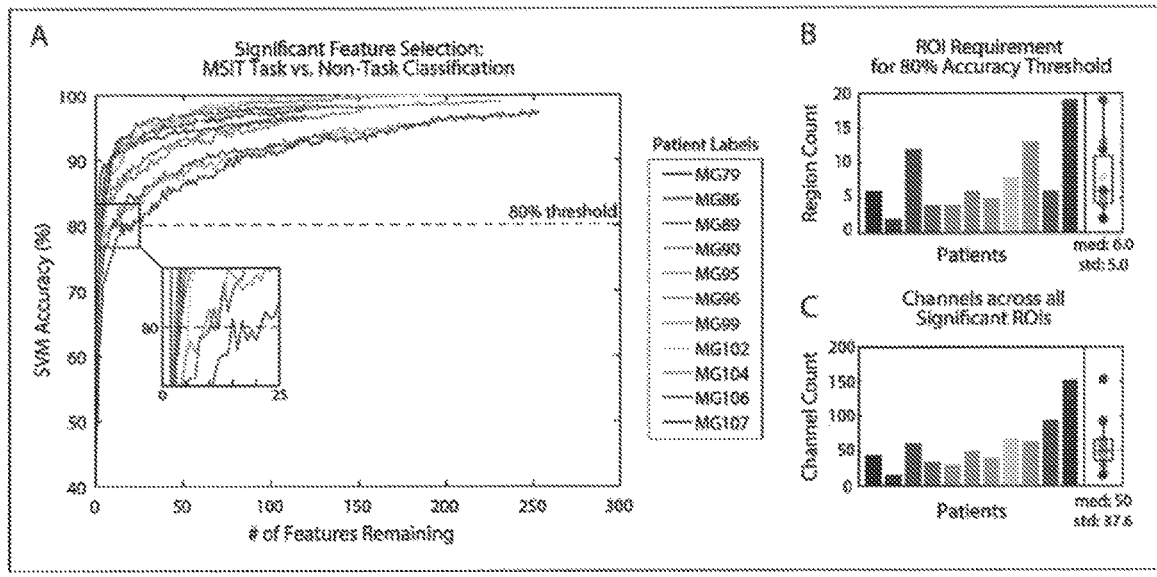
FIG. 23 shows examples of performance of classification models trained in accordance with some embodiments of the disclosed subject matter for various subjects on MSIT task and non-task data using various numbers of features extracted from the data, the number of regions of interest needed to produce relatively accurate result, and the number of channel.

FIG. 23 shows examples of performance of classification models trained in accordance with some embodiments of the disclosed subject matter for various subjects on MSIT task and non-task data using various numbers of features extracted from the data, the number of regions of interest needed to produce relatively accurate result, and the number of channel. As shown in FIG. 23, at a relatively low number of features (e.g., less than about 25 across all patients) accuracy of the trained classifier exceeds 80% based on signals generated during the MSIT task.

Figure 24:
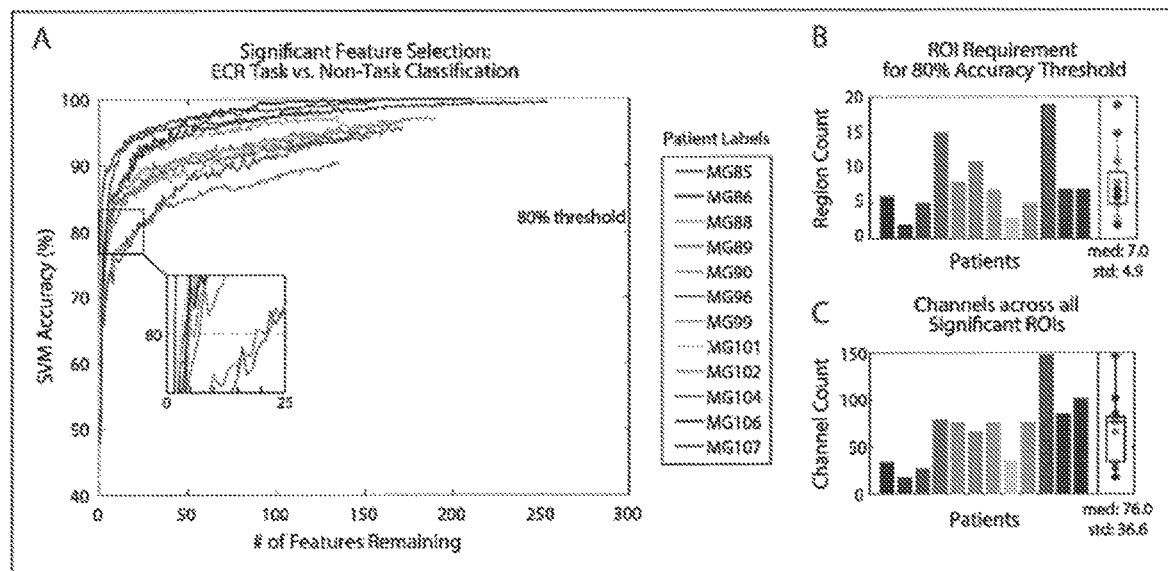
FIG. 24 shows examples of performance of classification models trained in accordance with some embodiments of the disclosed subject matter for various subjects on ECR task and non-task data using various numbers of features extracted from the data, the number of regions of interest needed to produce relatively accurate result, and the number of channel.

FIG. 24 shows examples of performance of classification models trained in accordance with some embodiments of the disclosed subject matter for various subjects on ECR task and non-task data using various numbers of features extracted from the data, the number of regions of interest needed to produce relatively accurate result, and the number of channel. As shown in FIG. 24, at a relatively low number of features (e.g., less than about 25 across all patients) accuracy of the trained classifier exceeds 80% based on signals generated during the ECR task.

The data shown in FIGS. 23 and 24 were generated using the process for determine features described above in connection with 412 of FIG. 4. The threshold for clinical success was defined as 80% accuracy based on current motor brain machine interface decoding standards. Results of the ranking process described above in connection with 412 of FIG. 4 are shown in FIGS. 23 and 24, which shows SVM accuracy decreasing as region pairs are iteratively dropped from the feature set. The remaining features were significant when accuracy reached the 80% threshold marked by the dotted lines. Significant features required to maintain 80% accuracy vary across patients in quantity, as shown in the inset portions of FIGS. 23 and 24 showing accuracy from zero to 25 features around the 80% accuracy threshold (MSIT: med 3±3.4 region pairs, ECR: med 4±6.6 region pairs). Quantifying the number of significant features can allow for assessment of recording requirements necessary to reach the threshold for clinical success for each individual subject. The number of regions (rather than region pairs) required to meet 80% accuracy ranged from two to 19 for both the MSIT (med 6.0; std 5.0) and ECR (med 7.0; std 4.9) tasks. The total number of channels (before bipolar referencing) implanted across the set of significant regions ranged from 16 to 153 for the MSIT task (med 50; std 37.6), and 17 to 148 for the ECR task (med 76.0; std 36.6).

Figure 25:
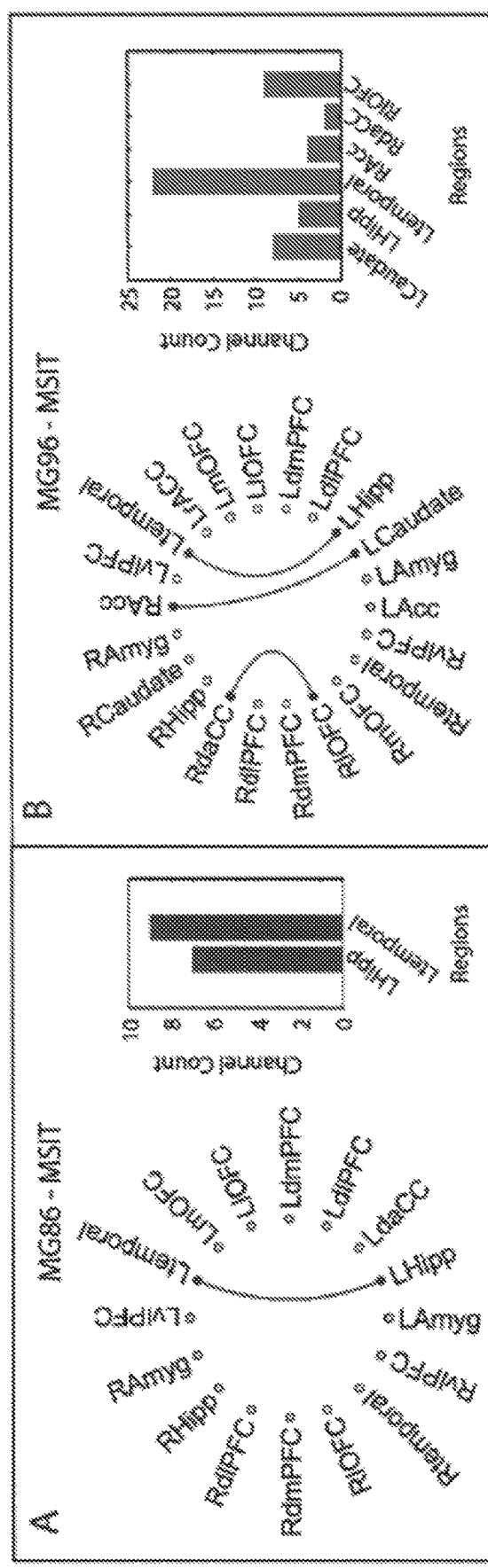
FIG. 25 shows examples of network diagrams and connectivity of brain regions calculated for two different subjects based on neural activity data collected during performance of the MSIT test.
Figure 26:
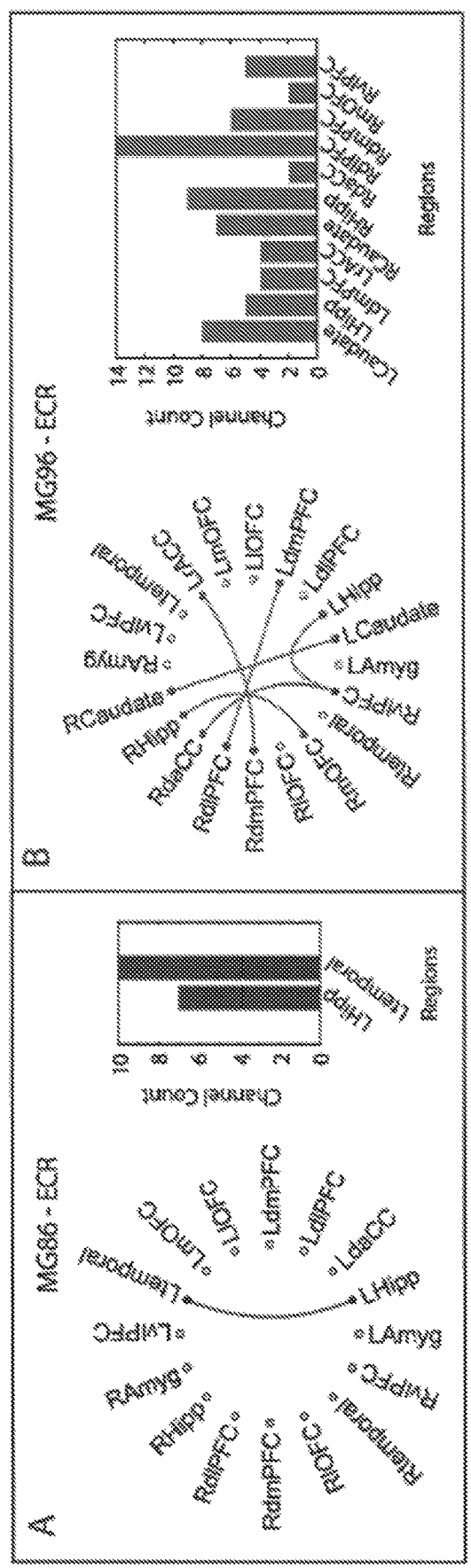
FIG. 26 shows examples of network diagrams and connectivity of brain regions calculated for two different subjects based on neural activity data collected during performance of the ECR test.

FIG. 25 shows examples of network diagrams and connectivity of brain regions calculated for two different subjects based on neural activity data collected during performance of the MSIT test, and FIG. 26 shows examples of network diagrams and connectivity of brain regions calculated for two different subjects based on neural activity data collected during performance of the ECR test. As shown in FIGS. 25 and 26, in addition to varying in quantity, significant features are unique to each patient with limited overlap between patients engaged in the same task. For example, the unique feature sets required to reach the 80% accuracy for two subjects, MG86 and MG96, during the MSIT and ECR tasks are shown as network diagrams in FIGS. 25 and 26. The number of raw channels implanted in each significant region is shown to the right of the network diagrams. As shown in FIGS. 25 and 26, while subject MG86 showed relatively consistent results across the MSIT and ECR tasks, subject MG96 showed substantially different results across the two tasks. Accordingly, while significant features are unique to each patient performing the same task, significant features may also be unique for the same subject performing different types of tasks.

Figure 27:
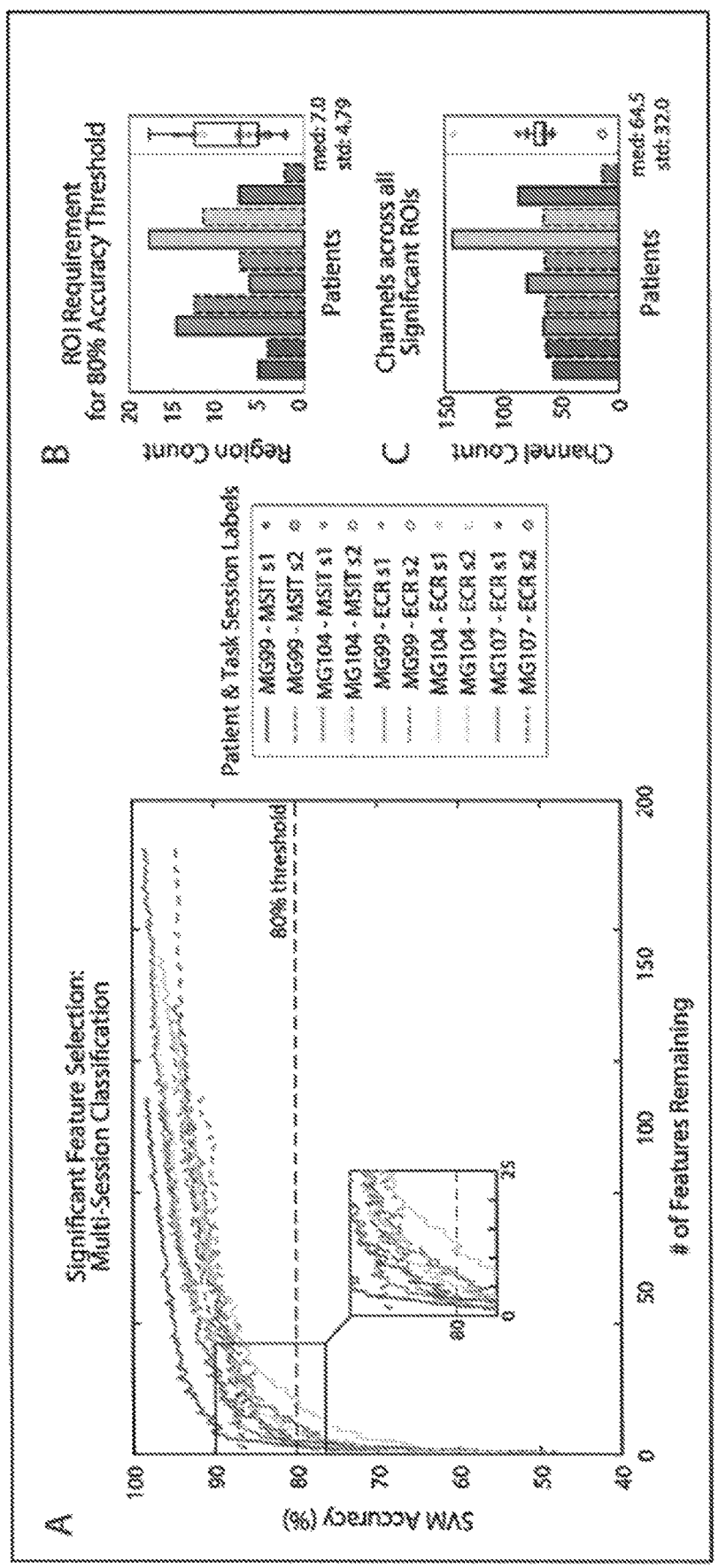
FIG. 27 shows examples of performance of classification models trained in accordance with some embodiments of the disclosed subject matter for various subjects on MSIT task and non-task data using various numbers of features extracted from the data and comparisons of performance for the same patient using data collected during different MSIT sessions.

FIG. 27 shows examples of performance of classification models trained in accordance with some embodiments of the disclosed subject matter for various subjects on MSIT task and non-task data using various numbers of features extracted from the data and comparisons of performance for the same patient using data collected during different MSIT sessions. As shown in FIG. 27, feature sets required to meet 80% classification accuracy varied across multiple sessions of the same task within each subject. The most influential region pairs among feature sets across multiple recording sessions were again selected through a ranking process based on SVM criteria (e.g., as described above in connection with 412 of FIG. 4). The results of the ranking process are shown in FIG. 27, where the inset shows the number of features required to meet 80% accuracy (med 5.0; std 5.65). The number of regions required to meet 80% accuracy ranged from two to 17 (med 7; std 4.79) (FIG. 26). The total number of channels (before bipolar referencing) implanted across the sets of significant regions ranged from 14 to 143 (med 64.5; std 28.22). The second ECR session completed by MG 107 yielded the only classification performance above 80% accuracy based on only a single feature, the canonical correlation between the right dorsal anterior cingulate cortex and the left caudate.

Figure 28:
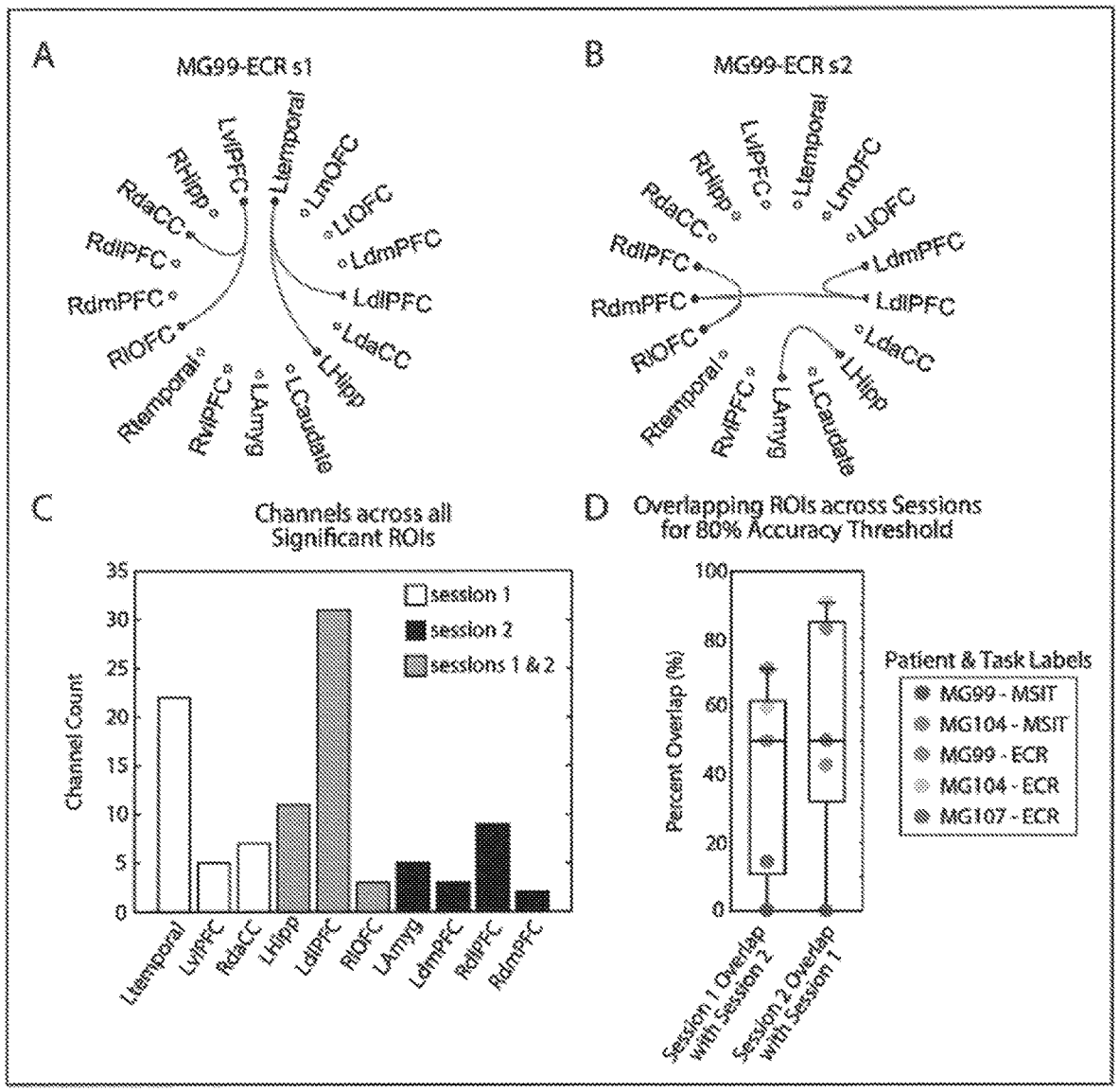
FIG. 28 shows examples of network diagrams and channel counts for various brain regions calculated for two different sessions of the MSIT test by the same subject.

FIG. 28 shows examples of network diagrams and channel counts for various brain regions calculated for two different sessions of the MSIT test by the same subject. FIG. 28 includes a more detailed example of how significant features varied for one particular subject from session to session, with fluctuating degrees of overlap among significant regions between sessions. The unique feature sets required to reach 80% accuracy for one example pair of recording sessions, MG99 engaged in the ECR task, are shown as network diagrams in FIG. 28. No features deemed significant during the first recording session were declared significant during the second recording session. However, there was some overlap in individual regions of interest (rather than in terms of the features, which are region pairs). The left hippocampus, left dlPFC, and right lateral orbitofrontal cortex (lOFC) are shared as significant ROIs between sessions one and two. There was overlap between required regions in three of four session pairs analyzed. The mean percentages of significant regions from session one that exist in session two and vice versa are ~55% and ~62%, respectively. The distribution of overlap varies widely across recording sessions, ranging from 0% for MG99 during the MSIT Task to ~92% for MG104 during the second session of the ECR task.

Figure 29:
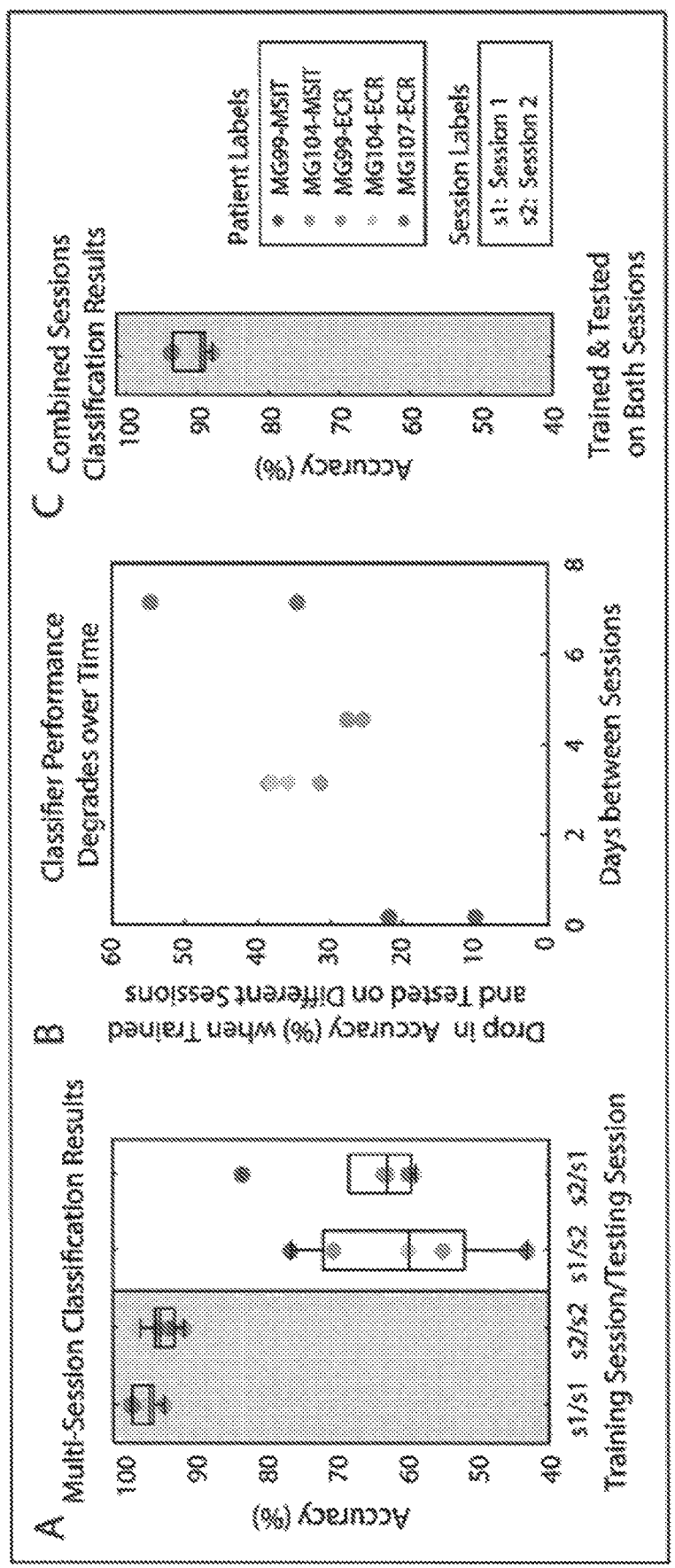
FIG. 29 shows examples of performance of classification models trained in accordance with some embodiments of the disclosed subject matter using data collected during one session to classify data collected during another sessions for the same subject, and results when the classifier is trained using data from both sessions.

FIG. 29 shows examples of performance of classification models trained in accordance with some embodiments of the disclosed subject matter using data collected during one session to classify data collected during another sessions for the same subject, and results when the classifier is trained using data from both sessions. As shown in FIG. 29, when training and testing on the same session, the classifier yielded accuracies greater than 90% for each of the session pairs. To test classification performance across multiple sessions of data, the classifier was trained on features from one session and tested on the other session in its pair. Training and testing the classifier on different sessions caused accuracy to degrade significantly, although performance was still above chance levels. Accuracy degraded as the amount of time between sessions increased.

FIG. 30 shows, for each subject, the number of sessions of each test during which data was collected, the number of Neural Signal Processors (NSPs) recording systems used to collect the data, and the number of electrodes used to collect data from each hemisphere of the brain.

Figure 31:
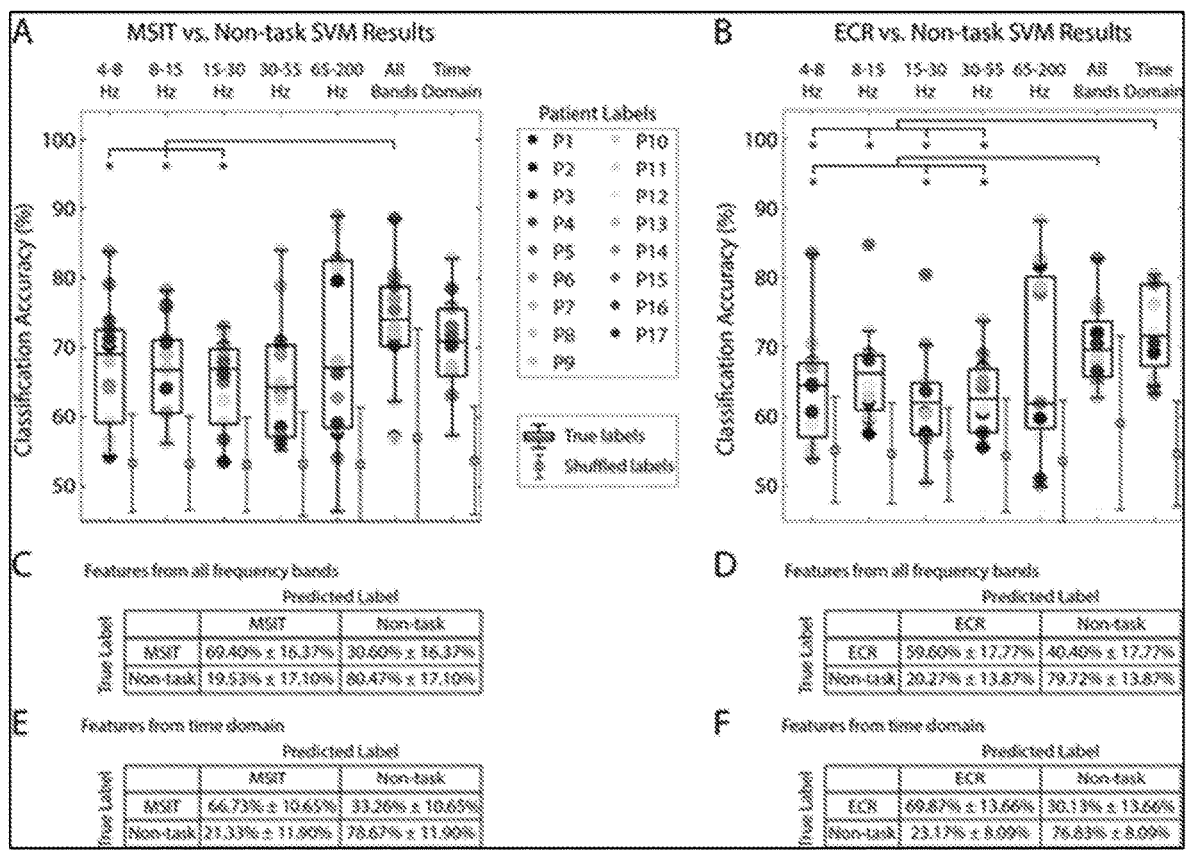
FIG. 31 shows examples of performance of classification models trained in accordance with some embodiments of the disclosed subject matter for various subjects on MSIT task and non-task data using data in various frequency bands, and on ECR task and non-task data using data in various frequency bands.

FIG. 31 shows examples of performance of classification models trained in accordance with some embodiments of the disclosed subject matter for various subjects on MSIT task and non-task data using data in various frequency bands, and on ECR task and non-task data using data in various frequency bands. As shown in FIG. 31, changes in canonical coherence estimates observed from whole brain invasive neurophysiology were used to detect task engagement in humans performing both the MSIT and ECR task using various sets and subsets of collected data. Median accuracy for MSIT vs. Non-task classification (N=14) using canonical coherence features from frequency bands of 4-8 Hz, 8-15 Hz, 15-30 Hz, 30-55 Hz, and 65-200 Hz was 69.14%±8.55%, 66.86%±6.95%, 67.02%±5.91%, 64.39%±8.40%, 67.17%±13.34%, 74.10%±8.68%, respectively. Median accuracy for MSIT vs. Non-task classification using canonical correlation features was 70.94%±6.41%. MSIT vs. Non-task classification accuracy using canonical coherence features from all frequency bands of interest was significantly greater than classification accuracy using canonical coherence features from frequency bands of 4-8 Hz, 8-15 Hz, and 15-30 Hz (p<0.05). MSIT vs. Non-task classification accuracy was significantly greater than chance performance (p<0.05). Median true positive rate and true negative rate for MSIT vs. Non-task classification using canonical coherence features from all frequency bands was 69.40%±16.37% and 80.47%±17.10%, respectively. Median true positive rate and true negative rate for MSIT vs. Non-task classification using canonical correlation features was 66.73%±10.65% and 78.67%±11.90%, respectively.

Median accuracy for ECR vs. Non-task classification (N=12) using canonical coherence features from frequency bands of 4-8 Hz, 8-15 Hz, 15-30 Hz, 30-55 Hz, and 65-200 Hz was 64.58%±7.94%, 66.33%±7.05%, 62.11%±5.31%, 62.66%±5.31%, 61.97%±12.68%, and 69.68%±5.58%, respectively. Median accuracy for ECR vs. Non-task classification using canonical correlation features was 71.70%±5.97%. ECR vs. Non-task classification accuracy using canonical coherence features from all frequency bands of interest was significantly greater than classification accuracy using canonical coherence features from frequency bands of 4-8 Hz, 15-30 Hz, and 30-55 Hz (p<0.05). ECR vs. Non-task classification accuracy using canonical correlation features was significantly greater than classification accuracy using canonical coherence features from frequency bands of 4-8 Hz, 8-15 Hz, 15-30 Hz, and 30-55 Hz (p<0.05). ECR vs. Non-task classification accuracy was significantly greater than chance performance (p<0.05). Median true positive rate and true negative rate for ECR vs. Non-task classification using canonical coherence features from all frequency bands was 59.40%±17.77% and 79.72%±13.87%, respectively. Median true positive rate and true negative rate for ECR vs. Non-task classification using canonical correlation features was 69.87%±13.66% and 76.83%±8.09%, respectively.

Figure 32:
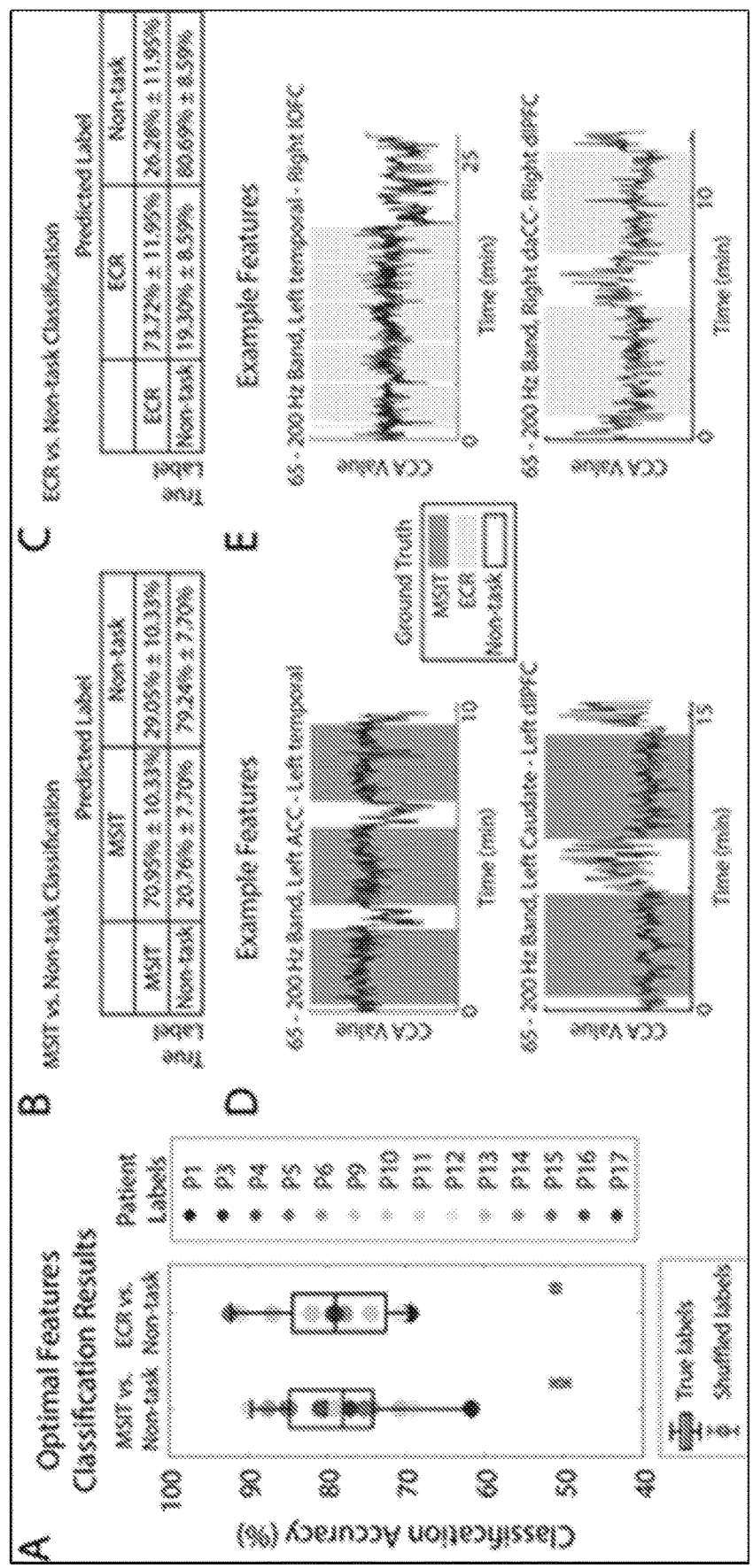
FIG. 32 shows examples of performance of classification models trained in accordance with some embodiments of the disclosed subject matter for various subjects using an optimal set of features on MSIT task and non-task data using data in various frequency bands, and on ECR task and non-task data using data in various frequency bands.

FIG. 32 shows examples of performance of classification models trained in accordance with some embodiments of the disclosed subject matter for various subjects using an optimal set of features on MSIT task and non-task data using data in various frequency bands, and on ECR task and non-task data using data in various frequency bands. As shown in FIG. 31, median accuracy for MSIT vs. Non-task classification (N=14) and ECR vs. Non-task classification (N=12) using optimal canonical coherence features was 78.10%±7.39% and 78.97%±7.36%, respectively. MSIT vs. Non-task classification accuracy and ECR vs. Non-task classification accuracy was significantly greater than chance performance (p<0.05). Median true positive rate and true negative rate for MSIT vs. Non-task classification using optimal canonical coherence was 70.95%±10.33% and 79.24%±7.70%. Median true positive rate and true negative rate for ECR vs. Non-task classification using optimal canonical coherence was 73.72%±11.95% and 80.69%±8.59%.

Figure 33:
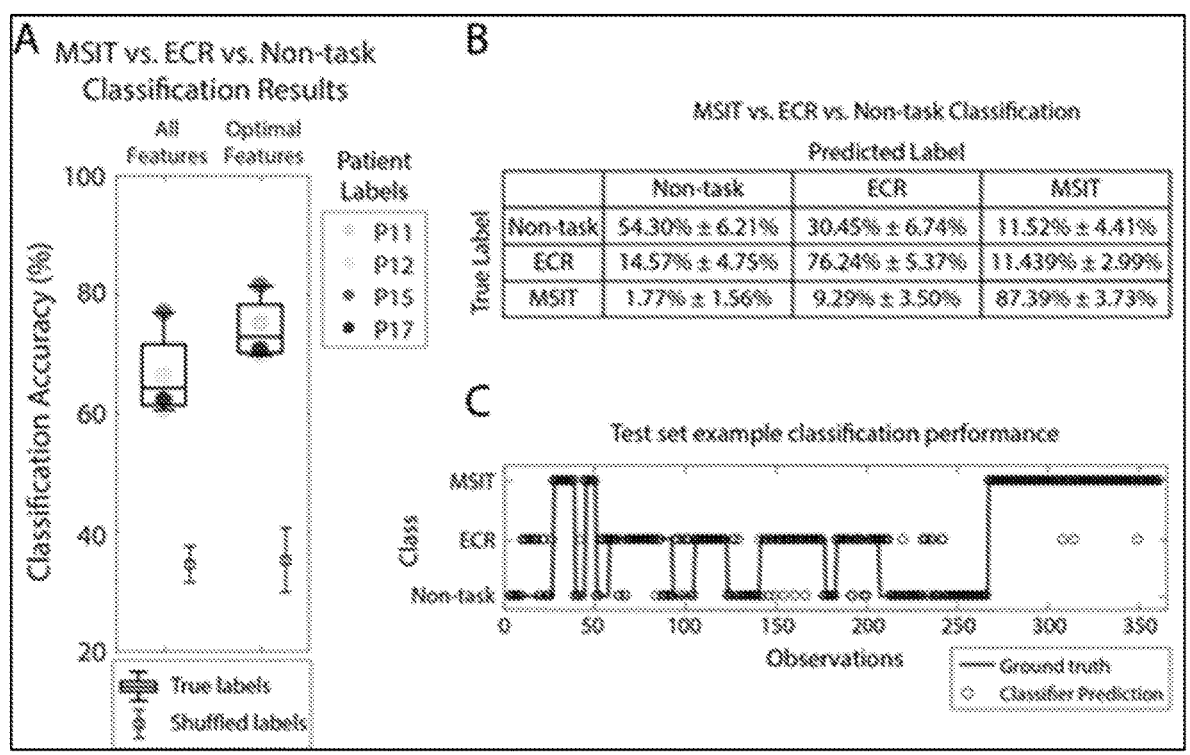
FIG. 33 shows examples of performance of classification models trained in accordance with some embodiments of the disclosed subject matter for various subjects on MSIT and ECR task and non-task data using all features and an optimal set of features.

FIG. 33 shows examples of performance of classification models trained in accordance with some embodiments of the disclosed subject matter for various subjects on MSIT and ECR task and non-task data using all features and an optimal set of features. As shown in FIG. 32, changes in canonical coherence estimates were used to distinguish alternating engagement in MSIT, ECR task, and Non-task activities. Median accuracy for MSIT vs. ECR vs. Non-task classification (N=4) using all canonical coherence features was 64.27%±6.35%. Median accuracy for MSIT vs. ECR vs. Non-task classification (N=4) using optimal canonical coherence features was 72.90%±4.67%. MSIT vs. ECR vs. Non-task classification accuracy using all canonical coherence features and optimal canonical coherence features was significantly greater than chance performance (p<0.05). Median Non-task detection rate, MSIT detection rate, and ECR task detection rate using optimal canonical coherence features was 49.17%±6.80%, 75.18%±5.42%, and 87.60%±4.07%, respectively.

FIG. 34 shows an example of a bipolar electrode localization table for various subjects that performed the MSIT task.

FIG. 35 shows an example of a bipolar electrode localization table for various subjects that performed the ECR task.

Fourteen participants, each with a history of long-standing pharmaco-resistant complex partial seizures, underwent clinically-indicated invasive monitoring to confirm seizure focus. The research on neural activity during the MSIT and ECR task was completed while the participants were in the hospital awaiting seizures for clinical mapping of foci. The decision to implant electrodes and the number, types, and location of implantations were all determined on clinical grounds by a team of caregivers independent of the study. Participants were informed that participation in the experiment would not alter their treatment in any way and that they could withdraw at any time without jeopardizing their clinical care. Each participant gave fully informed consent according to NIH guidelines, and all procedures were approved by the local institutional review board. The depth electrodes were stereotactically implanted to monitor and identify seizure foci. The implantation procedure involved placing the participant under general anesthesia, followed by implantation of multi-lead depth electrodes in stereotactically identified regions. The depth electrodes had diameters of 0.8-1.0 mm and 8-16 platinum/iridium-contact leads 2.4 mm long were stereotactically placed in locations deemed necessary for seizure localization by the team of caregivers caring for the individual participant. Angled electrode trajectories were achieved through a ROSA® robotic system made by MEDTECH SA of Montpellier, France. The participants received bilateral electrodes ranging from five to nine electrodes in the right hemisphere, and five to eight electrodes in the left hemisphere. Each participant's electrode montage was determined solely by clinical mapping considerations. Intracranial LFP recordings were acquired using one or two Neural Signal Processor NSP recording systems at a sampling rate of 2 kHz. Depth recordings were referenced to one scalp EEG electrode during acquisition.

Data analysis was performed using custom analysis code in Matlab (MathWorks) and Fieldtrip, an open source software implemented in Matlab. All data were down-sampled to 1,000 Hz and demeaned relative to the entire recording. Line noise and its harmonics up to 200 Hz were removed by subtracting a bandpass filtered signal from the raw signal on each channel. Neighboring channels were bipolar referenced relative to one another to reduce the effects of volume conduction. Channels that exhibited excessive line noise or no discernible signal were removed from the analysis. Based on clinical reports and on visual inspection, electrodes surrounding the epileptic focus and/or exhibiting abnormal activities were also excluded.

Neighboring channels were bipolar referenced relative to one another to account for volume conduction. The signal recorded from each channel represented the reference potential, R, subtracted from the electric potentials gathered at the site of two electrodes, Source1 and Source2. To eliminate the reference component of the signal that is common across nearby electrodes, adjacent signals were subtracted from one another, which can be represented as:

$$\text{Bipolar Signal}=(\text{Source1}-R)-(\text{Source2}-R), \quad (21)$$

which can be simplified as $$\text{Bipolar Signal}=\text{Source1}-\text{Source2} \quad (22)$$

which represents a bipolar referenced signal. Low frequency components of the signal are thought to be related to evoked-response potentials (ERPs) that occur during task image onset or reaction.

Each NSP sampled data according to its own clock cycle, controlled by crystal oscillators with each clock oscillating at a slightly different frequency. The difference in oscillation rates at a sampling rate of 2,000 Hz generated a drift between recordings at approximately one to two samples every 20 minutes. In order to synchronize recordings, event time stamps were saved along with neural data from both NSPs, which were used as synchronization points. If the number of samples between event time stamps did not match both recordings, the shorter interval of data was adjusted via linear interpolation so that its length is matched to the size of the longer interval of data.

FCCA was applied to neural data collected during experimental behavioral tasks to extract neural features related to effortful decision-making. These neural features were used as input to an SVM classifier to predict task-related brain states. Canonical coherence features successfully distinguished periods of task engagement from free behavior for both the MSIT (N=14) and ECR task (N=12). Classifier performance was maintained by selecting up to five optimal features per participant. Further, the classifier was able to distinguish MSIT state, ECR task state, and non-task state within a single recording session (N=4), suggesting that the method shows promise for distinguishing multiple types of mental efforts.

Data was windowed using a four second window sliding every two seconds. Each four second window of data was labeled as "task" or "non-task" depending on whether the participant was actively engaged in the MSIT and ECR behavioral tasks. Both image presentation and fixation periods were included in the "task" label assignment. A three-second buffer was placed at the start and end of "task" periods to allow for ramp-up and ramp-down periods. The length of "task" periods are determined by the number of task blocks the participant agreed to participate in. "Non-task" labels were assigned to portions of the recording collected immediately before and after task engagement, as well as during any breaks the participant opted to take while playing the task. During "non-task" periods, the participant was behaving freely and was not engaged in the task. Task blocks were only used to compute the fixed projection space (e.g., as described above in connection with 410 of FIG. 4), specifically EQS. 19 and 20, based on the assumption that task periods would be more homogenous than non-task periods.

The canonical correlation algorithm was not dependent on the cyclic ERPs inherent to the task-related data. Image presentation and movement associated with reaction are reliably associated with a wave of slow frequency activity across most channels. While ERPs also appear throughout the non-task data, free behavior does not require focused attention to an image that appears on a screen approximately every five seconds. If classification performance was dependent on low frequency activity, the real-world implications of the classifier would be limited as the algorithm would be tied to contexts related to experimental behavioral tasks. To test whether classification performance is dependent on task-related cyclic ERPs, low frequency activity (<2 Hz) was removed from the signal by applying a high-pass filter (e.g., as described above in connection with FIG. 15), and canonical correlation features were recalculated using signals from the filtered data. No significant differences were found between classification performance before and after filtering.

While there was a positive bias in chance classification performance, true performance significantly outperformed chance performance (MSIT task vs. non-task: $p<0.01$; ECR task vs. non-task: $p<0.01$). The classification accuracy expected after shuffling labels was approximately 50%, and the observed mean classification accuracy was $55.2\pm2.62\%$ and $54.3\pm2.18\%$ for the MSIT and ECR tasks, respectively. A positive bias may have been introduced by the resampling procedure used to balance class sizes. If one sample is overrepresented in the balanced dataset due to resampling, the same sample is likely to be included in both testing and training datasets. Testing the classifier on a portion of training data introduces a positive bias, evident from the inflated chance classification performance.

Canonical correlation or coherence features and corresponding "task" vs. "non-task" class labels were used as classifier input. The MSIT vs. ECR. vs. Non-task classification model and prediction used three binary SVM models. These models were trained using one versus one coding design such that one class is positive, one class is negative, and the other is ignored. Canonical coherence features and corresponding "ECR task", "MSIT", and "Non-task" class labels were used as classifier input. The one versus one coding scheme applied a majority voting scheme to determine the predicted label of new observations.

Training and testing sets were assigned using a five-fold cross validation strategy where the feature set was separated into five folds. Four folds were used for training and the remaining fold was used for testing. This process was repeated until every fold was used for testing. Task data exceeded non-task data for 18 of 24 recording sessions analyzed. To balance unequal "task" and "non-task" class sizes, a data-level approach agnostic of the classification algorithm was used. The class of smaller size was augmented by random oversampling with replacement within the training set and testing set to make up the difference between class sizes. The supplemental feature set was then concatenated to the original feature set. Datasets with less than 20% non-task data were dropped from analysis (totaling 7 recording sessions). To preserve the chronological structure of the data during classification, the feature set was windowed before training and testing set labels were assigned. Classification performance was not dependent on features estimated from overlapping data that appear in both the training and testing set. In some embodiments, five-fold cross validation was repeated 1,000 times. Accuracy, true positive rate (sensitivity), true negative rate (specificity), false positive rate, and false negative rate were calculated on each iteration of the five-fold cross validation strategy to gauge classifier performance.

Classification performance due to chance was calculated by shuffling class labels before class sizes are balanced. Labels are randomly assigned in a way that preserves original class sizes before classes are balanced. Five-fold cross validation was repeated 1,000 times. Training set features were correlated with class labels and the top 25 correlated features across all frequency bands of interest were run through a greedy-like feature selection process. The features most correlated with class labels would typically align with the optimal features selected through the greedy-like process.

The sample size for the study was limited (MSIT vs. Non-task classification: N=14, ECR vs. Non-task classification: N=12, MSIT vs. ECR vs. Non-task classification: N=4). Datasets were imbalanced in terms of the number of Task and Non-task observations. Chance prediction for Task vs. Non-task classification and ECR task vs. MSIT vs. Non-task classification using optimal features was approximately 51% and 35%, which is slightly greater than the chance level expected for two- and three-class classification problem (50% and 33.3%). The resampling procedure used to balance class sizes may have introduced both a positive bias for chance prediction and a discrepancy between sensitivity and specificity per participant. The difference between sensitivity and specificity had a positive, linear relationship with the log ratio of Task to Non-task class sizes. For datasets that required little to no resampling, the difference between sensitivity and specificity was close to zero. There is not a significant difference between sensitivity and specificity when training the classifier on datasets with balanced class sizes.

Optimal feature selection maintained classification performance across subjects. Optimal region pairs among the feature set were selected through a ranking process based on SVM criteria, during which the feature dropped at each iteration contributed least to upholding SVM accuracy. Between one to five canonical coherence estimates per participant yields optimal classification performance.

The classifier was trained on features from one session and tested on the other session in order to test MSIT vs. Non-task and ECR vs. Non-task classification (N=4) performance across multiple sessions of recordings. Training and testing the classifier on different sessions caused accuracy to degrade significantly from performance of a classifier built and trained on data collected during the same recording sessions.

When training and testing the classifier on data from both sessions, mean classifier performance accuracy across patients was approximately 89%. The classification performance improvement that we observe indicates that training on temporally separated data will improve classification performance over longer periods of time.

To reduce computational requirements and gain insight on functional connectivity important for distinguishing task-related brain states, a small number of optimal features per participant were identified that are important for detecting task engagement. These optimal features differed across tasks and participants. This may be due to differing numbers of electrodes implanted in each brain region across participants. However, classification performance was not dependent on any one implant scheme. Successful classification performance across many configurations of electrodes suggests extensive regional network involvement in generating task-related brain states. This suggests that it may be possible for relevant features to be derived non-invasively. Further, selecting a subset of optimal features may be useful for guiding implant locations and reducing computational requirements.

One important performance measure for decoders independent of application is the ability to predict above chance levels, and chance prediction was approximately 55%, which is slightly greater than the chance level expected for a two-class classification problem (½ or 50%). Random labels were assigned to data samples in a way that preserved original class sizes before the smaller class size was augmented via resampling. Choosing to assign random labels before resampling likely introduced a bias in classification performance due to the overrepresentation of a subset of samples in the dataset. Additionally, the inflated chance performance indicates that the overall classification performance is inflated as well. For 15 of 23 recordings analyzed, the non-task class size was less than half the task class size.

The timeframe between brain state onset and application of therapy is likely to affect both efficacy and patient satisfaction with treatment. The developed techniques extracted canonical correlation features from windows of data (e.g., 4 second or 5 second windows), which automatically sets a baseline for how quickly closed-loop intervention can occur if the window is moved without significant overlap. For example, if the mechanisms described herein are operating in real-time and the onset of a pathological brain state begins toward the start of a five second window, at least five seconds will pass before the brain state is detected while the mechanisms gather additional data to fill the rest of the window. This five-second estimate does not include the additional time required for feature extraction, classification, and control. While this timeframe would not be acceptable in the realm of motor brain machine interfaces (BMis), where naturalistic control of effectors (e.g. cursors, prosthetic limbs) requires immediate action, and "thought-to-action" brain states are transient, a delay on the order of approximately 10 seconds may be acceptable for treating neuropsychiatric illness if brain states are slowly evolving in a way that mirrors behavioral symptoms.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the process of FIGS. 4 and 5 can be executed or performed in any order or sequence not limited to the order and sequence shown and described in the figures. Also, some of the above steps of the process of FIGS. 4 and 5 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for detecting an effortful mental state and providing stimulation to facilitate performance of an associated effortful mental task, the system comprising:
   a plurality of monitoring sensors, each of the plurality of monitoring sensors configured to capture signals indicative of neural activity from one or more regions of a subject's brain using one or more contacts;
   an implanted stimulator configured to provide stimulation to a region of the subject's brain adjacent to the implanted stimulator; and
   one or more hardware processors programmed to:
      receive a first set of neural data corresponding to neural signals recorded while the subject performed the effortful mental task, the first set of neural data including:
         a first subset of neural data from a first set of contacts associated with a first region of the subject's brain; and
         a second subset of neural data from a second set of contacts associated with a second region of the subject's brain;
      receive a second set of neural data corresponding to neural signals recorded while the subject did not perform the effortful mental task, the second set of neural data including:
         a third subset of neural data from the first set of contacts associated with the first region of the subject's brain; and
         a fourth subset of neural data from the second set of contacts associated with the second region of the subject's brain;
      calculate, based on the first subset of neural data and the second subset of neural data, a first value indicative of a correlation between activity in the first region of the subject's brain and activity in the second region of the subject brain;
      calculate, based on the third subset of neural data and the fourth subset of neural data, a second value indicative of a correlation between activity in the first region of the subject's brain and activity in the second region of the subject brain;
      provide a first plurality of values, including the first value, derived from the first neural data to a classification model as examples of a first class;
      provide a second plurality of values, including the second value, derived from the second neural data to the classification model as examples of a second class;
      train the classification model using the first plurality of values and the second plurality of values;
      receive a third set of neural data corresponding to neural signals recorded while the subject's mental state is unknown, the third set of neural data including:
         a fifth subset of neural data from the first set of contacts associated with the first region of the subject's brain; and
         a sixth subset of neural data from the second set of contacts associated with the second region of the subject's brain;
      calculate, based on the fifth subset of neural data and the sixth subset of neural data, a third value indicative of a correlation between activity in the first region of the subject's brain and activity in the second region of the subject brain;
      provide a third plurality of values, including the third value, derived from the third neural data to the trained classification model as input to be classified;
      receive, from the trained classification model, an output indicative of whether the third neural data is a member of the first class or the second class;
      determine, based on the output, that the third neural data is a member of the first class indicating that the subject is experiencing the effortful mental state; and
      in response to determining that the subject is experiencing the effortful mental state, cause the implanted stimulator to provide stimulation to the region of the subject's brain adjacent to the implanted stimulator to augment the subject's brain function.

2. The system of claim 1, wherein the one or more hardware processors are further programmed to:
   calculate the first value based on a canonical correlation analysis using the first subset of neural data as a first input and the second set of neural data as a second input.

3. The system of claim 1, wherein the one or more hardware processors are further programmed to:
   calculate the first value based on a fixed canonical correlation analysis using the first subset of neural data as a first input and the second set of neural data as a second input.

4. The system of claim 1, wherein a first monitoring sensor of the plurality of monitoring sensors comprises a depth electrode implanted into the first region of the subject's brain, the depth electrode comprising a plurality of contacts.

5. The system of claim 1, wherein a first monitoring sensor of the plurality of monitoring sensors comprises an intracranial electrode positioned to generate electrocorticography signals based on signals from first region of the subject's brain.

6. The system of claim 1, wherein a first monitoring sensor of the plurality of monitoring sensors comprises a scalp electrode positioned to generate electroencephalography signals based on signals from first region of the subject's brain.

7. The system of claim 1, wherein the classification model is a support vector machine-based classification model.

8. The system of claim 1, wherein the first subset of neural data and the second subset of neural data comprises neural data from a window of time.

9. The system of claim 8, wherein the window is one to ten seconds.

10. The system of claim 8, wherein the window is four to five seconds.

11. The system of claim 1, wherein the first subset of neural data and the second subset of neural data comprises neural data from a window of time.

12. The system of claim 1, wherein the effortful mental state is a state of heightened cognitive interference.

13. The system of claim 1, wherein the effortful mental state is a state of heightened emotional conflict.

14. The system of claim 1, further comprising an implanted pulse generator comprising a hardware processor of the one or more hardware processors.

15. The system of claim 1, wherein the first subset of neural data from the first set of contacts is organized as a matrix $$X = \begin{bmatrix} X_{1,1} & \cdots & X_{1,t} \\ \vdots & \ddots & \vdots \\ X_{n,1} & \cdots & X_{n,t} \end{bmatrix},$$

where n is a number of channels represented by the first set of contacts and t is the number of samples in a window of time during which the first subset of neural data was recorded, and the second subset of neural data from the second set of contacts is organized as a matrix $$Y = \begin{bmatrix} Y_{1,1} & \cdots & Y_{1,t} \\ \vdots & \ddots & \vdots \\ Y_{n,1} & \cdots & Y_{n,t} \end{bmatrix},$$

where n is the number of channels represented by the second set of contacts and t is the number of samples in a window of time during which the second subset of neural data was recorded.

16. The system of claim 1, wherein the first set of contacts consists of n contacts, and the second set of contacts consists of n contacts that are a subset of m contacts associated with the second region of the subject's brain, where m is greater than n.

17. The system of claim 1, wherein the first set of neural data includes n subsets of neural data, each corresponding to a different region of the subjects brain including the first subset of neural data and the second subset of neural data, and the one or more hardware processors are further programmed to:
calculate a value indicative of a correlation between each combination of two subsets of the n subsets such that at least n!/(n−2)!2! values are calculated, wherein each value is a probability of the two subsets of neural data being correlated.

18. The system of claim 17, wherein n is greater than two.

19. The system of claim 18, wherein n is two to ten.

20. The system of claim 1, further comprising a second implanted stimulator configured to provide stimulation to a region of the subject's brain adjacent to the implanted stimulator.

21. The system of claim 1, wherein the plurality of monitoring sensors comprise at least one of a near-infrared optical sensor, an optical detector configured to detect fluorescence, a magnetometers, an ultrasonic detector, and a nano-mechanical receiver, and wherein the implanted stimulator is configured to stimulate the region of the subject's brain adjacent to the implanted stimulator is configured to stimulate the subject's brain using at least one of electrical stimulation, magnetic stimulation, optical stimulation, and sonic stimulation.

22. A system for detecting an effortful mental state and providing stimulation to augment brain function during the effortful mental state, the system comprising:
a plurality of monitoring sensors each configured to record activity from one or more regions of a subject's brain;
an implanted sensor comprising an electrode configured to provide deep brain stimulation to the subject's brain; and
one or more hardware processors programmed to:
receive first neural data corresponding to activity in a first region of the subject's brain during performance of a task that causes the effortful mental state;
receive second neural data corresponding to activity in a second region of the subject's brain during performance of the task that causes the effortful mental state;
receive third neural data corresponding to activity in the first region of the subject's brain during a non-task period;
receive fourth neural data corresponding to activity in the second region of the subject's brain during the non-task period;
access a classification model including correlations between the first neural data and the second neural data as task data, and correlations between the third neural data and the fourth neural data as non-task data;
receive neural data corresponding to activity in the first region of the subject's brain and the second region of the subject's brain during a period subsequent to accessing the classification model;
provide, as inputs to the classification model, correlations between activity in the first region and the second region during the period subsequent to accessing the classification model;
receive, from the classification model, an output indicating the likelihood that the subject is performing a task that causes the effortful mental state; and
causing, using the implanted electrode, deep brain stimulation to be provided based on the output.

23. A method for detecting an effortful mental state and providing stimulation to facilitate performance of an associated effortful mental task, the method comprising:
receiving, from a plurality of electrodes each comprising at least one contact, a first set of neural data corresponding to neural signals recorded while the subject performed the effortful mental task, the first set of neural data including:
a first subset of neural data from a first set of contacts associated with a first region of the subject's brain; and
a second subset of neural data from a second set of contacts associated with a second region of the subject's brain;
receiving, from the plurality of electrodes, a second set of neural data corresponding to neural signals recorded while the subject did not perform the effortful mental task, the second set of neural data including:
a third subset of neural data from the first set of contacts associated with the first region of the subject's brain; and a fourth subset of neural data from the second set of contacts associated with the second region of the subject's brain;

calculating, based on the first subset of neural data and the second subset of neural data, a first value indicative of a correlation between activity in the first region of the subject's brain and activity in the second region of the subject brain;

calculating, based on the third subset of neural data and the fourth subset of neural data, a second value indicative of a correlation between activity in the first region of the subject's brain and activity in the second region of the subject brain;

providing a first plurality of values, including the first value, derived from the first neural data to a classification model as examples of a first class;

providing a second plurality of values, including the second value, derived from the second neural data to the classification model as examples of a second class;

training the classification model using the first plurality of values and the second plurality of values;

receiving, from the plurality of electrodes, a third set of neural data corresponding to neural signals recorded while the subject's mental state is unknown, the third set of neural data including:
 a fifth subset of neural data from the first set of contacts associated with the first region of the subject's brain; and
 a sixth subset of neural data from the second set of contacts associated with the second region of the subject's brain;

calculating, based on the fifth subset of neural data and the sixth subset of neural data, a third value indicative of a correlation between activity in the first region of the subject's brain and activity in the second region of the subject brain;

providing the third plurality of values, including the third value, derived from the third neural data to the trained classification model as input to be classified;

receiving, from the trained classification model, an output indicative of whether the third neural data is a member of the first class or the second class;

determining, based on the output, that the third neural data is a member of the first class indicating that the subject is experiencing the effortful mental state; and in response to determining that the subject is experiencing the effortful mental state, causing an implanted electrode to provide electrical stimulation to a region of the subject's brain adjacent to the implanted electrode to augment the subject's brain function.

24. A non-transitory computer readable medium containing computer executable instructions that, when executed by a processor, cause the processor to perform a method for detecting an effortful mental state and providing stimulation to facilitate performance of an associated effortful mental task, the method comprising:

receiving, from a plurality of electrodes each comprising at least one contact, a first set of neural data corresponding to neural signals recorded while the subject performed the effortful mental task, the first set of neural data including:
 a first subset of neural data from a first set of contacts associated with a first region of the subject's brain; and
 a second subset of neural data from a second set of contacts associated with a second region of the subject's brain;

receiving, from the plurality of electrodes, a second set of neural data corresponding to neural signals recorded while the subject did not perform the effortful mental task, the second set of neural data including:
 a third subset of neural data from the first set of contacts associated with the first region of the subject's brain; and
 a fourth subset of neural data from the second set of contacts associated with the second region of the subject's brain;

calculating, based on the first subset of neural data and the second subset of neural data, a first value indicative of a correlation between activity in the first region of the subject's brain and activity in the second region of the subject brain;

calculating, based on the third subset of neural data and the fourth subset of neural data, a second value indicative of a correlation between activity in the first region of the subject's brain and activity in the second region of the subject brain;

providing a first plurality of values, including the first value, derived from the first neural data to a classification model as examples of a first class;

providing a second plurality of values, including the second value, derived from the second neural data to the classification model as examples of a second class;

training the classification model using the first plurality of values and the second plurality of values;

receiving, from the plurality of electrodes, a third set of neural data corresponding to neural signals recorded while the subject's mental state is unknown, the third set of neural data including:
 a fifth subset of neural data from the first set of contacts associated with the first region of the subject's brain; and
 a sixth subset of neural data from the second set of contacts associated with the second region of the subject's brain;

calculating, based on the fifth subset of neural data and the sixth subset of neural data, a third value indicative of a correlation between activity in the first region of the subject's brain and activity in the second region of the subject brain;

providing the third plurality of values, including the third value, derived from the third neural data to the trained classification model as input to be classified;

receiving, from the trained classification model, an output indicative of whether the third neural data is a member of the first class or the second class;

determining, based on the output, that the third neural data is a member of the first class indicating that the subject is experiencing the effortful mental state; and in response to determining that the subject is experiencing the effortful mental state, causing an implanted electrode to provide electrical stimulation to a region of the subject's brain adjacent to the implanted electrode to augment the subject's brain function.

* * * * *

UNITED STATES PATENT AND TRADEMARK OFFICE
CERTIFICATE OF CORRECTION

PATENT NO. : 11,612,748 B2
APPLICATION NO. : 16/607989
DATED : March 28, 2023
INVENTOR(S) : Nicole Provenza et al.

Page 1 of 1

It is certified that error appears in the above-identified patent and that said Letters Patent is hereby corrected as shown below:

In the Specification

Column 1, Line 14, "2017, Each" should be --2017. Each--.

Column 26, Line 9, "label. In" should be --label j. In--.

Signed and Sealed this
Twenty-sixth Day of December, 2023

Katherine Kelly Vidal
*Director of the United States Patent and Trademark Office*